US009457074B2

(12) United States Patent
Gourapura et al.

(10) Patent No.: US 9,457,074 B2
(45) Date of Patent: *Oct. 4, 2016

(54) COMPOSITIONS AND METHODS FOR TREATING AND PREVENTING PORCINE REPRODUCTIVE AND RESPIRATORY SYNDROME

(71) Applicant: Ohio State Innovation Foundation, Columbus, OH (US)

(72) Inventors: Renukaradhya J. Gourapura, Wooster, OH (US); Varun Dwivedi, Columbus, OH (US); Basavaraj S. Binjawadagi, Wooster, OH (US); Jordi Torrelles, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/628,358

(22) Filed: Feb. 23, 2015

(65) Prior Publication Data

US 2015/0265696 A1  Sep. 24, 2015

Related U.S. Application Data

(62) Division of application No. 13/869,834, filed on Apr. 24, 2013, now Pat. No. 9,005,665.

(60) Provisional application No. 61/637,547, filed on Apr. 24, 2012.

(51) Int. Cl.

| | |
|---|---|
| A61K 39/12 | (2006.01) |
| A61K 39/385 | (2006.01) |
| C12N 7/00 | (2006.01) |
| A61K 39/39 | (2006.01) |
| A61K 9/14 | (2006.01) |
| A61K 35/74 | (2015.01) |
| C07K 16/10 | (2006.01) |
| A61K 35/76 | (2015.01) |
| A61K 39/00 | (2006.01) |
| B82Y 5/00 | (2011.01) |
| A61K 9/51 | (2006.01) |

(52) U.S. Cl.
CPC ............ *A61K 39/12* (2013.01); *A61K 9/14* (2013.01); *A61K 35/74* (2013.01); *A61K 35/76* (2013.01); *A61K 39/385* (2013.01); *A61K 39/39* (2013.01); *C07K 16/10* (2013.01); *C12N 7/00* (2013.01); *A61K 9/5153* (2013.01); *A61K 2039/5252* (2013.01); *A61K 2039/5258* (2013.01); *A61K 2039/541* (2013.01); *A61K 2039/543* (2013.01); *A61K 2039/545* (2013.01); *A61K 2039/552* (2013.01); *A61K 2039/55544* (2013.01); *A61K 2039/55555* (2013.01); *A61K 2039/55594* (2013.01); *A61K 2039/57* (2013.01); *A61K 2039/58* (2013.01); *A61K 2039/6018* (2013.01); *A61K 2039/6087* (2013.01); *A61K 2039/6093* (2013.01); *B82Y 5/00* (2013.01); *C12N 2770/10021* (2013.01); *C12N 2770/10034* (2013.01); *C12N 2770/10061* (2013.01); *C12N 2770/10071* (2013.01)

(58) Field of Classification Search
None
See application file for complete search history.

(56) References Cited

U.S. PATENT DOCUMENTS

| | | | |
|---|---|---|---|
| 5,695,766 A | 12/1997 | Paul | |
| 6,391,318 B1 | 5/2002 | Illum et al. | |
| 9,005,665 B2 * | 4/2015 | Gourapura | A61K 39/12 424/204.1 |
| 2011/0150770 A1 * | 6/2011 | Bautista | A61K 39/125 424/9.2 |
| 2015/0265696 A1 * | 9/2015 | Gourapura | A61K 39/12 424/499 |

FOREIGN PATENT DOCUMENTS

| | | |
|---|---|---|
| EP | 0385610 | 9/1990 |
| WO | 2013/163337 | 10/2013 |

OTHER PUBLICATIONS

Vanhee et al. (Veterinary Research. 2009; 40 (63): 1-15).*
Csaba et al. (Advanced Drug Delivery. 2009; 61: 140-157).*
Carcaboso et al. (Vaccine. 2004; 22: 1423-1432).*
Dwivedi et al. (Vaccine; 29: 4067-4076, available online Apr. 9, 2011).*
International Search Report and Written Opinion mailed Sep. 10, 2013 for PCT/US2013/038053, which was filed Apr. 24, 2013 and published as WO 2013/163337 on Oct. 31, 2013, 9 pages.
Adam et al., (1972) Isolation and properties of a macromolecular, water-soluble, immuno-adjuvant fraction from the cell wall of *Mycobacterium smegmatis*. Proc Natl Acad Sci U S A 69:851-854.
Adam et al., (1973) Preparation and biological properties of water-soluble adjuvant fractions from delipidated cells of *Mycobacterium smegmatis* and Nocardia opaca. Infect Immun 7:855-861.
Aguado et al., (1992) Controlled-release vaccines—biodegradable polylactide/polyglycolide (PL/PG) microspheres as antigen vehicles. Immunobiology 184:113-125.
Aiba S., (1992) Studies on chitosan: 4. Lysozymic hydrolysis of partially Nacetylated chitosans. Int J Biol Macromol 14:225-228.
Albina E., (1997) Epidemiology of porcine reproductive and respiratory syndrome (PRRS): an overview. Vet Microbiol 55(1-4):309-16.
Albina et al., (1998) Interferon-alpha response to swine arterivirus (PoAV), the porcine reproductive and respiratory syndrome virus. J Interferon Cytokine Res 18:485-490.
Allaoui-Attarki et al, (1997) Protective immunity against *Salmonella typhimurium* elicited in mice by oral vaccination with phosphorylcholine encapsulated in poly(DL-lactide-co-glycolide) microspheres. Infect Immun 65:853-857.

(Continued)

*Primary Examiner* — Shanon A Foley
(74) *Attorney, Agent, or Firm* — Meunier Carlin & Curfman LLC

(57) ABSTRACT

Disclosed herein are methods and compositions for treating or preventing Porcine reproductive and respiratory syndrome (PRRS) infection in a subject.

20 Claims, 38 Drawing Sheets

(56) References Cited

OTHER PUBLICATIONS

Amorij JP et al., (2012) Towards tailored vaccine delivery: Needs, challenges and perspectives. J Control Release 161(2):363-76.
Antonis et al., (2006) A novel recombinant virus-like particle vaccine for prevention of porcine parvovirus-induced reproductive failure. Vaccine 24(26):5481-90.
Arifuzzaman et al., (2012) Antigen-specific memory T cell responses after vaccination with an oral killed cholera vaccine in Bangladeshi children and comparison to responses in patients with naturally acquired cholera. Clin Vaccine Immunol 19(8):1304-11.
Azevedo et al., (2006) Cytokine responses in gnotobiotic pigs after infection with virulent or attenuated human rotavirus. J Virol 80(1):372-82.
Baras et al., (1999) Single-dose mucosal immunization with biodegradable microparticles containing a Schistosoma mansoni antigen. Infect Immun 67:2643-2648.
Barbe et al., (2010) Cytokines and acute phase proteins associated with acute swine influenza infection in pigs. Vet J 187(1): 48-53.
Bassaganya-Riera et al., (2004) Impact of immunizations with porcine reproductive and respiratory syndrome virus on lymphoproliferative recall responses of CD8+ T cells. Viral Immunol 17:25-37.
Basta et al., (2000) Porcine alveolar macrophages: poor accessory or effective suppressor cells for T-lymphocytes. Vet Immunol Immunopathol 77:177-190.
Belyaev et al., (1993) Development of baculovirus triple and quadruple expression vectors: co-expression of three or four bluetongue virus proteins and the synthesis of bluetongue virus-like particles in insect cells. Nucleic Acids Res 21(5):1219-23.
Benfield et al., (1992) Characterization of swine infertility and respiratory syndrome (SIRS) virus (isolate ATCC VR-2332). J Vet Diagn Invest 4:127-133.
Beyer et al., (2001) Bacterial carriers and virus-like-particles as antigen delivery devices: role of dendritic cells in antigen presentation. Curr Drug Targets Infect Disord 1(3):287-302.
Botner et al., (1997) Appearance of acute PRRS-like symptoms in sow herds after vaccination with a modified live PRRS vaccine. Vet Rec 141(19):497-9.
Brayden et al., (2005) Keynote review: intestinal Peyer's patch M cells and oral vaccine targeting. Drug Discov Today 10:1145-1157.
Cai et al., (2002) Restriction fragment length polymorphism of porcine reproductive and respiratory syndrome viruses recovered from Ontario farms, 1998-2000. J Vet Diagn Invest 14(4):343-47.
Cao et al., (1999) Delivering neuroactive molecules from biodegradable microspheres for application in central nervous system disorders. Biomaterials 20(4):329-39.
Caparros-Wanderley et al., (2004) Effect of dose and long-term storage on the immunogenicity of murine polyomavirus VP1 virus-like particles. Vaccine 22(3-4):352-61.
Carcaboso et al., (2004) Potent, long lasting systemic antibody levels and mixed Th1/Th2 immune response after nasal immunization with malaria antigen loaded PLGA microparticles. Vaccine 22:1423-1432.
Carpenter et al., (2005) Mucosal delivery of microparticle encapsulated ESAT-6 induces robust cell-mediated responses in the lung milieu. J Control Release 104:67-77.
Carrasco et al., (2002) Porcine dendritic cells generated in vitro: morphological, phenotypic and functional properties. Immunology 104:175-184.
Cavanagh D., (1997) Nidovirales: a new order comprising Coronaviridae and Arteriviridae. Arch Virol 142:629-633.
Chadwick et al., (2010) Nanotechnology solutions for mucosal immunization. Adv Drug Deliv Rev 62(4-5):394-407.
Charerntantanakul et al., (2006) Effects of porcine reproductive and respiratory syndrome virus-infected antigen-presenting cells on T cell activation and antiviral cytokine production. Viral Immunol 19:646-661.

Charerntantanakul W., (2009) Adjuvants for porcine reproductive and respiratory syndrome virus vaccines. Vet Immunol Immunopathol 129(1-2):1-13.
Chong et al., (2005) Enhancement of T helper type 1 immune responses against hepatitis B virus core antigen by PLGA nanoparticle vaccine delivery. J Control Release 102(1):85-99.
Christopher-Hennings et al., (1998) Identification of porcine reproductive and respiratory syndrome virus in semen and tissues from vasectomized and nonvasectomized boars. Vet Pathol 35(4):260-7.
Christopher-Hennings et al., (2001) Detection and duration of porcine reproductive and respiratory syndrome virus in semen, serum, peripheral blood mononuclear cells, and tissues from Yorkshire, Hampshire, and Landrace boars. J Vet Diagn Invest 13:133-142.
Collins et al., (1992) Isolation of swine infertility and respiratory syndrome virus (isolate ATCC VR-2332) in North America and experimental reproduction of the disease in gnotobiotic pigs. J Vet Diagn Invest 4:117-126.
Cox MM. (2008) Progress on baculovirus-derived influenza vaccines. Curr Opin Mol Ther 10(1):56-61.
Cozzi et al., (1997) Characterization of pigs transgenic for human decayaccelerating factor. Transplantation 64:1383-1392.
Diaz et al., (2005) Immune responses of pigs after experimental infection with a European strain of Porcine reproductive and respiratory syndrome virus. J Gen Virol 86(Pt 7):1943-51.
Didierlaurent et al., (2007) The impact of successive infections on the lung microenvironment. Immunology 122:457-465.
Doan et al., (2005) Virus-like particles as HIV-1 vaccines. Rev Med Virol 15(2):75-88.
Done et al., (1995) Porcine reproductive and respiratory syndrome: clinical disease, pathology and immunosuppression. Vet Rec 136:32-35.
Duncan, R., (2005) Nanomedicine gets clinical. Materials Today 8:16-7.
Dwivedi et al., (2009) Adjuvanticity and protective immunity of Plasmodium yoelii nigeriensis blood-stage soluble antigens encapsulated in fusogenic liposome. Vaccine 27:473-482.
Dwivedi et al., (2011) Cross-protective immunity to porcine reproductive and respiratory syndrome virus by intranasal delivery of a live virus vaccine with a potent adjuvant. Vaccine 29:4058-4066.
Dwivedi et al., (2011) Intranasal delivery of whole cell lysate of Mycobacterium tuberculosis induces protective immune responses to a modified live porcine reproductive and respiratory syndrome virus vaccine in pigs. Vaccine 29: 4067-4076.
Dwivedi et al., (2012) Biodegradable Nanoparticle-Entrapped Vaccine Induces Cross-Protective Immune Response against a Virulent Heterologous Respiratory Viral Infection in Pigs. PLoS One 7(12):e51794.
Dwivedi et al., (2012) Evaluation of immune responses to porcine reproductive and respiratory syndrome virus in pigs during early stage of infection under farm conditions. Virol J 9:45.
Dybing et al., (1997) Expression of MD infectious bursal disease viral proteins in baculovirus. Avian Dis 41(3):617-26.
Dybing et al., (1998) Antigenic and immunogenic properties of baculovirus expressed infectious bursal disease viral proteins. Avian Dis 42(1):80-91.
Eldridge et al., (1989) Biodegradable microspheres: vaccine delivery system for oral immunization. Curr Top Microbiol Immunol 146:59-66.
Fang et al., (2004) Heterogeneity in Nsp2 of European-like porcine reproductive and respiratory syndrome viruses isolated in the United States. Virus Res 100(2):229-35.
Fang et al., (2006) A full-length cDNA infectious clone of North American type 1 porcine reproductive and respiratory syndrome virus: expression of green fluorescent protein in the Nsp2 region. J Virol 80:11447-11455 56.
Fang et al., (2008) Development of genetic markers in the nonstructural protein 2 region of a US type 1 porcine reproductive and respiratory syndrome virus: implications for future recombinant marker vaccine development. J Gen Virol 89:3086-3096.
Fausch et al., (2003) Differential uptake and cross-presentation of human papillomavirus virus-like particles by dendritic cells and Langerhans cells. Cancer Res 63(13):3478-82.

(56) References Cited

OTHER PUBLICATIONS

Ferreira et al., (1995) The assessment of antibody affinity distribution by thiocyanate elution: a simple dose-response approach. *J Immunol Methods* 187:297-305

French et al., (1990) Synthesis of bluetongue virus (BTV) corelike particles by a recombinant baculovirus expressing the two major structural core proteins of BTV. *J Virol* 64(4):1530-6.

French et al., (1990) Assembly of double-shelled, viruslike particles of bluetongue virus by the simultaneous expression of four structural proteins. *J Virol* 64(12):5695-700.

Ganter et al., (1997) Cellular variables in bronchoalveolar lavage fluids (BALF) in selected healthy pigs. *Res Vet Sci* 63:215-217.

Gomez-Laguna et al., (2009) Changes in lymphocyte subsets and cytokines during European porcine reproductive and respiratory syndrome: increased expression of IL-12 and IL-10 and proliferation of CD4(−)CD8(high). *Viral Immunol* 22(4):261-71.

Gourapura, (2013) Development of novel mucosal vaccines for the control of PRRSV outbreaks. 09-213. Ohio State University, pp. 1-14.

Greenway et al., (1998) Induction of protective immune responses against Venezuelan equine encephalitis (VEE) virus aerosol challenge with microencapsulated VEE virus vaccine. *Vaccine* 16:1314-1323.

Grumelli et al., (2004) An immune basis for lung parenchymal destruction in chronic obstructive pulmonary disease and emphysema. *PLoS Med* 1(1):e8.

Guermonprez et al., (2002) Antigen presentation and T cell stimulation by dendritic cells. *Annu Rev Immunol* 20:621-667.

Guillonneau et al., (2009) Combined NKT cell activation and influenza virus vaccination boosts memory CTL generation and protective immunity. *Proc Natl Acad Sci USA* 106(9):3330-5.

Guo et al., (2004) Protection of pigs against Taenia solium cysticercosis using recombinant antigen or in combination with DNA vaccine. *Vaccine* 22(29-30):3841-7.

Gupta et al., (1998) Biodegradable polymer microspheres as vaccine adjuvants and delivery systems. *Dev Biol Stand* 92:63-78.

Gupta et al., (2006) Lectin anchored stabilized biodegradable nanoparticles for oral immunization 1. Development and in vitro evaluation. *Int J Pharm* 318(1-2):163-73.

Halbur et al., (1995) Immunohistochemical identification of porcine reproductive and respiratory syndrome virus (PRRSV) antigen in the heart and lymphoid system of three-week-old colostrum-deprived pigs. *Vet Pathol* 32:200-204.

Heegaard et al., (2011) Adjuvants and delivery systems in veterinary vaccinology: current state and future developments. *Arch Virol* 156(2):183-202.

Hein et al., (2003) A road less travelled: large animal models in immunological research. *Nat Rev Immunol* 3:79-84.

Heit et al., (2007) Antigen co-encapsulated with adjuvants efficiently drive protective T cell immunity. *Eur J Immunol* 37:2063-2074.

Hernandez-Pando et al., (2008) Orally administered *Mycobacterium vaccae* modulates expression of immunoregulatory molecules in BALB/c mice with pulmonary tuberculosis. *Clin Vaccine Immunol* 15:1730-1736.

Holmgren et al., (1992) Mucosal immunity: implications for vaccine development. *Immunobiology* 184:157-179.

Holtkamp et al., (2011) PRRS Costs Industry $664 Million Annually. Pork Checkoff Study, (http://www.pork.org/News/1265/PRRSCostsIndustry664Million.aspx).

Ibrahim et al., (2006) Selected physiologic compatibilities and incompatibilities between human and porcine organ systems. *Xenotransplantation* 13:488-499.

Inaba et al., (1993) Dendritic cell progenitors phagocytose particulates, including bacillus Calmette-Guerin organisms, and sensitize mice to mycobacterial antigens in vivo. *J Exp Med* 178:479-488.

Ito et al., (2008) Factors affecting the loading efficiency of water-soluble drugs in PLGA microspheres. *Colloids Surf B Biointerfaces* 61(1):25-9.

Janes et al., (2001) Chitosan nanoparticles as delivery systems for doxorubicin. *J Control Release* 73:255-267.

Jung et al., (2007) Altered pathogenesis of porcine respiratory coronavirus in pigs due to immunosuppressive effects of dexamethasone: implications for corticosteroid use in treatment of severe acute respiratory syndrome coronavirus. *J Virol* 81:13681-13693.

Jung et al., (2009) Porcine 159. reproductive and respiratory syndrome virus modifies innate immunity and alters disease outcome in pigs subsequently infected with porcine respiratory coronavirus: implications for respiratory viral co-infections. *J Gen Virol* 90:2713-2723.

Kamijuku et al., (2008) Mechanism of NKT cell activation by intranasal coadministration of alpha-galactosylceramide, which can induce cross-protection against influenza viruses. *Mucosal Immunol* 1(3):208-18.

Kaplan et al., (1996) Impaired IL-12 responses and enhanced development of Th2 cells in Stat4-deficient mice. *Nature* 382(6587):174-7.

Khatri et al., (2010) Swine influenza H1N1 virus induces acute inflammatory immune responses in pig lungs: a potential animal model for human H1N1 influenza virus. *J Virol* 84:11210-11218.

Kim et al., (2002) Mucosal immune responses following oral immunization with rotavirus antigens encapsulated in alginate microspheres. *J Control Release* 85(1-3):191-202.

Kim et al., (2007) Effect of genotypic and biotypic differences among PRRS viruses on the serologic assessment of pigs for virus infection. *Vet Microbiol* 123:1-14.

Kimman et al., (2009) Challenges for porcine reproductive and respiratory syndrome virus (PRRSV) vaccinology. *Vaccine* 27(28):3704-18.

Kugathasan et al., (2008) CD11c+ antigen presenting cells from the alveolar space, lung parenchyma and spleen differ in their phenotype and capabilities to activate naive and antigen-primed T cells. *BMC Immunol* 9:48.

Kuroki et al., (2003) Streptococcal preparation OK-432: a new maturation factor of monocyte-derived dendritic cells for clinical use. *Cancer Immunol Immunother* 52:561-568.

Labarque et al., (2000) Effect of cellular changes and onset of humoral immunity on the replication of porcine reproductive and respiratory syndrome virus in the lungs of pigs. *J Gen Virol* 81(Pt 5):1327-34.

Lamm, M. E., (1976) Cellular aspects of immunoglobulin A. *Adv Immunol* 22:223-290.

Latham et al., (2001) Formation of wild-type and chimeric influenza virus-like particles following simultaneous expression of only four structural proteins. *J Virol* 75(13):6154-65.

Lederer et al., (1975) Cell walls of Mycobacteria and related organisms; chemistry and immunostimulant properties. *Mol Cell Biochem* 7:87-104.

Leroith et al., (2011) A modified live PRRSV vaccine and the pathogenic parent strain induce regulatory T cells in pigs naturally infected with Mycoplasma hyopneumoniae. *Vet Immunol Immunopathol* 140:312-316.

Li et al., (2009) Recombination in vaccine and circulating strains of porcine reproductive and respiratory syndrome viruses. *Emerg Infect Dis* 15(12):2032-5.

Li et al., (2010) Genomic analysis of two Chinese strains of porcine reproductive and respiratory syndrome viruses with different virulence. *Virus Genes* 40(3):374-81.

Liew et al., (1984) Cross-protection in mice infected with influenza A virus by the respiratory route is correlated with local IgA antibody rather than serum antibody or cytotoxic T cell reactivity. *Eur J Immunol* 14(4):350-6.

Ling et al., (2008) Structural constraints for the binding of short peptides to claudin-4 revealed by surface plasmon resonance. *J Biol Chem* 283(45):30585-95.

Lizeng et al., (2004) Potent neutralizing serum immunoglobulin A (IgA) in human immunodeficiency virus type 2-exposed IgG-seronegative individuals. *J Virol* 78:7016-7022.

Lopez et al., (2004) Role of neutralizing antibodies in PRRSV protective immunity. *Vet Immunol Immunopathol* 102(3):155-63.

(56) References Cited

OTHER PUBLICATIONS

Loving et al., (2007) Differential type I interferon activation and susceptibility of dendritic cell populations to porcine arterivirus. *Immunology* 120:217-229.
Lycke, N., (2012) Recent progress in mucosal vaccine development: potential and limitations. *Nat Rev Immunol* 12(8):592-605.
Ma et al., (2012) PLGA nanoparticle mediated delivery of tumor antigenic peptides elicits effective immune responses. *Int J Nanomedicine* 7:1475-87.
Madsen et al., (1998) Sequence analysis of porcine reproductive and respiratory syndrome virus of the American type collected from Danish swine herds. *Arch Virol* 143(9):1683-700.
Manickam et al., (2012) Porcine reproductive and respiratory syndrome virus induces pronounced immune modulatory responses at mucosal tissues in the parental vaccine strain VR2332 infected pigs. *Vet Microbiol* 162(1): 68-77.
Mann et al., (2009) Delivery systems: a vaccine strategy for overcoming mucosal tolerance? *Expert Rev Vaccines* 8(1):103-12.
Manocha et al., (2005) Enhanced mucosal and systemic immune response with intranasal immunization of mice with HIV peptides entrapped in PLG microparticles in combination with Ulex Europaeus-I lectin as M cell target. *Vaccine* 23(48-49):5599-617.
Maranga et al., (2002) Large scale production and downstream processing of a recombinant porcine parvovirus vaccine. *Appl Microbiol Biotechnol* 59(1):45-50.
Martelli et al., (2009) Efficacy of a modified live porcine reproductive and respiratory syndrome virus (PRRSV) vaccine in pigs naturally exposed to a heterologous European (Italian cluster) field strain: Clinical protection and cell-mediated immunity. *Vaccine* 27(28):3788-99.
Maruyama et al., (1997) Nanoparticle DNA carrier with poly(L-lysine) grafted polysaccharide copolymer and poly(D,L-lactic acid). *Bioconjug Chem* 8:735-742.
Mateu et al., (2008) the challenge of PRRS immunology. *Vet J* 177:345-351.
McGhee et al., (1992) The mucosal immune system: from fundamental concepts to vaccine development. *Vaccine* 10:75-88.
McNeil, SE., (2005) Nanotechnology for the biologist. *J Leukoc Biol* 78(3):585-94.
Meier et al., (2003) Gradual development of the interferon-gamma response of swine to porcine reproductive and respiratory syndrome virus infection or vaccination. *Virology* 309(1):18-31.
Mengeling et al., (2002) The potential role of genetic recombination in the evolution of new strains of porcine reproductive and respiratory syndrome virus (PRRSV). *J Swine Health Prod* 10:273-5.
Mengeling et al., (2003) Strain specificity of the immune response of pigs following vaccination with various strains of porcine reproductive and respiratory syndrome virus. *Vet Microbiol* 93:13-24.
Mestecky et al., (1987) Immunoglobulin A (IgA): molecular and cellular interactions involved in IgA biosynthesis and immune response. *Adv Immunol* 40:153-245.
Mestecky et al., (1997) Routes of immunization and antigen delivery systems for optimal mucosal immune responses in humans. *Behring Inst Mitt*:33-43.
Meulenberg, J. J., (2000) PRRSV, the virus. *Vet Res* 31:11-21.
Miyake et al., (2004) Induction of HIV-specific antibody response and protection against vaginal SHIV transmission by intranasal immunization with inactivated SHIV-capturing nanospheres in macaques. *J Med Virol* 73:368-377.
Moghimi et al., (2003) Stealth liposomes and long circulating nanoparticles: critical issues in pharmacokinetics, opsonization and protein-binding properties. *Prog Lipid Res* 42(6):463-78.
Mukherjee et al., (2008) Preparation, characterization and in-vitro evaluation of sustained release protein-loaded nanoparticles based on biodegradable polymers. *Int J Nanomedicine* 3(4):487-96.
Murata et al., (2003) Immunization with hepatitis C virus-like particles protects mice from recombinant hepatitis C virus-vaccinia infection. *Proc Natl Acad Sci USA* 100(11):6753-8.
Murtaugh et al., (2002) Genetic interaction between porcine reproductive and respiratory syndrome virus (PRRSV) strains in cell culture and in animals. *J Swine Health Prod* 10:15-21.
Nagao et al., (2011) Role of lipid rafts in innate immunity and phagocytosis of polystyrene latex microspheres. *Colloids Surf B Biointerfaces* 84:317-324.
Nateghi et al., (2010) Immune response of BALB/c mice against an experimental vaccine of Alum precipitated autoclaved Leishmania major (Alum-ALM) mixed with BCG or *Mycobacterium vaccae*. *Trop Biomed* 27:89-102.
Nayak et al., (2009) Formulation, characterization and evaluation of rotavirus encapsulated PLA and PLGA particles for oral vaccination. *J Microencapsul* 26(2):154-65.
Nielsen et al., (2001) Reversion of a live porcine reproductive and respiratory syndrome virus vaccine investigated by parallel mutations. *J Gen Virol* 82:1263-1272.
Nielsen et al., (2002) Experimental inoculation of late term pregnant sows with a field isolate of porcine reproductive and respiratory syndrome vaccine-derived virus. *Vet Microbiol* 84(1-2):1-13.
Nixon et al., (1996) Synthetic peptides entrapped in microparticles can elicit cytotoxic T cell activity. *Vaccine* 14(16):1523-30.
Nobs et al., (2004) Current methods for attaching targeting ligands to liposomes and nanoparticles. *J Pharm Sci* 93:1980-1992.
Ogra et al., (1969) Distribution of poliovirus antibody in serum, nasopharynx and alimentary tract following segmental immunization of lower alimentary tract with poliovaccine. *J Immunol* 102:1423-1430.
O'Hagan et al., (1991) Biodegradable microparticles as controlled release antigen delivery systems. *Immunol* 73(2):239-42.
Olin et al., (2005) Gammadelta lymphocyte response to porcine reproductive and respiratory syndrome virus. *Viral Immunol* 18:490-499.
Olin et al., (2005) Gammadelta T-lymphocyte cytotoxic activity against *Mycobacterium bovis* analyzed by flow cytometry. *J Immunol Methods* 297(1-2):1-11.
Osorio et al., (2002) Passive transfer of virus-specific antibodies confers protection against reproductive failure induced by a virulent strain of porcine reproductive and respiratory syndrome virus and establishes sterilizing immunity. *Virology* 302(1):9-20.
Paliard et al., (2000) Priming of strong, broad, and long-lived HIV type 1 p55gag-specific CD8+ cytotoxic T cells after administration of a virus-like particle vaccine in rhesus macaques. *AIDS Res Hum Retroviruses* 16(3):273-82.
Paolicelli et al., (2010) Surface-modified PLGA-based nanoparticles that can efficiently associate and deliver virus-like particles. *Nanomedicine* (Lond) 5(6):843-53.
Piotrowicz, A., (2005) Incorporation of microspheres into nerve guidance channels for drug delivery purposes. *Appl Chem and Chem Engineering, Univ of Toronto, Toronto*: p. 108.
Piras et al., (2005) Porcine reproductive and respiratory syndrome (PRRS) virusspecific interferon-gamma(+) T-cell responses after PRRS virus infection or vaccination with an inactivated PRRS vaccine. *Viral Immunol* 18:381-389.
Plummer et al., (2010) Viral nanoparticles and virus-like particles: platforms for contemporary vaccine design. *Wiley Interdiscip Rev Nanomed Nanobiotechnol* 3:174-196.
Rajapaksa et al., (2010) Intranasal M cell uptake of nanoparticles is independently influenced by targeting ligands and buffer ionic strength. *J Biol Chem* 285:23739-23746.
Rawat et al., (2008) Inhalable large porous microspheres of low molecular weight heparin: in vitro and in vivo evaluation. *J Control Release* 128(3):224-32.
Read et al., (2000) Cytotoxic T lymphocyte-associated antigen 4 plays an essential role in the function of CD25(+)CD4(+) regulatory cells that control intestinal inflammation. *J Exp Med* 192(2):295-302.
Reischl et al., (2009) Drug delivery of siRNA therapeutics: potentials and limits of nanosystems. *Nanomedicine* 5(1):8-20.
Renegar et al., (1991) Immunoglobulin A mediation of murine nasal antiinfluenza virus immunity. *J Virol* 65:2146-2148.
Renegar et al., (1991) Passive transfer of local immunity to influenza virus infection by IgA antibody. *J Immunol* 146:1972-1978.

(56) References Cited

OTHER PUBLICATIONS

Renukaradhya et al., (2010) Porcine reproductive and respiratory syndrome virus-induced immunosuppression exacerbates the inflammatory response to porcine respiratory coronavirus in pigs. *Viral Immunol* 23:457-466.

Renukaradhya et al., (2012) Mucosal vaccines to prevent porcine reproductive and respiratory syndrome: a new perspective. *Animal Health Research Review* 13:1-17 doi:10.1017/S1466252312000023.

Rogers et al., (2008) The porcine lung as a potential model for cystic fibrosis. *Am J Physiol Lung Cell Mol Physiol* 295:L240-263.

Rossow et al. (1994) Experimental porcine reproductive and respiratory syndrome virus infection in one-, four-, and 10-week-old pigs. *J Vet Diagn Invest* 6(1):3-12.

Rossow et al., (1996) Chronological immunohistochemical detection and localization of porcine reproductive and respiratory syndrome virus in gnotobiotic pigs. *Vet Pathol* 33(5):551-6.

Rowland, R. R. (2010) The interaction between PRRSV and the late gestation pig fetus. *Virus Res* 154:114-122.

Roy et al., (2008) Virus-like particles as a vaccine delivery system: myths and facts. *Hum Vaccine* 4(1):5-12.

Rudin et al., (1999) Antibody responses in the lower respiratory tract and male urogenital tract in humans after nasal and oral vaccination with cholera toxin B subunit. *Infect Immun* 67:2884-2890.

Ryan et al., (2001) Immunomodulators and delivery systems for vaccination by mucosal routes. *Trends Biotechnol* 19:293-304.

Saini et al., (2011) Comparison of humoral and cell-mediated immune responses to cationic PLGA microspheres containing recombinant hepatitis B antigen. *Int J Pharm* 408(1-2):50-7.

Sakaguchi et al., (2009) Regulatory T cells: how do they suppress immune responses? *Int Immunol* 21(10):1105-11.

Schaumann et al., (2004) Metal-rich ambient particles (particulate matter 2.5) cause airway inflammation in healthy subjects. *Am J Respir Crit Care Med* 170:898-903.

Schirmbeck et al., (1996) Virus-like particles induce MHC class I-restricted Tcell responses. Lessons learned from the hepatitis B small surface antigen. *Intervirology* 39(1-2):111-9.

Schliehe et al., (2011) CD8-dendritic cells and macrophages cross-present poly(D,L-lactate-co-glycolate) acid microsphere encapsulated antigen in vivo. *J Immunol* 187(5):2112-21.

Scortti et al., (2007) Failure of an inactivated vaccine against porcine reproductive and respiratory syndrome to protect gilts against a heterologous challenge with PRRSV. *Vet Record* 161:809-813.

Sedgmen et al., (2004) Alternative routes of mucosal immunization in large animals. *Immunol Cell Biol* 82:10-16.

Semete et al., (2010) In vivo evaluation of the biodistribution and safety of PLGA nanoparticles as drug delivery systems. *Nanomedicine* 6(5):662-71.

Shahin et al., (1995) Adjuvanticity and protective immunity elicited by Bordetella pertussis antigens encapsulated in poly(DL-lactide-co-glycolide) microspheres. *Infect Immun* 63:1195-1200.

Shephard et al., (2003) Immunogenicity of bovine parainfluenza type 3 virus proteins encapsulated in nanoparticle vaccines, following intranasal administration to mice. *Res Vet Sci* 74:187-190.

Shibata et al., (1997) Alveolar macrophage priming by intravenous administration of chitin particles, polymers of N-acetyl-D-glucosamine, in mice. *Infect Immun* 65:1734-1741.

Singh et al., (2001) A novel bioadhesive intranasal delivery system for inactivated influenza vaccines. *J Control Release* 70:267-276.

Singla et al., (2001) Chitosan: some pharmaceutical and biological aspects—an update. *J Pharm Pharmacol* 53:1047-1067.

Spellberg et al., (2001) Type 1/Type 2 immunity in infectious diseases. *Clin Infect Dis* 32(1):76-102.

Storgaard et al., (1999) Examination of the selective pressures on a live PRRS vaccine virus. *Arch Virol* 144:2389-2401.

Su et al., (2008) Effect of the shuffled porcine IL-2 gene and CpG matifs on immune responses to procine pseudorabies inactivated vaccine. *Chinese Vet Sci* [Abstract only].

Suradhat et al., (2003) Upregulation of IL-10 gene expression in porcine peripheral blood mononuclear cells by porcine reproductive and respiratory syndrome virus. *J Gen Virol* 84:453-459.

Takayama et al., (1975) Site of inhibitory action of isoniazid in the synthesis of mycolic acids in Mycobacterium tuberculosis. *J Lipid Res* 16:308-317.

TG P., (1994) Degradation of poly(D,L-lactic acid) microspheres effect of molecular weight. *J Control Release* 30:161-173.

Thacker et al., (2000) Effect of vaccination on the potentiation of porcine reproductive and respiratory syndrome virus (PRRSV)-induced pneumonia by Mycoplasma hyopneumoniae. *Vaccine* 18:1244-1252.

Thanawongnuwech et al., (2001) Differential production of proinflammatory cytokines: in vitro PRRSV and Mycoplasma hyopneumoniae co-infection model. *Vet Immunol Immunopathol* 79:115-127.

Thomas et al., (2009) Influence of surface charge of PLGA particles of recombinant hepatitis B surface antigen in enhancing systemic and mucosal immune responses. *Int J Pharm* 379(1): 41-50.

Thomas et al., (2011) Aerosolized PLA and PLGA Nanoparticles Enhance Humoral, Mucosal and Cytokine Responses to Hepatitis B Vaccine. *Mol Pharm* 8:405-415.

Thomassen et al., (2007) ABCG1 is deficient in alveolar macrophages of GMCSF knockout mice and patients with pulmonary alveolar proteinosis. *J Lipid Res* 48:2762-2768.

Thompson et al., (2012) Maximal adjuvant activity of nasally delivered IL-1alpha requires adjuvant-responsive CD11c(+) cells and does not correlate with adjuvant-induced in vivo cytokine production. *J Immunol* 188(6):2834-46.

van der Lubben et al,. (2001) Chitosan and its derivatives in mucosal drug and vaccine delivery. *Eur J Pharm Sci* 14:201-207.

van der Lubben et al., (2001) Chitosan for mucosal vaccination. *Adv Drug Deliv Rev* 52:139-144.

Van Reeth et al., (1999) Differential production of proinflammatory cytokines in the pig lung during different respiratory virus infections: correlations with pathogenicity. *Res Vet Sci* 67(1):47-52.

Van Reeth et al., (2002) In vivo studies on cytokine involvement during acute viral respiratory disease of swine: troublesome but rewarding. *Vet Immunol Immunopathol* 87(3-4):161-8.

VanCott et al., (1993) Isotype-specific antibody-secreting cells to transmissible gastroenteritis virus and porcine respiratory coronavirus in gut- and bronchusassociated lymphoid tissues of suckling pigs. *J Immunol* 150(9):3990-4000.

Vanhee et al., (2009) Development of an experimental inactivated PRRSV vaccine that induces virus-neutralizing antibodies. *Vet Res* 40:63 pp. 1-15.

Vila et al., (2004) Low molecular weight chitosan nanoparticles as new carriers for nasal vaccine delivery in mice. *Eur J Pharm Biopharm* 57:123-131.

Voicu et al., (1994) Interaction of porcine reproductive and respiratory syndrome virus with swine monocytes. *Vet Rec* 134(16):422-3.

Wagstrom et al., (2001) Shedding of porcine reproductive and respiratory syndrome virus in mammary gland secretions of sows. *Am J Vet Res* 62(12):1876-80.

Wang et al., (2011) Immune responses in piglets infected with highly pathogenic porcine reproductive and respiratory syndrome virus. *Vet Immunol Immunopathol* 142(3-4):170-8.

Wasilk et al., (2004) Detection of U.S., Lelystad, and European-like porcine reproductive and respiratory syndrome viruses and relative quantitation in boar semen and serum samples by real-time PCR. *J Clin Microbiol* 42:4453-4461.

Waters et al., (1999) Systemic and mucosal immune responses of pigs to parenteral immunization with a pepsin-digested Serpulina hyodysenteriae bacterin. *Vet Immunol Immunopathol* 69(1):75-87.

Welsh et al., (1997) Alpha beta and gamma delta T-cell networks and their roles in natural resistance to viral infections. *Immunol Rev* 159:79-93.

Wesley et al., (1999) Evidence for divergence of restriction fragment length polymorphism patterns following in vivo replication of porcine reproductive and respiratory syndrome virus. *Am J Vet Res* 60:463-467.

(56) References Cited

OTHER PUBLICATIONS

Wilkinson et al., (2000) Enhancement of the human T cell response to culture filtrate fractions of *Mycobacterium tuberculosis* by microspheres. *J Immunol Methods* 235:1-9.

Wills et al., (1997) Porcine reproductive and respiratory syndrome virus: a persistent infection. *Vet Microbiol* 55:231-240.

Wong et al., (1994) Enhanced protection against respiratory influenza A infection in mice by liposome-encapsulated antibody. *Immunology* 81:280-284.

Wongyanin et al., (2010) Induction of inducible CD4+CD25+Foxp3+ regulatory T lymphocytes by porcine reproductive and respiratory syndrome virus (PRRSV). *Vet Immunol Immunopathol* 133(2-4):170-82.

Xiao et al., (2004) The level of virus-specific T-cell and macrophage recruitment in porcine reproductive and respiratory syndrome virus infection in pigs is independent of virus load. *J Virol* 78(11):5923-33.

Yoshida et al., (2006) Differential effects of agarose and poly(lactic-co-glycolic acid) on dendritic cell maturation. *J Biomed Mater Res A* 79(2):393-408.

Zhang et al., (2007) Intranasal administration of CpG oligonucleotides induces mucosal and systemic Type 1 immune responses and adjuvant activity to porcine reproductive and respiratory syndrome killed virus vaccine in piglets in vivo. *Int Immunopharmacol* 7(13):1732-40.

Zimmerman J., (2003) PRRS Virus—What Happens After a Pig Becomes Infected with PRRS Virus? 2003 PRRS Compendium Producer Edition, Chapter V (National Pork Board, Des Moines, Iowa):36-43.

Zuckermann FA., (1999) Extrathymic CD4/CD8 double positive T cells. *Vet Immunol Immunopathol* 72(1-2):55-66.

Zuckermann FA., (2007) Assessment of the efficacy of commercial porcine reproductive and respiratory syndrome virus (PRRSV) vaccines based on measurement of serologic response, frequency of gamma-IFN-producing cells and virological parameters of protection upon challenge. *Vet Microbiol* 123:69-85.

\* cited by examiner

Dilution of control PRRSV or pig lung homogenates

| | $10^{-1}$ | $10^{-2}$ | $10^{-3}$ | $10^{-4}$ | $10^{-5}$ | $10^{-6}$ | $10^{-7}$ |
|---|---|---|---|---|---|---|---|
| (A) | | | | | | | |
| (B) | | | | | | | |
| (C) | | | | | | | |
| (D) | | | | | | | |
| (E) | | | | | | | |
| (F) | | | | | | | |
| (G) | | | | | | | |
| (H) | | | | | | | |

A: Negative control
B: Virus / Positive Control
C: Mock pig sample
D: Mock + Chal.

E: PRRSV-K-Ag + Chal.
F: PRRSV-K-Ag with Mtb WCL + Chal.
G: Both PRRSV-K-Ag & Mtb WCL in NP + Chal.
H: NP-PRRSV-K-Ag with Mtb WCL + Chal.

Fig 21.

Schematic of anti-PRRSV immunity in pigs vaccianted intranasally with PLGA Nanoparticle-entrapped PRRSV vaccine and challenged with a heterologous virus

- IgG and IgA
- Antibody Avidity
- VNT titer
- IFN-γ secreting cells
- Unvaccinated+ PRRSV Chal
- Nano-PRRSV vaccine + Chal Vacc! Boost PC 0 PC 6 PC 10 PC 15

PRRSV challenge

Fig. 23

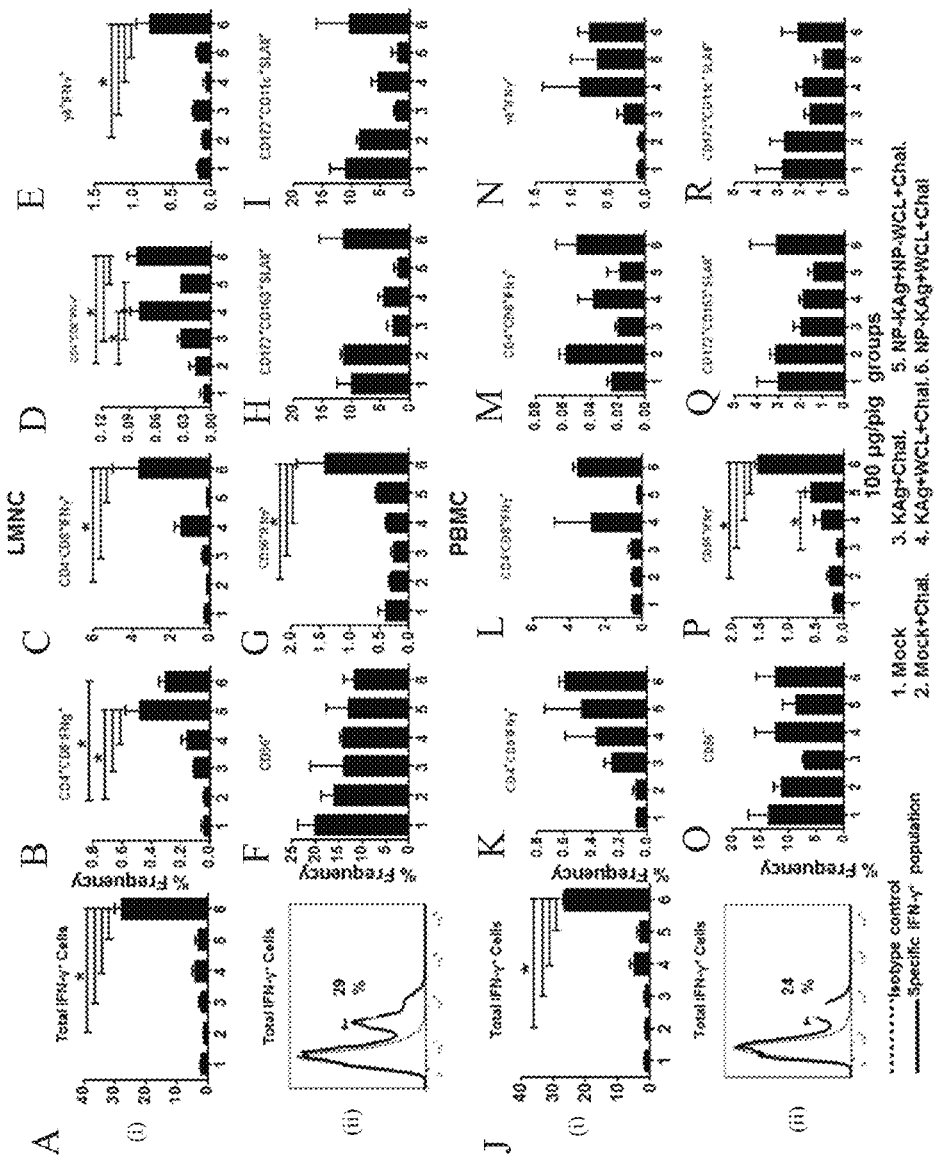
FIG. 28A, FIG. 28B, FIG. 28C, FIG. 28D, FIG. 28E, FIG. 28F, FIG. 28G, FIG. 28H, FIG. 28I, FIG. 28J, FIG. 28K, FIG. 28L, FIG. 28M, FIG. 28N, FIG. 28O, FIG. 28P, FIG. 28Q, FIG. 28R

FIG. 30A, FIG. 30B, FIG. 30C, FIG. 30D, FIG. 30E, FIG. 30F

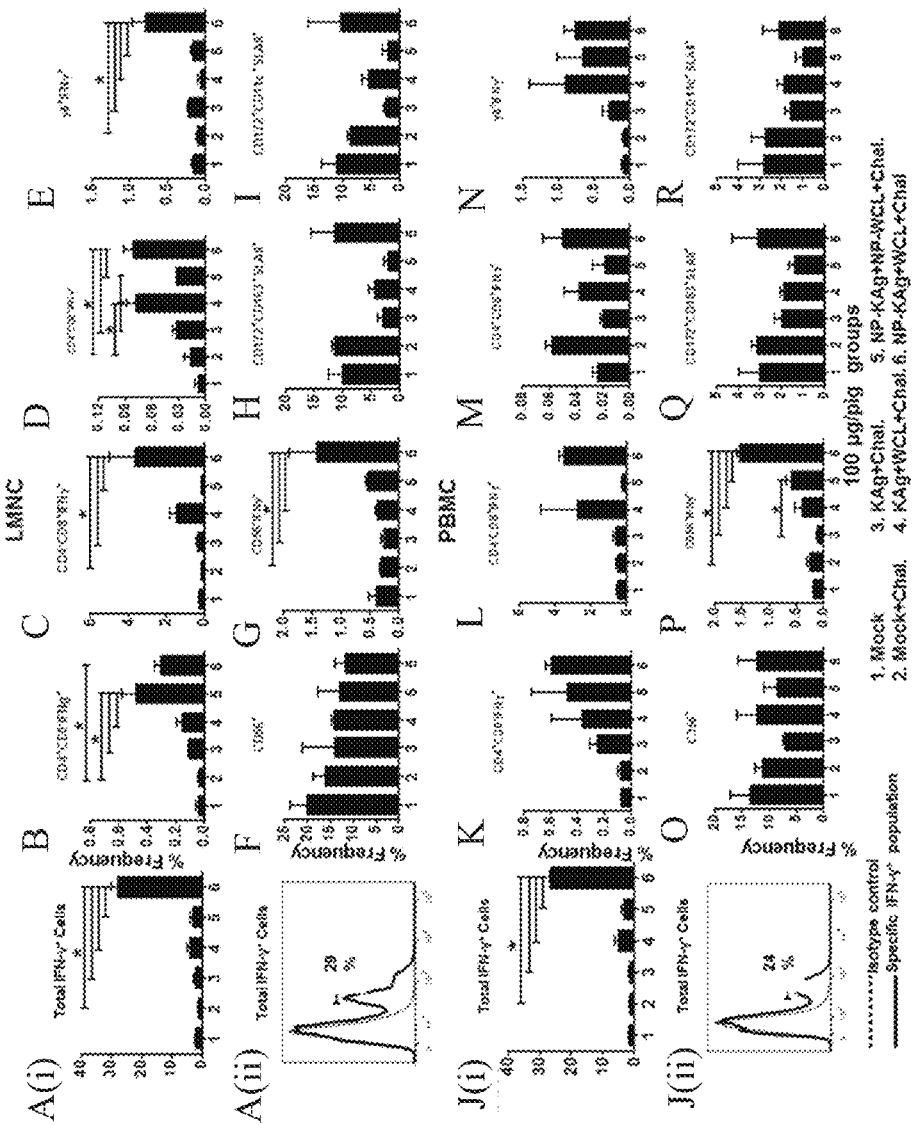
FIG. 34A, FIG. 34B, FIG. 34C, FIG. 34D, FIG. 34E, FIG. 34F, FIG. 34G, FIG. 34H, FIG. 34I, FIG. 34J, FIG. 34K, FIG. 34L, FIG. 34M, FIG. 34N, FIG. 34O, FIG. 34P, FIG. 34Q, FIG. 34R

A   PRRSV in lung lysate

100 µg/pig dose    500 µg/pig dose y-axis: $TCID_{50}$/gm of lung (log10)

B   PRRSV in blood

100 µg/pig dose    500 µg/pig dose y-axis: $TCID_{50}$/ml of serum (log10)

x-axis: Post challenge days becfdg    edg    dg

○ /1. Mock         □ /3. KAg+Chal.         ▽ /5. PLGA-NanoPRRS+NP-*M.tb* WCL+Chal.
● /2. Mock+Chal.   ■ /4. KAg+*M.tb* WCL+Chal.   ✦ /6. PLGA-NanoPRRS+*M.tb* WCL+Chal.

FIG. 35A, FIG. 35B

COMPOSITIONS AND METHODS FOR TREATING AND PREVENTING PORCINE REPRODUCTIVE AND RESPIRATORY SYNDROME

CROSS-REFERENCE TO RELATED APPLICATIONS

This application is a divisional of and claims priority to U.S. patent application Ser. No. 13/869,834, filed Apr. 24, 2013, entitled "Compositions and Methods for Treating and Preventing Porcine Reproductive and Respiratory Syndrome," which claims benefit of U.S. Provisional Application No. 61/637,547, filed Apr. 24, 2012, both of which are hereby incorporated herein by reference in their entirety.

BACKGROUND

Porcine reproductive and respiratory syndrome (PRRS) is a chronic viral disease of pigs worldwide. PRRS is endemic in most pork-producing countries, and it is responsible for major economic losses to the swine industry, with an estimated annual loss of $664 million in the US (8).

Since the late 1990s, modified live PRRSV (PRRS-MLV) and killed virus vaccines have been available to control the disease, but neither of them protects pigs completely against heterologous field viruses (27). Like the field virus, PRRS-MLV also induces immunosuppression (29, 30). Moreover, there are several reports of reversion of vaccine virus into virulence leading to severe disease outbreaks (31-34). Although killed PRRSV vaccines are safe, they are poorly immunogenic (35, 36).

Clinical signs of PRRS comprise respiratory and reproductive dysfunction and the causal agent is PRRS virus (PRRSV) (28). PRRSV establishes disease by modulating the pig immune system from as early as two days and continues for several weeks post-infection (14, 15). A particular challenge presented by PRRSV is the immunosuppression caused by PRRSV attributed to virus mediated reduction in production of important cytokines (IFN-α, IFN-γ, and TNF-α), associated with increased secretion of interleukin (IL)-10 and transforming growth factor-β (TGF-β), and upregulation of Foxp3$^+$ T-regulatory cell (Tregs) population (14). In addition, in infected pigs, virus neutralizing (VN) antibodies appear delayed (3-4 weeks) and also their levels remain low (86). Thus, there remains a great need in the art to provide for safe and effective protection and treatment of PRRS.

BRIEF DESCRIPTION OF THE SEVERAL VIEWS OF THE DRAWINGS

FIG. 1 shows: (A) Morphology of inactivated PRRSV entrapped PLGA nanoparticles. Scanning electronic photomicrograph of PLGA nanoparticles prepared by a standard multiple emulsion method. The size of the nanoparticles appears to be variable ranging 200-600 nm. (B) Mucosal vaccination of pigs with inactivated PRRSV entrapped in nanoparticles (Nano-KAg) cleared the viremia by PC 15. Pigs were unvaccinated (n=3) or vaccinated with either killed PRRSV (K-Ag) (n=3) or Nano-KAg (n=3) once intranasally, and on DPI 21 challenged with PRRSV VR2332 strain. Serum samples collected on indicated post-challenge day (PC) were analyzed to measure PRRSV titers. Each bar represents the average of three pigs±SEM.

Figure 17:
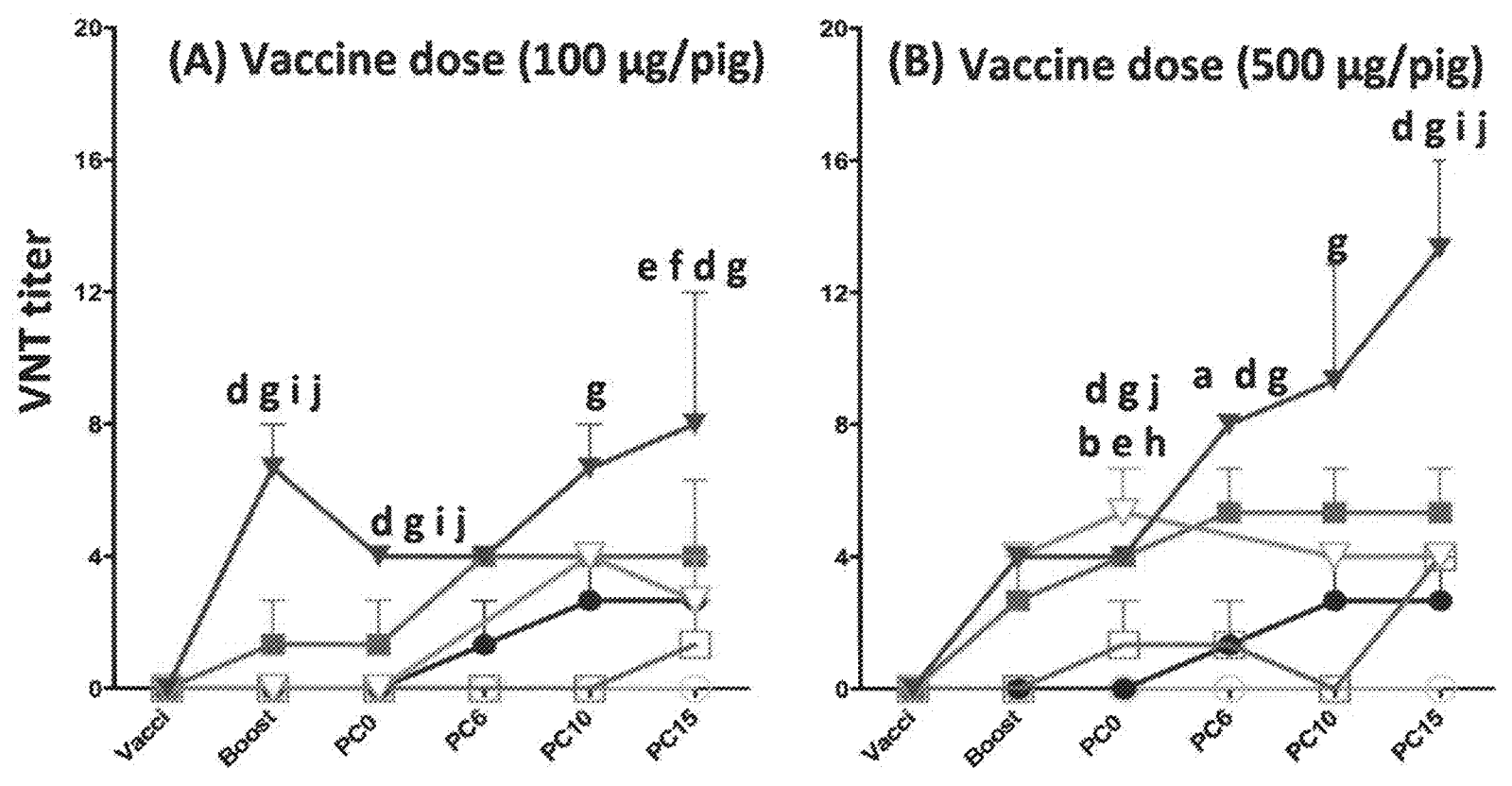

FIG. 17 shows an estimation of PRRSV specific neutralization titers (VNT) in the blood samples of pigs by immunofluorescence assay. PC—post-challenge day; Vacci.—1st vaccination; Boost—Booster dose.

Figure 19:
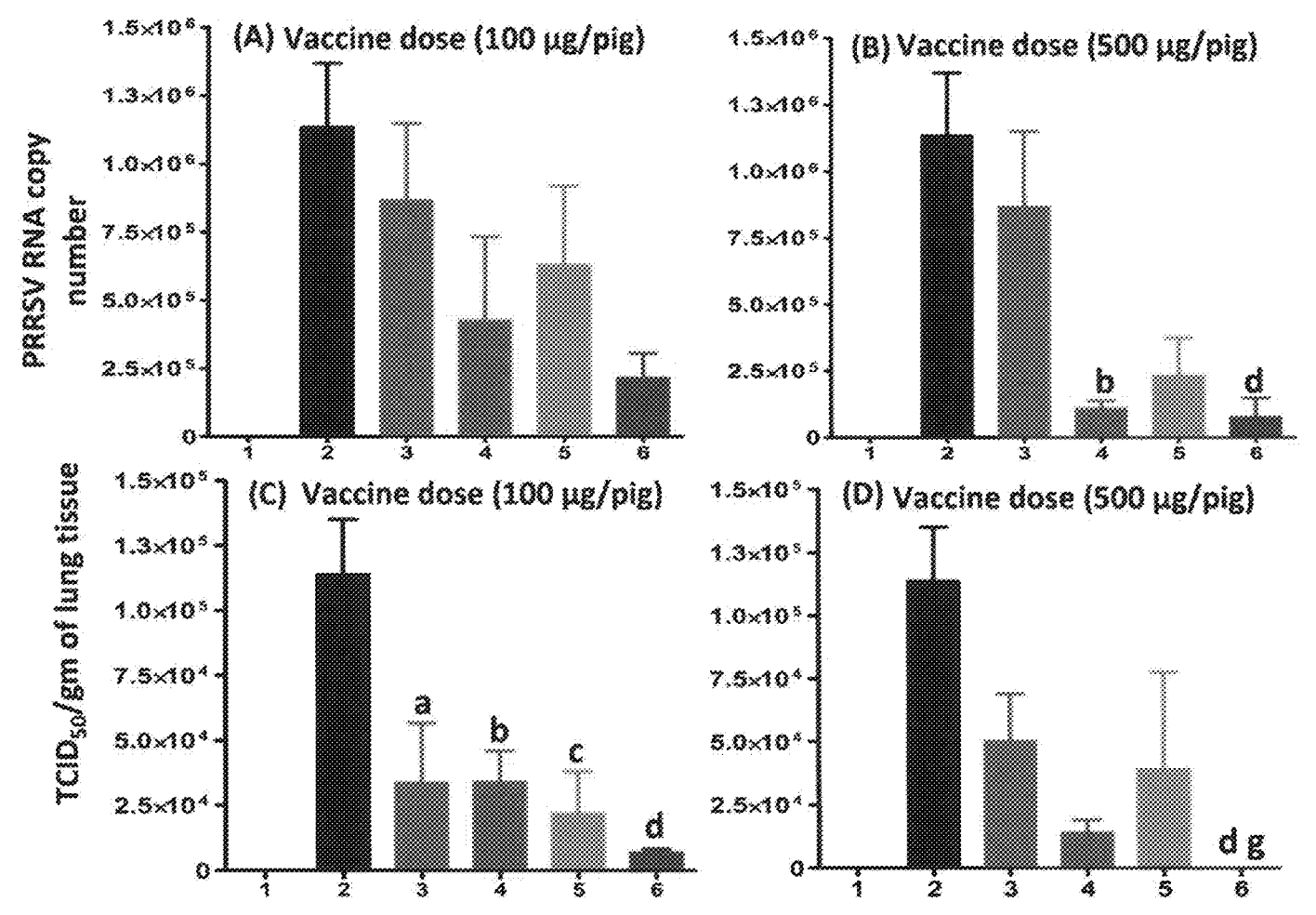

FIGS. 19 (A and B) shows the determination of PRRSV RNA copy number in the lungs by quantitative real time-PCR (qRT-PCR) and (C & D) determination of infective PRRSV titer in the lungs of pigs determined by immunofluorescence assay.

FIG. 21 shows a determination of infective PRRSV titer in the lungs of pigs by immuno-fluorescence assay. A & B are the negative and positive control, and C to H are representative pictures of viral load in lung homogenate of indicated pigs group (n=3) of 500 μg/pig vaccine dose category.

FIG. 23 shows a schematic of anti-PRRSV immunity in pigs vaccinated intranasally with PLGA nanoparticle-entrapped PRRSV vaccine and challenged with a heterologous virus.

FIGS. 28A-28R shows the significantly increased IFN-γ secreting lymphocyte subsets and APCs in pigs vaccinated with adjuvanted NP-KAg vaccine (500 µg/pig dose). Pigs were vaccinated and challenged as described in figure legend 25. LMNC (A-I) and PBMC (J-R) were restimulated with MN184 Ags and immunostained using indicated cell surface markers and intracellular IFN-γ and analyzed by Flow cytometry. Frequency of total IFN-γ+ cells (Ai, Ji) and a representative histogram of IFN-γ+ cells (Aii and Jii) present in the LMNC and PBMC, respectively. The dotted line: isotype control and solid line: IFN-γ+ specific staining IFN-γ+ lymphocyte subsets:CD4+IFN-γ+ (B, K); CD8+IFN-γ+ (C, L); CD4+CD8+IFN-γ+ (D, M); γδ+IFN-γ+ (E, N); NK (CD56+) (F, O); and CD56+IFN-γ+ cells (G, P) present in LMNC and PBMC were analyzed at PC 15. Also APCs population: MΦs rich population (CD172+CD163+SLA-II+) (H, G); and DCs rich population (CD172+CD11c+SLA-II+) (I, R) were analyzed. Each bar indicates the average frequency of indicated cells from three pigs±SEM. Asterisk indicates statistically significant difference between indicated pig groups.

FIGS. 30A-30F show the significantly increased PRRSV structural (GP5, M, and N) proteins specific IgG in the blood of pigs vaccinated with adjuvanted NP-KAg. Pigs were vaccinated or unvaccinated with indicated vaccine and adjuvant combination and challenged with PRRSV MN184. Blood samples collected at indicated days were analyzed for IgG titers against GP5 (A, B), M (C, D) and N (E, F) proteins by ELISA. Each symbol indicates the mean IgG titer±SEM of three pigs of the indicated group. Lowercase alphabet indicate statistically significant ($p<0.05$) difference between two indicated pig groups as described in materials and methods. A similar trend in result was obtained in an independent second experiment.

Figure 2:
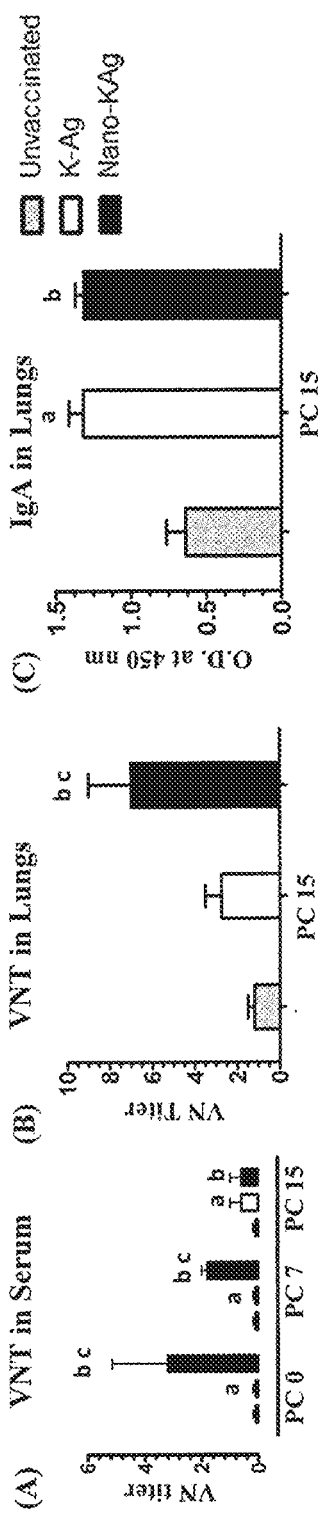
FIG. 2 shows enhanced IgA and neutralizing antibody titers in serum and lungs of Nano-KAg vaccinated virus challenged pigs. Analysis was performed to determine PRRSV neutralizing antibody response in: (A) serum; (B) lungs by immunofluorescence assay; and (C) anti-PRRSV IgA antibody response in the lung lysate by ELISA. Each bar in the graph represents average VN titer or optical density value from three pigs±SEM. Alphabet 'a', 'b' and 'c' represents the statistical significant difference (p<0.05) between unvaccinated vs K-Ag, unvaccinated vs Nano-KAg, and K-Ag vs Nano-KAg pigs, respectively.

FIGS. 33A-33I show the enhanced production of Th1-Th2 and suppressed immunosuppressive cytokines in pigs vaccinated with adjuvanted NP-KAg vaccine (100 µg/pig category). Pigs were vaccinated and challenged as described in figure legend 24. (A) Lung MNCs were restimulated with killed MN184 Ags and the frequency of IFN-γ secreting cells (ISCs) was measured by ELISPOT. Lung homogenates were analyzed for: (B) IFN-γ; (D) IL-12; (C) IL-6; (E) TGF-β; (F) IL-10 by ELISA. PBMC were restimulated with killed MN184 Ags and the supernatant was analyzed for: (G) IL-4; (H) IL-6; (I) IL-10 by ELISA. Each bar indicates the average number of ISCs per million LMNC or average of cytokines from three pigs±SEM. Asterisk indicates statistically significant difference between the indicated pig groups. A similar trend in result was obtained in an independent second experiment.

FIGS. 34A-34R shows the significantly increased IFN-γ secreting lymphocyte subsets and APCs in pigs vaccinated with adjuvanted NP-KAg vaccine (100 µg/pig dose). Pigs were vaccinated and challenged as described in figure legend 25. LMNC (A-I) and PBMC (J-R) were restimulated with MN184 Ags and immunostained using indicated cell surface markers and intracellular IFN-γ and analyzed by Flow cytometry. Frequency of total IFN-γ$^+$ cells (Ai, Ji) and a representative histogram of IFN-γ+ cells (Aii and Jii) present in the LMNC and PBMC, respectively. The dotted line: isotype control and solid line: IFN-γ$^+$ specific staining. IFN-γ+ lymphocyte subsets:CD4+IFN-γ$^+$ (B, K); CD8+IFN-γ$^+$ (C, L); CD4$^+$CD8$^+$IFN-γ$^+$ (D, M); γδ$^+$IFN-γ$^+$ (E, N); NK (CD56$^+$) (F, O); and CD56$^+$IFN-γ$^+$ cells (G, P) present in LMNC and PBMC were analyzed at PC 15. Also APCs population: MΦs rich population (CD172$^+$CD163$^+$SLA-II$^+$) (H, G); and DCs rich population (CD172$^+$CD11c$^+$SLA-II$^+$) (I, R) were analyzed. Each bar indicates the average frequency of indicated cells from three pigs±SEM. Asterisk indicates statistically significant difference between indicated pig groups.

FIGS. 35A and 35B show that NP-KAg (or PLGA-NanoPRRS) significantly reduced the viral load in the lungs and blood. Pigs were vaccinated as indicated (100 or 500 µg/pig dose) and challenged with a virulent hetrologus PRRSV MN184. PRRSV titers were determined by the indirect immunofluorescence assay: (A) lung lysate samples (titer in each gram of lung tissue); (B) blood samples (in each mL of plasma). Each bar or symbol indicates the average titer of three pigs±SEM. Asterisks/alphabets indicate statistically significant (p<0.5) difference in results between group 6 pigs with other tested groups.

Figures 36A, 36B:
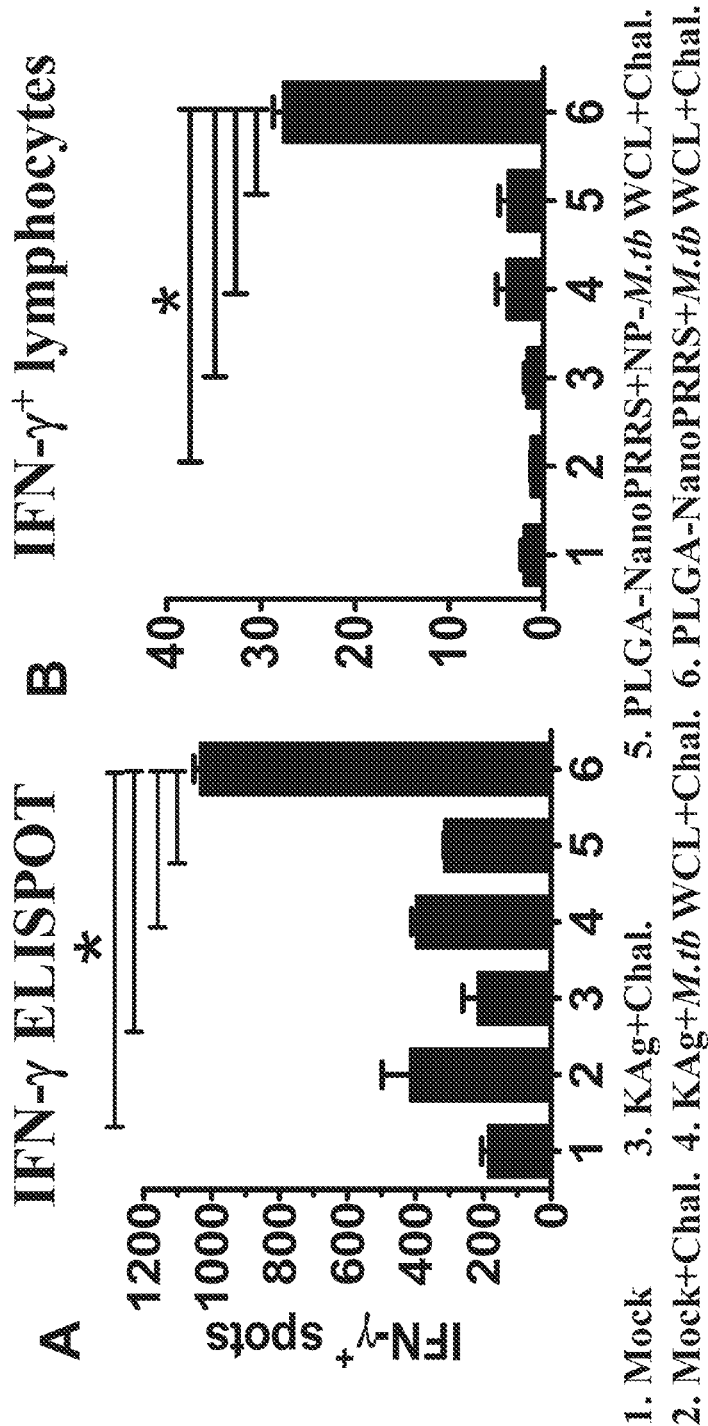

FIGS. 36A and 36B show that NP-KAg (or PLGA-NanoPRRS) significantly increased the IFN-γ response it he pig lungs. Pigs were vaccinated as indicated and challenged with a virulent heterologous PRRSV MN184. Lung MNCs collected at PC 15 were restimulated with killed PRRS Ags to analyze: (A) IFN-γ$^+$ spots by ELISPOT assay; (B) IFN-γ$^+$ lymphocytes by flow cytometry. Each bar indicates the average percent value of three pigs±SEM. Asterisks indicate statistically significant (p<0.05) different in results between group 6 pigs with other tested groups.

Figures 37A, 37B:
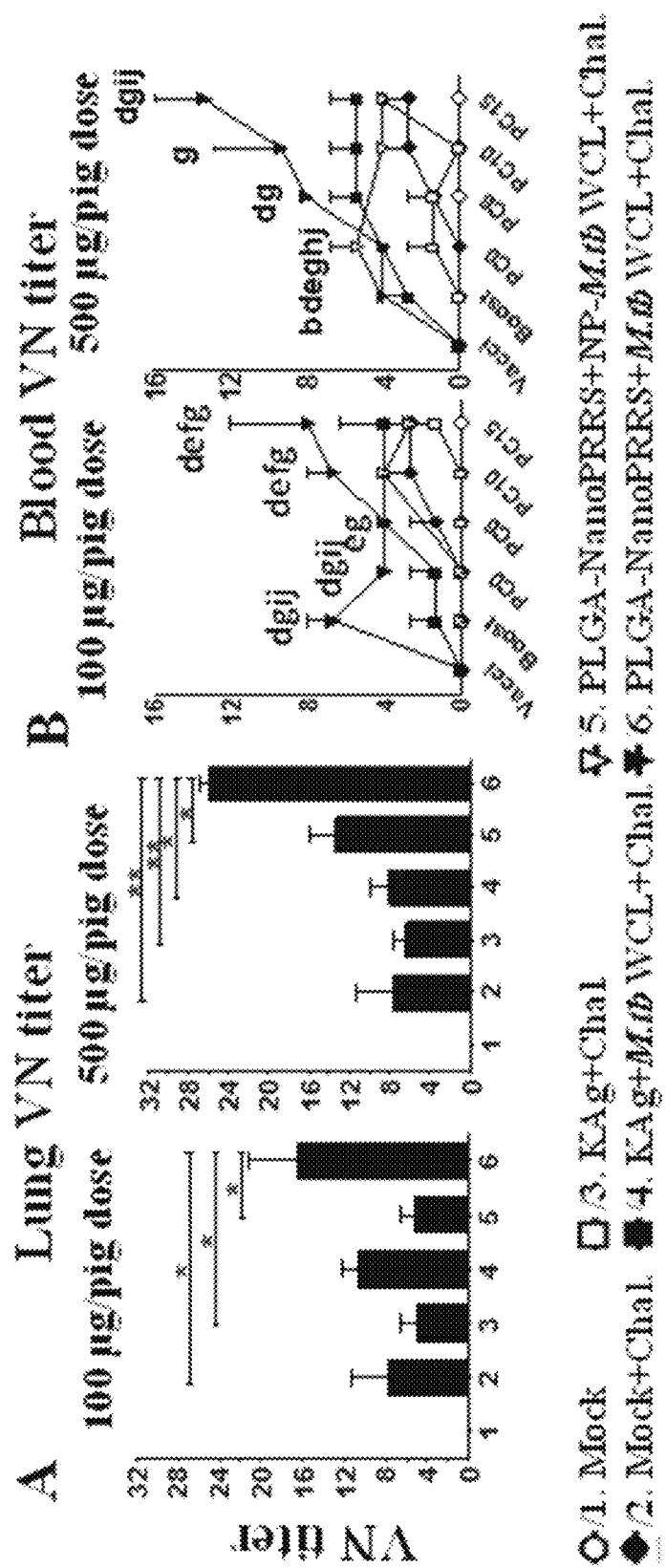

FIGS. 37A and 37B show that NP-KAg (or PLGA-NanoPRRS) significantly increased the PRRSV neutralization (VN) titers. Pigs were vaccinated as indicated (100 or 500 µg/pig dose) and challenged with a virulent hetrologus PRRSV MN184. Lung lysates prepared at PC 15 and plasma samples collected at indicated days were analyzed for VN titers against PRRSV MN184 in: (A) lung lysate and (B) plasma samples. Each bar or symbol indicates statistically significant (p<0.05) difference in results between group 6 pigs and other tested groups.

Figures 38A, 38B:
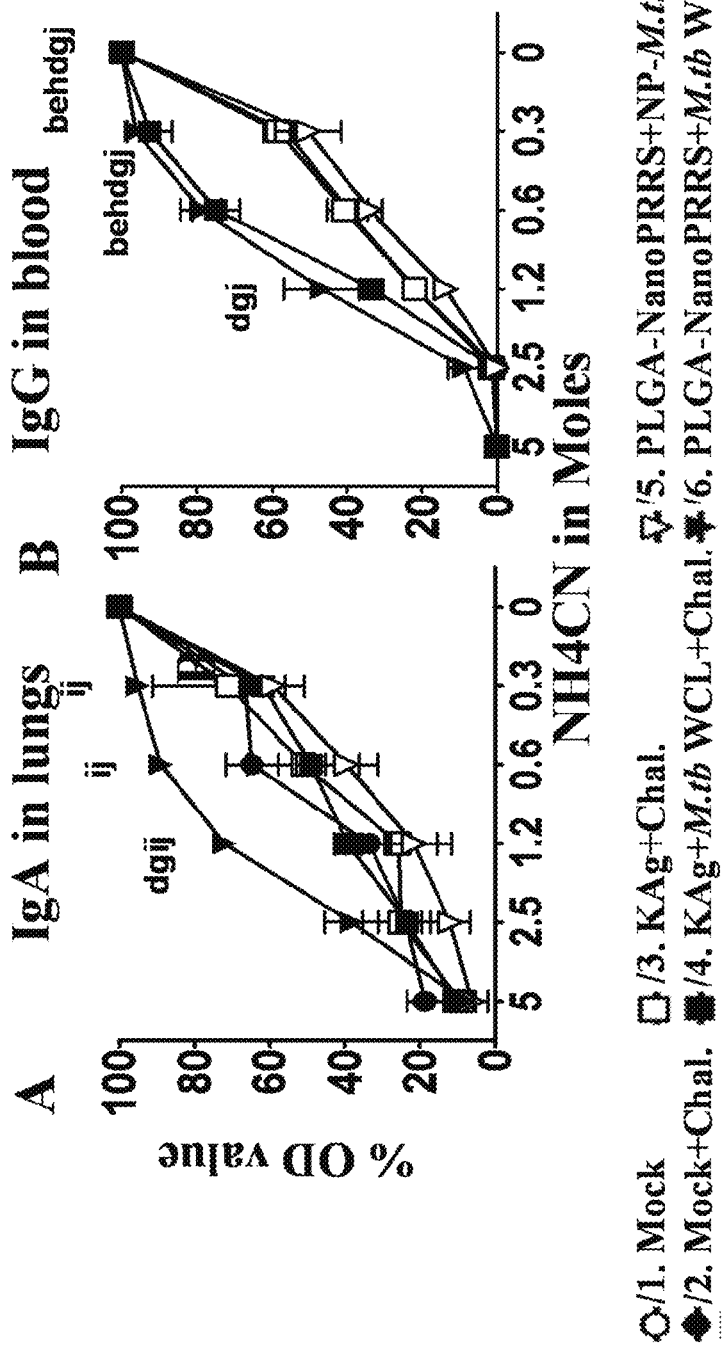

FIGS. 38A and 38B show that NP-KAg (or PLGA-NanoPRRS) significantly increased the avidity of PRRSV specific antibodies. Pigs were vaccinated (500 µg dose) as indicated and challenged with a virulent heterologous PRRSV MN184. Plasma and lung lysate samples collected at PC 15 were analyzed for virus specific: (A) IgA and (B) IgG avidity by ELISA. Each symbol indicates eh mean percent retained Ag-Ab complex compared to control [Ammonium thiocyanate (NH4CN) at 0 M conc.=100%] from three pigs±SEM. Alphabets indicate statistically significant (p<0.05) difference in results between group 6 pigs and other tested groups.

DETAILED DESCRIPTION

The present invention can be understood more readily by reference to the following detailed description of the invention and the Examples included therein.

All patents, patent applications, and publications cited herein, whether supra or infra, are hereby incorporated by reference in their entireties into this application in order to more fully describe the state of the art as known to those skilled therein as of the date of the invention described and claimed herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Definitions

Unless otherwise defined, all technical and scientific terms used herein have the same meaning as commonly understood by one of ordinary skill in the art to which this disclosure belongs. The terminology used in the description of the embodiments herein is for describing particular embodiments only and is not intended to be limiting of the embodiments disclosed. As used in the description, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in this disclosure are to be understood as being modified in all instances by the term "about." Accordingly, unless indicated to the contrary, the numerical parameters set forth in this disclosure are approximations that may vary depending upon the desired properties sought to be obtained by the present disclosure. At the very least, and not as an attempt to limit the application of the doctrine of equivalents to the scope of any claims, each numerical parameter should be construed in light of the number of significant digits and ordinary rounding approaches.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values described herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data are provided in a number of different formats, and that these data, represent endpoints, starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

The term "subject" means an individual. In one aspect, a subject is a mammal such as a primate, and, more preferably, a human. Non-human primates include marmosets, monkeys, chimpanzees, gorillas, orangutans, and gibbons, to name a few. The term "subject" also includes domesticated animals, such as cats, dogs, etc., livestock (for example, cattle (cows), horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). Subjects can also include, but are not limited to fish (for example, zebrafish, goldfish, tilapia, salmon, and trout), amphibians and reptiles. As used herein, a "subject" is the same as a "patient," and the terms can be used interchangeably.

The word "or" as used herein means any one member of a particular list and also includes any combination of members of that list.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. The terms "polypeptide," "peptide," and "protein" can be used interchangeably.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample can also be any body fluid or excretion (for example, but not limited to, blood, urine, stool, saliva, tears, bile) that contains cells or cell components.

As used herein, "prevent" is meant to mean minimize the chance that a subject who has an increased susceptibility for developing PRRS infection will develop PRRS infection.

The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "about") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof.

An "immunogenic composition" is a composition of matter suitable for administration to a human or animal subject (e.g., in an experimental setting) that is capable of eliciting a specific immune response, e.g., against a pathogen, such as PRRSV. As such, an immunogenic composition includes one or more antigens (for example, whole purified virus or antigenic subunits, e.g., polypeptides, thereof) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or treated, e.g., reduced or ameliorated) by inhibiting replication of the pathogen following exposure of the subject to the pathogen. In the context of this disclosure, the term immunogenic composition will be understood to encompass compositions that are intended for administration to a subject or population of subjects for the purpose of eliciting a protective or palliative immune response against the virus (that is, vaccine compositions or vaccines).

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification or precipitation. Thus, the term "purified" does not require absolute purity; rather, it is intended as a relative term. Thus, for example, a purified virus preparation is one in which the virus is more enriched than it is in its generative environment, for instance within a cell or population of cells in which it is replicated naturally or in an artificial environment. A preparation of substantially pure viruses can be purified such that the desired virus or viral component represents at least 50% of the total protein content of the preparation. In certain embodiments, a substantially pure virus will represent at least 60%, at least 70%, at least 80%, at least 85%, at least 90%, or at least 95% or more of the total protein content of the preparation.

An "isolated" biological component (such as a virus, nucleic acid molecule, protein or organelle) has been substantially separated or purified away from other biological components in the cell and/or organism in which the component occurs or is produced. Viruses and viral components, e.g., proteins, which have been "isolated" include viruses, and proteins, purified by standard purification methods. The term also embraces viruses and viral components (such as viral proteins) prepared by recombinant expression in a host cell.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule). An antigen can also affect the innate immune response.

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). An immune response can also include the innate response. If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

The immunogenic compositions disclosed herein are suitable for preventing, ameliorating and/or treating disease caused by infection of the virus.

The abbreviation "KAg" stands for killed antigen and represents the killed or inactivated PRRSV. The inactivated PRRSV comprises one or more immunogenic PRRS viral proteins and therefore the inactivated PRRSV can be considered a killed antigen.

The abbreviation "NP-KAg" stands for nanoparticle-killed antigen. This represents the nanoparticle encapsulated inactivated PRRSV.

As used herein, the terms "virus-like particle" or "VLP" refer to a nonreplicating, viral shell. VLPs are generally composed of one or more viral proteins associated with viral surface capsid structure, such as, but in case of PRRSV they are not limited to structural proteins GP3, GP4, GP5, and matrix proteins of PRRSV or combinations thereof. VLPs can form spontaneously upon recombinant expression of the protein in an appropriate expression system. VLPs, when administered to an animal, can be immunogenic and thus can cause a protective or therapeutic immune response in the animal. Methods for producing VLPs are generally known in the art and discussed more fully below. The presence of VLPs following recombinant expression of viral proteins can be detected using conventional techniques known in the art, such as by electron microscopy, biophysical characterization, and the like. See, e.g., Baker et al., Biophys. J. (1991) 60:1445-1456; Hagensee et al., J. Virol. (1994) 68:4503-4505. For example, VLPs can be isolated by density gradient centrifugation and/or identified by characteristic density banding.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

In addition, where features or aspects of the inventions are described in terms of Markush groups or other grouping of alternatives, those skilled in the art will recognize that the invention is also thereby described in terms of any individual member or subgroup of members of the Markush group or other group.

COMPOSITIONS

When a human or non-human animal is challenged by a foreign organism/pathogen the challenged individual responds by launching an immune response which may be protective. This immune response is characterized by the co-ordinated interaction of the innate and acquired immune response systems.

The innate immune response forms the first line of defense against a foreign organism/pathogen. An innate immune response can be triggered within minutes of infection in an antigen-independent, but pathogen-dependent, manner. The innate, and indeed the adaptive, immune system can be triggered by the recognition of pathogen associated molecular patterns unique to microorganisms by pattern recognition receptors present on most host cells. Once triggered the innate system generates an inflammatory response that activates the cellular and humoral adaptive immune response systems.

The adaptive immune response becomes effective over days or weeks and provides the antigen specific responses needed to control and usually eliminate the foreign organism/pathogen. The adaptive response is mediated by T cells (cell mediated immunity) and B cells (antibody mediated or humoral immunity) that have developed specificity for the pathogen. Once activated these cells have a long lasting memory for the same pathogen.

The ability of an individual to generate immunity to foreign organisms/pathogens, thereby preventing or at least reducing the chance of infection by the foreign organism/pathogen, is a powerful tool in disease control and is the principle behind vaccination.

Vaccines function by preparing the immune system to mount a response to a pathogen. Typically, a vaccine comprises an antigen, which is a foreign organism/pathogen or a toxin produced by an organism/pathogen, or a portion thereof, that is introduced into the body of a subject to be vaccinated in a non-toxic, non-infectious and/or non-pathogenic form. The antigen in the vaccine causes the subject's immune system to be "primed" or "sensitised" to the organism/pathogen from which the antigen is derived. Subsequent exposure of the immune system of the subject to the organism/pathogen or toxin results in a rapid and robust specific immune response, that controls or destroys the organism/pathogen or toxin before it can multiply and infect or damage enough cells in the host organism to cause disease symptoms.

In many cases it is necessary to enhance the immune response to the antigens present in a vaccine in order to stimulate the immune system to a sufficient extent to make a vaccine effective, that is, to confer immunity. To this end, additives known as adjuvants (or immune potentiators) have been devised which enhance the in vivo immune response to an antigen in a vaccine composition.

An adjuvant component can increase the strength and/or duration of an immune response to an antigen relative to that elicited by the antigen alone. A desired functional characteristic of an adjuvant component is its ability to enhance an appropriate immune response to a target antigen.

Described herein are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Described herein are compositions comprising an immunogenic porcine reproductive and respiratory syndrome virus (PRRSV) antigen and a nanoparticle.

The compositions, immunogenic compositions and vaccines described herein can further comprise one or more adjuvants. The adjuvant can be any composition, pharmacological or immunological agent that modifies the effect of other agents, such as the antigens described herein. Examples of adjuvants include, but are not limited to *Mycobacterium* lysate (including a *Mycobacterium tuberculosis* whole cell lysate), a *Mycobacterium smegmatis* (including *Mycobacterium smegmatis* whole cell lysate), choleratoxin B subunit, and *E. coli* heat labile mutant toxin. Other examples of adjuvants include evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Additional examples of adjuvants, include, but are not limited to are aluminum containing adjuvants that include a suspensions of minerals (or mineral salts, such as aluminum hydroxide, aluminum phosphate, aluminum hydroxyphosphate) onto which antigen is adsorbed. Adjuvants Additional examples of adjuvants, include, but are not limited to aluminum-(alum-)free adjuvants, which are formulated in the absence of any such aluminum salts. Alum-free adjuvants include oil and water emulsions, such as water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

In some embodiments, the compositions, immunogenic compositions and vaccines described herein can further comprise both *Mycobacterium tuberculosis* whole cell lysate, *Mycobacterium smegmatis* whole cell lysate, and *Mycobacterium vaccae* whole cell lysate.

The compositions, immunogenic compositions and vaccines described herein can comprise one or more nanoparticles. Examples of nanoparticles (used interchangably with the term "nanocarrier") can be found, for example, in U.S. patent application 20100233251. Examples of nanocarriers include, but are not limited to nanocarriers composed of one or more polymers. In some embodiments, the one or more polymers is a water soluble, non-adhesive polymer. In some embodiments, polymer is polyethylene glycol (PEG) or polyethylene oxide (PEO). In some embodiments, the polymer is polyalkylene glycol or polyalkylene oxide. In some embodiments, the one or more polymers is a biodegradable polymer. In some embodiments, the one or more polymers is a biocompatible polymer that is a conjugate of a water soluble, non-adhesive polymer and a biodegradable polymer. In some embodiments, the biodegradable polymer is polylactic acid (PLA), poly(glycolic acid) (PGA), or poly (lactic acid/glycolic acid) (PLGA). In some embodiments, the nanocarrier is composed of PEG-PLGA polymers.

In some embodiments, the nanocarrier is formed by self-assembly. Self-assembly refers to the process of the formation of a nanocarrier using components that will orient themselves in a predictable manner forming nanocarriers predictably and reproducably. In some embodiments, the nanocarriers are formed using amphiphillic biomaterials which orient themselves with respect to one another to form nanocarriers of predictable dimension, constituents, and placement of constituents. In some embodiments, the nanocarrier is a microparticle, nanoparticle, or picoparticle. In some embodiments, the microparticle, nanoparticle, or picoparticle is self-assembled.

In some embodiments, the nanocarrier has a positive zeta potential. In some embodiments, the nanocarrier has a net positive charge at neutral pH. In some embodiments, the nanocarrier comprises one or more amine moieties at its surface. In some embodiments, the amine moiety is a primary, secondary, tertiary, or quaternary amine. In some embodiments, the amine moiety is an aliphatic amine. In some embodiments, the nanocarrier comprises an amine-containing polymer. In some embodiments, the nanocarrier comprises an amine-containing lipid. In some embodiments, the nanocarrier comprises a protein or a peptide that is positively charged at neutral pH. In some embodiments, the nanocarrier is a latex particle. In some embodiments, the nanocarrier with the one or more amine moieties on its surface has a net positive charge at neutral pH.

Nanoparticles can aid the delivery of the inactivated PRRSV and/or can also be immunogenic. Delivery can be to a particular site of interest, e.g. the mucosa. In some embodiments, the nanoparticle can create a timed release of the inactivated PRRSV to enhance and/or extend the immune response. In some embodiments, the nanoparticle is associated with the inactivated PRRSV such that the composition can elicit an immune response. The association can be, for example, wherein the nanoparticle is coupled or conjugated with the inactivated PRRSV. By coupled and conjugated is meant that there is a chemical linkage between the nanoparticle and the inactivated PRRSV. In some embodiments, the inactivated PRRSV is entrapped or encapsulated within the nanoparticle. In some embodiments, the inactivated PRRSV is entrapped within the nanoparticle by a water/oil/water emulsion method. In some embodiments, the nanoparticle is poly(lactide co-glycolide) (PLGA). Depending on the ratio of lactide to glycolide used for the polymerization, different forms of PLGA can be obtained and utilized. These forms are typically identified in regard to the monomers' ratio used (e.g. PLGA 75:25 identifies a copolymer whose composition is 75% lactic acid and 25% glycolic acid). Different ratios can be used in this invention, e.g. 90:10, 80:20, 70:30, 60:40, 50:50, 40:60, 30:70, 20:80, 10:90, and numbers above and in between these ratios. Additional examples of suitable nanoparticles include chitosin, calcium phosphate, lipids of various bacteria like *E. Coli*, mycobactera, leptospira and mixtures thereof. In one example, the composition can be derived mixing about 180 mg of PLGA to about 5 mg of inactivated PRRSV (or about 36 mg PLGA to 1 mg inactivated PRRSV). The entrapment (encapsulation) efficiency of inactivated PRRSV can vary. In one embodiment the nanoparticle were 50-55% entrapped/encapsulated, calculated based on amount of total PRRSV protein used in the entrapment. Entrapped inactivated PRRSV can be administered as mixtures of entrapped/encapsulated and unentrapped/unencapsulated antigens or the entrapped/encapsulated antigens can be further purified.

In some embodiments, the antigen is derived from inactivated or killed PRRSV. In one embodiment, the PRRSV is inactivated or killed by UV light. Other means of inactivation include chemical, heat, or radioactivity.

Any suitably immunogenic inactivated PRRSV or PRRSV antigen can be utilized in the composition. The complete genome sequence of the PRRS virus is about 15 kb in size and contains 7 Open Reading Frames (ORF). The six smaller ORF's, 2-7, encode structural proteins associated with the virion and are examples that can be used in the compositions of this invention. Examples of immunogenic antigens include GP2, 3, 4, 5, M 19, N15, mixtures thereof, and the like. The PRRSV antigen can be recombinantly derived.

The disclosed compositions can comprise an inactivated PRRSV that is immunogenic. The disclosed compositions can also comprise an inactivated PRRSV that comprises PRRSV antigens. For example, the PRRSV antigen can be a PRRSV surface glycoprotein.

Disclosed are compositions comprising virus-like particles (VLPs) and a nanoparticle. The disclosed compositions can comprise a VLP that is immunogenic. VLPs resemble viruses, but are non-infectious because they do not contain any viral genetic material. The expression of viral structural proteins, such as Capsid, can result in the self-assembly of VLPs. VLPs can be produced in a variety of cell culture systems including mammalian cell lines, insect cell lines, yeast, and plant cells. For example, the VLP can be produced by a baculovirus or a plant system. The VLP can be immunogenic. Any of the disclosed nanoparticles can be used to entrap the PRRSV VLP. For example, disclosed are PRRSV VLPs entrapped in PLGA nanoparticles.

In some embodiments, the disclosed compositions further contain the lectin *Ulex Europaeus* Agglutinin-I (UEA). The UEA can be entrapped in the nanoparticle with the inactivated PRRSV or VLPs and can also be surface-anchored to the nanoparticle. M cells are specialized endothelial cells overlaying the mucosal lymphoid follicles called the follicle-associated epithlium (FAE) and contain α-1-fucose receptors which bind to UEA. Thus, the presence of the UEA can help direct the composition or vaccine to mucosal specialized follicle or epithelial cells.

Described herein are vaccines comprising a composition of this invention in a carrier wherein the vaccine is protective against PRRSV infection. The term "immunogenic carrier" as used herein can refer to a first polypeptide or fragment, variant, or derivative thereof which enhances the immunogenicity of a second polypeptide or fragment, variant, or derivative thereof. An "immunogenic carrier" can be fused, to or conjugated/coupled to the desired polypeptide or fragment thereof. See, e.g., European Patent No. EP 0385610 B1, which is incorporated herein by reference in its entirety for its teaching of fusing, conjugating or coupling a polypeptide to a carrier. An example of an "immunogenic carrier" is PLGA. In some embodiments the vaccine can comprise whole virus inactivated PRRSV, encapsulated by PLGA, and a carrier. In some embodiments the vaccine can further comprise a *Mycobacterium tuberculosis* whole cell lysate.

Methods

Described herein are methods of eliciting an immune response against PRRSV in a pig comprising administering to the pig a composition of the invention. The immune response can be protective. The method can further comprise administering to the pig virulent PRRSV to monitor the vaccine efficacy. The virulent PRRSV can be the MN184 strain of PRRSV, a virulent and genetically variant strain of PRRSV.

Described herein are methods of reducing reproductive or respiratory failure in pigs comprising the steps of: providing a composition provided herein; and administering the composition to pigs. The method can further comprise administering to the pig virulent PRRSV to monitor the vaccine efficacy. The virulent PRRSV can for example be the MN184 strain of PRRSV. Also described are methods of stimulating an immune response in a pig comprising: administering to said pig a vaccine or composition provided herein.

Described herein are methods of administering the compositions and methods set forth herein for the complete clearance of PRRSV viremia. Also described are methods and compositions that can be used to increase (e.g. 0.5, 1, 2, 3, 4, 5, 6, 7, 8, 9, 10, 15, 20, 30 etc. fold increased) anti-PRRSV humoral and cell-mediated immune response compared to killed PRRSV vaccine antigens (K-Ag) in immunized homologous virus challenged pigs. The methods and compositions described herein can also be used to provide a significant increase (e.g. 0.5, 1, 2, 3, 4, 5, 6, 7, 8, 9, 10, 15, 20, 30 etc. fold increased) in virus neutralizing antibodies and IgA response in the lungs and blood when compared to killed PRRSV vaccine antigens (K-Ag) in immunized, homologous virus challenged pigs. The methods and compositions described herein can also be used to provide lung lysate and serum of Nano-KAg vaccinated pigs with higher levels (e.g. 0.5, 1, 2, 3, 4, 5, 6, 7, 8, 9, 10, 15, 20, 30 etc. fold increased) of IFN-γ and IL-12, and lower levels of immunosuppressive mediators (IL-10 and TGF-β) (e.g. 0.5, 1, 2, 3, 4, 5, 6, 7, 8, 9, 10, 15, 20, 30 etc. fold decreased) compared to control pig groups. The methods and compositions described herein can also be used to provide mononuclear cells from the lungs, blood, BAL, TBLN, and blood of Nano-KAg vaccinated pigs having increased frequencies (e.g. 0.5, 1, 2, 3, 4, 5, 6, 7, 8, 9, 10, 15, 20, 30 etc. fold increased) of $CD4^+$, $CD8^+$, $CD4^+CD8^+$ T cells, γδ T cells, myeloid cells, and dendritic cells rich fractions. The methods and compositions can also be used to provide a decrease (e.g. 0.5, 1, 2, 3, 4, 5, 6, 7, 8, 9, 10, 15, 20, 30 etc. fold decreased) in $Foxp3^+$ T-regulatory cells. The compositions and methods can also be used to provide intranasal delivery of PLGA nanoparticle-entrapped PRRSV killed vaccine that elicits an immune response at both mucosal and systemic sites sufficient to clear the viremia in pigs.

Also provided are the composition and methods than can be used to provide protective systemic and mucosal immune responses against PRRSV that can clear the viremia early post-infection, e.g. three, two, and one week post infection (including 1, 2, 3, 4, 5, 6, 7, 8, 9, 10, 15, 20, 25, 30 days).

The vaccine or composition can also be administered at a dose, for example, of between 100 ug/pig and 1 mg/pig. Other examples include doses comprising 50 ug/pig and 500 ug/pig. The composition or vaccine can be administered for example in a single dose, or in two or more doses. In one embodiment, the two doses are administered at a two week interval. The composition or vaccine can, for example, be administered intranasally. Additional examples of alternative routes of immunization include intramuscular, subcutaneous, intranasal drops, and intranasal aerosol delivery.

The compositions and methods can also be used at a dose of vaccine or immunogen having less than $1 \times 10^8$ $TCID_{50}$ of PRRSV. Also provided is a dose less than $1 \times 10^7$, $1 \times 10^6$, and $1 \times 10^5$ $TCID_{50}$ of PRRSV. Further disclosed herein, each dose can be approximately $5 \times 10^6 TCID_{50}$ of PRRSV. Also provided are examples of doses between $1 \times 10^8$ $TCID_{50}$ of PRRSV and $1 \times 10^5$ $TCID_{50}$ of PRRSV, between $1 \times 10^7$ and $1 \times 10^5 TCID_{50}$ of PRRSV, between $1 \times 10^6$ and $5 \times 10^6 TCID_{50}$ of PRRSV. The doses can be derived from UV treated PRRSV. The doses can be administered as a single reduced viral dose to elicit a protective immune response.

EXAMPLES

Example 1

Nanoparticle Encapsulated Killed Porcine Reproductive and Respiratory Syndrome Virus Vaccine Elicits Adequate Immune Response in Pigs In this Example, a PLGA [poly(D,L-lactide-co-glycolide)] nanoparticle entrapped candidate killed PRRSV vaccine (Nano-KAg) was developed and administered intranasally and evaluated immune correlates in homologous virus challenged pigs. The results in Nano-KAg vaccinated pigs identified complete clearance of viremia associated with increased anti-PRRSV humoral and cell-mediated immune response compared to unvaccinated and killed PRRSV vaccine antigens (K-Ag) immunized, homologous virus challenged pigs. Immunologically, Nano-KAg immunized pigs had a significant increase in virus neutralizing antibodies and IgA response in the lungs and blood. Lung lysate and serum of Nano-KAg vaccinated pigs had higher levels of IFN-γ and IL-12, and lower levels of immunosuppressive mediators (IL-10 and TGF-β) compared to control pig groups. Mononuclear cells from the lungs, blood, BAL, TBLN, and blood of Nano-KAg vaccinated pigs had increased frequencies of CD4+, CD8+, CD4+CD8+ T cells, γδ T cells, myeloid cells, and dendritic cells rich fraction; and conversely a decrease in Foxp3+T-regulatory cells. Overall, the results show that intranasal delivery of PLGA nanoparticle-entrapped PRRSV killed vaccine was safe, and it elicits adequate immune response at both mucosal and systemic sites sufficient to clear the viremia in pigs.

Material and Methods
Cells, PRRSV and Polymer

Stable *Mycoplasma*-free MARC-145 cells (37) were used for preparation of the vaccine and in vitro assays. Cells were maintained in DMEM (Lonza) with 10% fetal bovine serum (Atlanta Biologicals). The virus infection medium was DMEM supplemented with 2% horse serum. For preparation of nanoparticles, PLGA 50:50 (mol. wt 40-75 kDa), polyvinyl alcohol (mol. wt. 30-70 kDa) (Sigma-Aldrich), Dichloro methane (Acros Organics), and BCA (bicinchoninic acid) protein assay kit (Pierce) were used.

Animals

Conventional Large White-Duroc crossbred weaned specific-pathogen-free pigs at 3-4 wks of age were housed in a BSL-2 facility at FAHRP, OARDC. The swine herd was confirmed seronegative for PRRSV, porcine respiratory corona virus, transmissible gastroenteritis virus, and porcine circo virus 2. Piglets blood samples collected on arrival were confirmed negative for PRRSV antibodies. All the animals received food and water ad libitum.

Preparation of Inactivated PRRSV

MARC-145 cell-monolayer was infected with the North American prototype PRRSV strain VR2332 strain (38) at 0.01 MOI (multiplicity of infection), and freeze-thawed thrice when >80% cytopathic effect was seen. Harvested infected cell culture fluid was clarified at 2000×g and then subjected to ultracentrifugation with a 20% sucrose overlay at 100,000×g for 2 hr. Pooled crude viral pellet was suspended in sterile PBS and titrated. The pellet was UV irradiated (254 nm for 1 hr), confirmed the inactivation, sonicated, protein content was estimated using BCA kit (Pierce), and stored at −70° C. Control antigen was prepared in the same manner using uninfected MARC-145 cells.

Preparation of PLGA Nanoparticles

Nanoparticles were prepared by a standard double emulsion solvent evaporation method (40). Briefly, 15% of PLGA 50/50 (750 mg) was dissolved in 5 ml of dichloromethane and 100 µl of killed VR2332 proteins (5 mg) was added. The mixture was homogenized for 90 seconds using a Brinkman Polytron homogenizer at 6000 rpm. The homogenized mixture was added to 60 ml of aqueous solution of polyvinyl alcohol (10% PVA), and homogenized for 5 min. Finally, the preparation was stirred overnight at room temperature (RT) to allow solvent evaporation. The nanoparticles were washed in distilled water three times and the wet nanoparticles were freeze-dried and stored at 4° C.

Determination of Size, Morphology, and Protein Entrapment Efficiency of Nanoparticles The size and morphology of nanoparticle was detected using scanning electron microscopy (Hitachi S-3500N). Briefly, freeze-dried nanoparticles were mounted on an adhesive stub coated with gold platinum under vacuum using an ion coater. The coated specimen was examined under the microscope at 10 KV. The amount of entrapped inactivated PRRSV in the nanoparticles was determined as described previously (41).

Pigs and Inoculations

Pigs (n=12) were divided into four groups (n=3 pigs per group). Group I—mock pigs; Group II—inoculated with normal saline; Group III—inoculated with killed VR2332 antigens (K-Ag); Group IV—inoculated with nanoparticle-entrapped killed VR2332 antigens (Nano-KAg). Each vaccine (Nano-KAg and K-Ag) dose was 1 mg of crude viral preparation containing equivalent ~5×10$^6$ TCID50 of inactivated virus. Groups II, III, and IV were challenged with PRRSV VR2332 (1×106 TCID50/ml, 2 ml per pig) on day post-immunization (DPI) 21 and euthanized on day post-challenge (DPC or PC) 15. All the inoculations in this study were performed once by intranasal route. Mock-inoculated pigs were euthanized separately before virus challenged animals.

Collection of Blood and Lung Samples for Analysis

For evaluation of viremia and for titration of PRRSV specific VN antibodies, 3 to 5 ml of blood samples were collected on DPI 0 and 21, and DPC 7 and 15, and serum samples were aliquoted and kept at −20° C. Lung homogenates were prepared for cytokine and virus evaluation (46, 12).

Isolation of PBMC, Lung MNC, BAL, TBLN Cells

Isolation of PBMC, lung-mononuclear cells (lung MNC/LMNC), and tracheobronchial lymph nodes (TBLN) MNC was performed as per the described procedure (20, 21). The airways were lavaged to collect BAL cells using sterile ice cold PBS containing EDTA (0.03%) (49).

Virus Titration, Virus-Neutralizing Test (VNT), and Isotype Specific Antibody Analysis PRRSV titer and VN antibody titer in serum and in lung lysate were analyzed by indirect immunofluorescence assay (IFA) (37, 48). PRRSV specific IgA antibodies in serum and lung lysate were analyzed by ELISA (95). To eliminate the background activity, non-PRRSV specific antigen coated control plates were also used, blocked and treated with test samples side-by-side. The OD values obtained from experimental plates were subtracted from the control plate.

PRRSV Specific Recall/Memory Immune Response

Five million pig PBMC, TBLN MNC, and lung MNC were subjected to ex vivo restimulation in the absence or presence of killed crude PRRSV VR2332 antigens (Ags) (50 µg/ml) as described (48), and the harvested supernatant was analyzed to measure cytokines.

Analysis of Cytokine Response and Flow Cytometric Analyses of Immune Cells

Serum samples, harvested culture supernatants, and lung lysates were analyzed for Th1 (IFN-γ and IL-12), Th2 (IL-4), pro-inflammatory (IL-6), and immunosuppressive (IL-10 and TGF-β) cytokines by ELISA (48). Amount of cytokines present in the lung lysate was converted to picogram per gram of lung tissue. Flow cytometry analysis was performed to determine the phenotype and the frequency of different immune cells by a multicolor immunoassay as described (48).

Statistical Analysis

All data were expressed as the mean+/−SEM of three pigs. Statistical analyses were performed using one way analysis of variance (ANOVA) followed by post-hoc Tukey's test using GraphPad InStat (software version 5.0 for windows) to establish differences between experimental groups. Statistical significance was assessed as $P<0.05$.

Results

Characterization of Inactivated PRRSV Entrapped Nanoparticles

Figure 1:
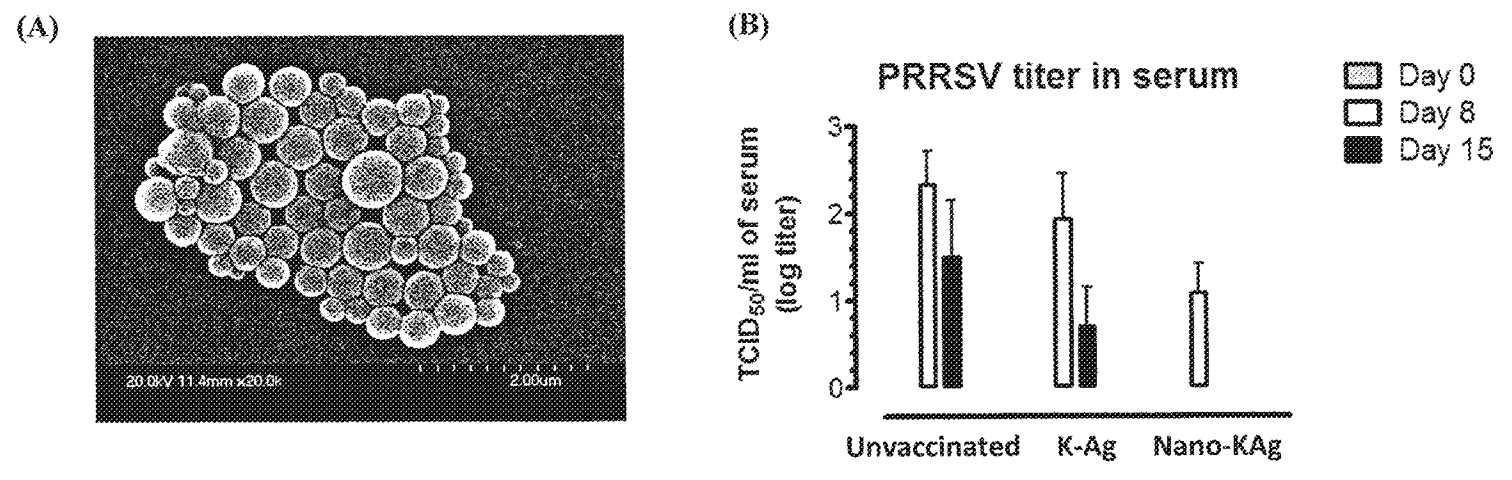

The size of both sham as well as inactivated PRRSV loaded nanoparticles was in the range of 200-600 nm (FIG. 1A). The yield of prepared nanoparticles was 82.32±3.3% calculated based on amount of PLGA polymer used. The morphology of the nanoparticles containing inactivated PRRSV was spherical with no surface discontinuity (FIG. 1A). The entrapment efficiency of inactivated PRRSV in nanoparticles was 50-55%, calculated based on amount of total PRRSV protein used in the entrapment.

Viral Load and Humoral Immune Response in Pigs

Nano-KAg vaccinated pigs had reduction in viremia by greater than 1 log at PC 8 and the viremia was completely cleared by DPC 15 compared to both the control pig groups (FIG. 1B).

Nano-KAg vaccinated pigs had consistently increased levels of VN antibodies in serum with significantly higher levels at PC 0 and 7 compared to both the control pig groups (FIG. 2A). Similarly, significantly increased VN antibody titer in the lung lysate of Nano-KAg received pigs at PC 15 compared to both the control pig groups was detected (FIG. 2B). However, lungs of both K-Ag and Nano-KAg vaccinated pigs had significantly increased PRRSV specific IgA titer compared to unvaccinated virus challenged animals (FIG. 2C).

Secretion of Increased Th1, Reduced Th2 and Immunosuppressive Cytokines in Nano-KAg Vaccinated Pigs The Th1 cytokine, IFN-γ, in serum of unvaccinated pigs was undetectable, and it was at lower levels in serum of K-Ag immunized, virus challenged pigs. However, in Nano-KAg vaccinated pigs, a significantly increased level of IFN-γ at PC 7 and 15 compared to both control groups was detected (FIG. 3A). Similarly, Nano-KAg immunized pig lungs had significantly higher levels of IFN-γ secretion than both the control pig groups at PC 15 (FIG. 3C).

Figure 3:
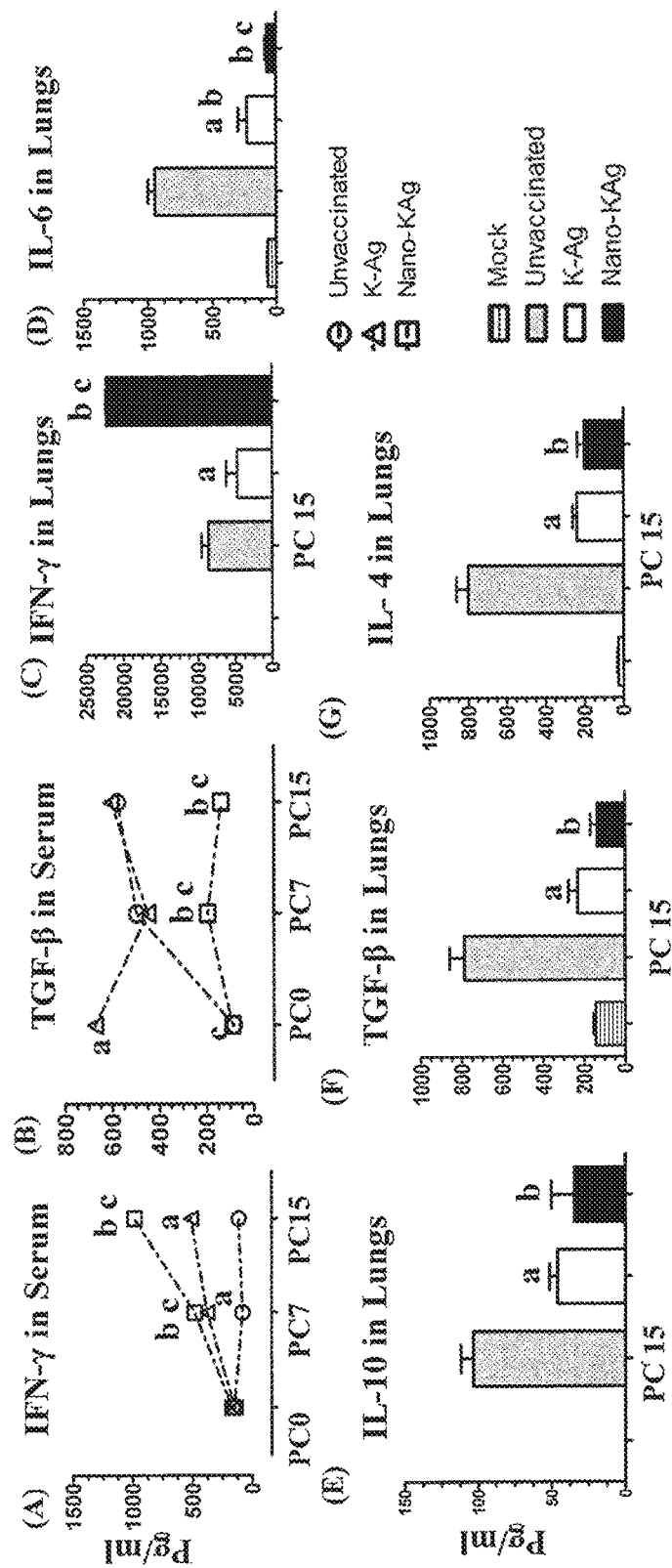
FIG. 3 shows cytokine response in serum and lungs of pigs intranasally vaccinated with Nano-KAg vaccine. Serum samples collected at indicated PCs were analyzed for cytokines, (A) IFN-γ and (B) TGF-β by ELISA. Lung lysates prepared on the day of necropsy (PC 15) were analyzed for: (C) IFN-γ; (D) IL-6; (E) IL-10; (F) TGF-β; and (G) IL-4 by ELISA. Each bar or data point in the graph represents average VN titer or optical density values from three pigs±SEM. Alphabet 'a', 'b' and 'c' represents the statistical significant difference (p<0.05) between unvaccinated vs K-Ag, unvaccinated vs Nano-KAg, and K-Ag Vs Nano-KAg pigs, respectively.

K-Ag vaccinated pigs had significantly increased TGF-β levels in serum compared to other experimental groups at PC 0. Unvaccinated, virus challenged pigs also had an increased trend in serum TGF-β levels at both PC 7 and PC-15 (FIG. 3B). However, Nano-KAg vaccinated pigs had significantly reduced TGF-β levels in serum at PC 7 and 15 (FIG. 3B). The proinflammatory cytokine, IL-6, in the lungs was significantly reduced in Nano-KAg and K-Ag immunized compared to unvaccinated pigs at PC 15. Moreover, reduction in IL-6 in Nano-KAg inoculated pigs was significantly lower than K-Ag immunized pigs (FIG. 3D). Both the immunosuppressive cytokines (IL-10 and TGF-β) and a Th2 cytokine, IL-4, in the lungs of Nano-KAg and K-Ag immunized pigs were significantly reduced compared to unvaccinated pigs at PC 15 (FIGS. 3 E, F and G).

Enhanced Th1 and Reduced Proinflammatory Recall Cytokines Response in Nano-KAg Vaccinated Pigs In LMNC, PBMC, BAL, and TBLN of Nano-KAg immunized pigs a significantly increased secretion of Th1 cytokines (IL-12 and IFN-γ) compared to unvaccinated virus challenged pigs was observed (FIG. 4A to H). Moreover, in PBMC, BAL, and TBLN cultures amount of secreted Th1 cytokines in Nano-KAg vaccinated pigs was significantly higher than K-Ag received pigs (FIG. 4A to H). In K-Ag received pigs the amounts of IFN-γ in the culture supernatant of BAL and TBLN cultures, and IL-12 in BAL cultures was significantly higher than unvaccinated virus challenged pigs (FIGS. 4CD and G).

Figure 4:
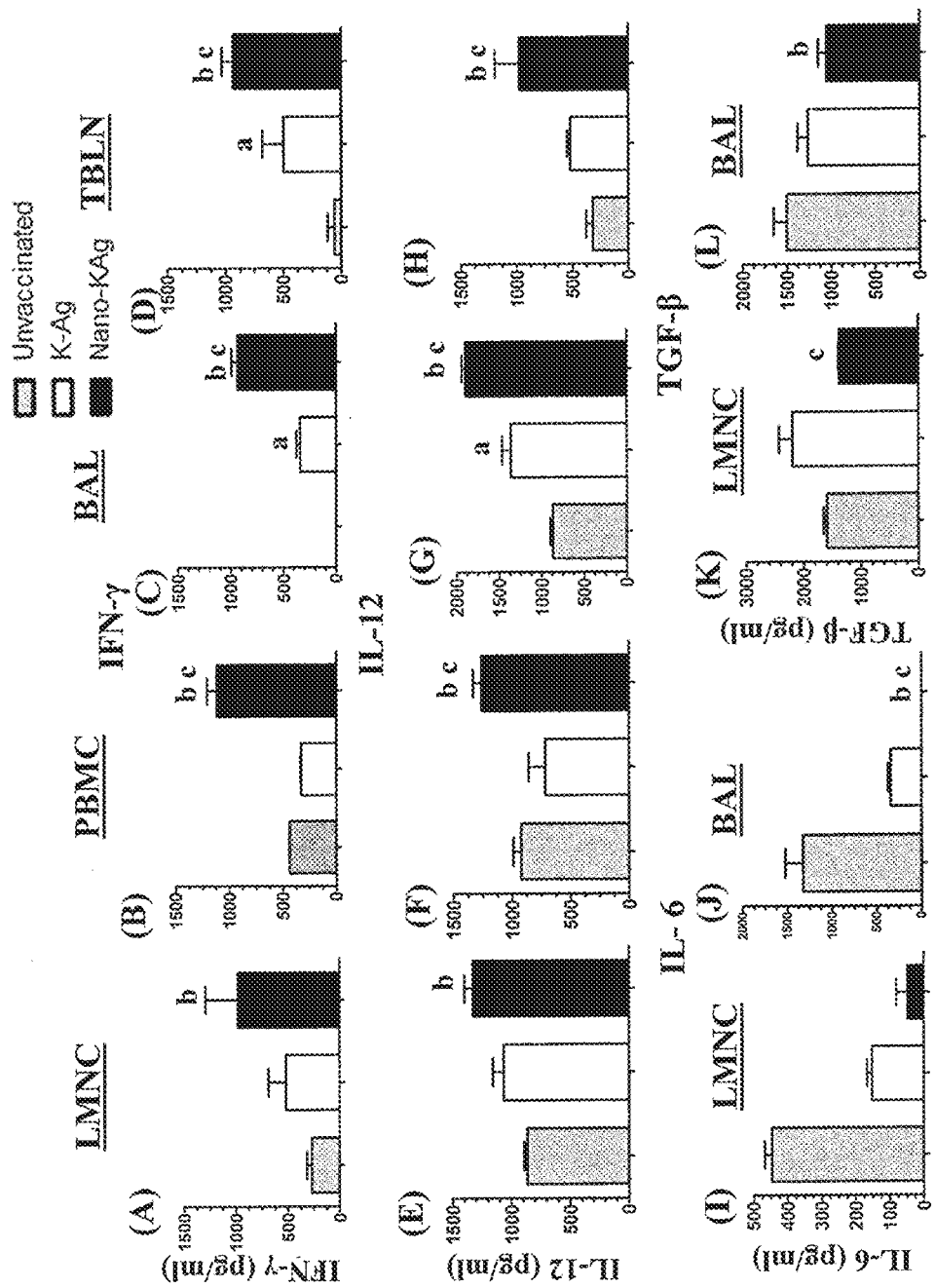
FIG. 4 shows analysis of PRRSV specific recall cytokine response. Indicated mononuclear cells were restimulated and the harvested culture supernatant was analyzed for cytokines by ELISA: (A to D) IFN-γ; (E to H) IL-12; (I and J) IL-6; and (K and L) TGF-β. Cytokines secreted by immune cells cultured in the absence of inactivated PRRSV was subtracted from the test values. Each bar in the graph represents average cytokine amount from three pigs±SEM. Alphabet 'a', 'b' and 'c' represents the statistical significant difference (p<0.05) between unvaccinated vs K-Ag, unvaccinated vs Nano-KAg, and K-Ag vs Nano-KAg pigs, respectively.

Secretion of proinflammatory cytokine, IL-6, in PBMC and LMNC of Nano-KAg immunized pigs was significantly less compared to unvaccinated and K-Ag immunized pigs (FIGS. 4I and J). The LMNC and BAL-MNC cultures of Nano-KAg immunized pigs secreted significantly less amounts of TGF-β compared to both the control groups (FIGS. 4 K and L).

Phenotypic Analysis of Different Immune Cells

Figure 5:
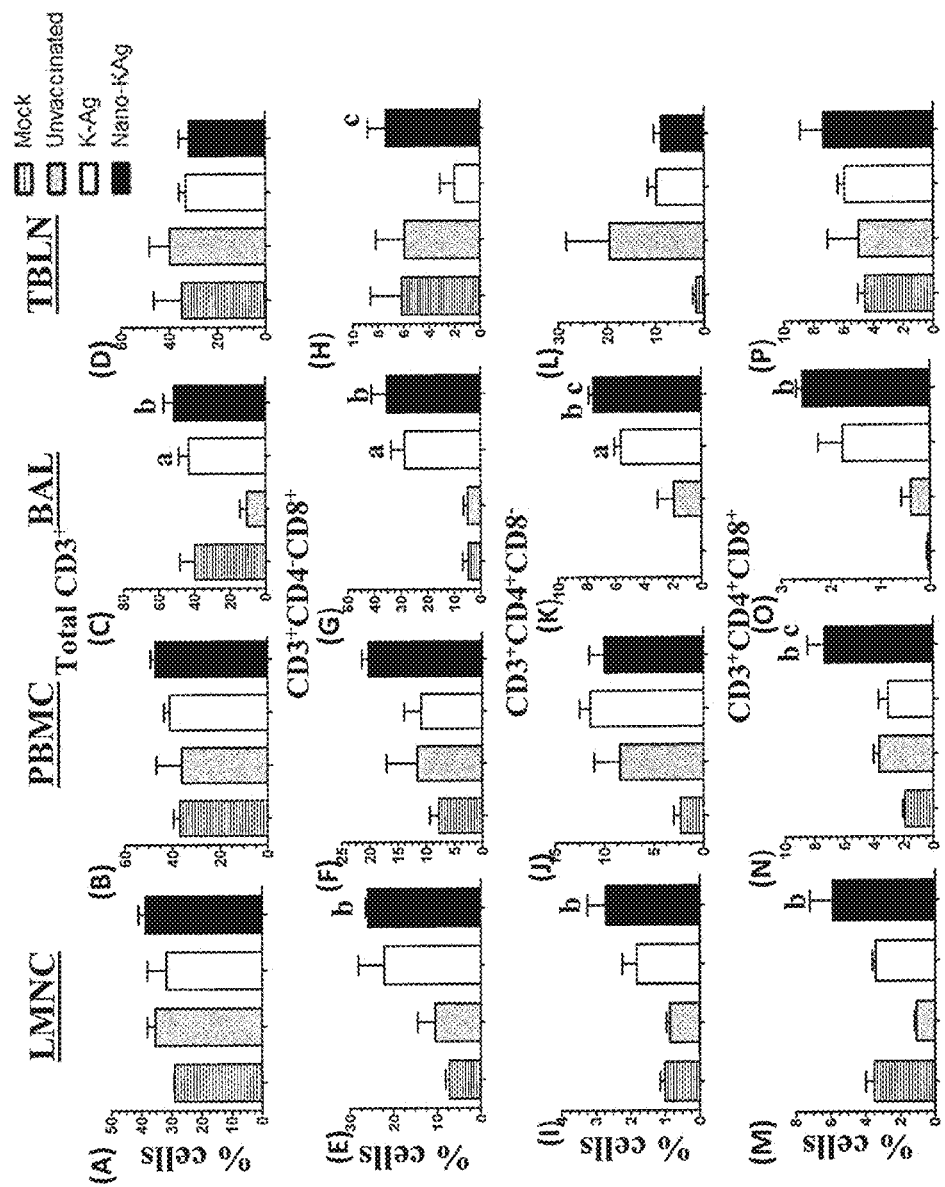
FIG. 5 shows cytometric analysis of CD and CD8 positive T cell subsets. Indicated mononuclear cells were immunostained to analyze the frequency of immune cells: (A to D) CD3$^+$ cells; (E to H) CD8$^+$ T cells; (I to L) CD4$^+$ T cells; and (M to P) CD4$^{+CD}$8$^+$ T cells. Each bar in the graph represents average percent of immune cells from three pigs±SEM. Alphabet 'a', 'b' and 'c' represents the statistical significant difference (p<0.05) between unvaccinated vs K-Ag, unvaccinated vs Nano-KAg, and K-Ag Vs Nano-KAg pigs, respectively.

Frequency of total lymphocyte population (CD3+) in BAL-MNC of Nano-KAg and K-Ag immunized pigs was significantly increased compared to unvaccinated group (FIG. 5C). In the LMNC of Nano-KAg immunized pigs, a significantly higher frequency of CD4+, CD8+, and CD4+CD8+ T cells compared to unvaccinated virus challenged pigs was detected (FIGS. 5F, J, and N). In BAL-MNC of Nano-KAg received pigs, a similar significant increase in lymphocyte subsets was observed. In addition, an increase in CD4+CD8+ T cells was significantly higher than K-Ag vaccinated pigs (FIG. 5K).

Figure 6:
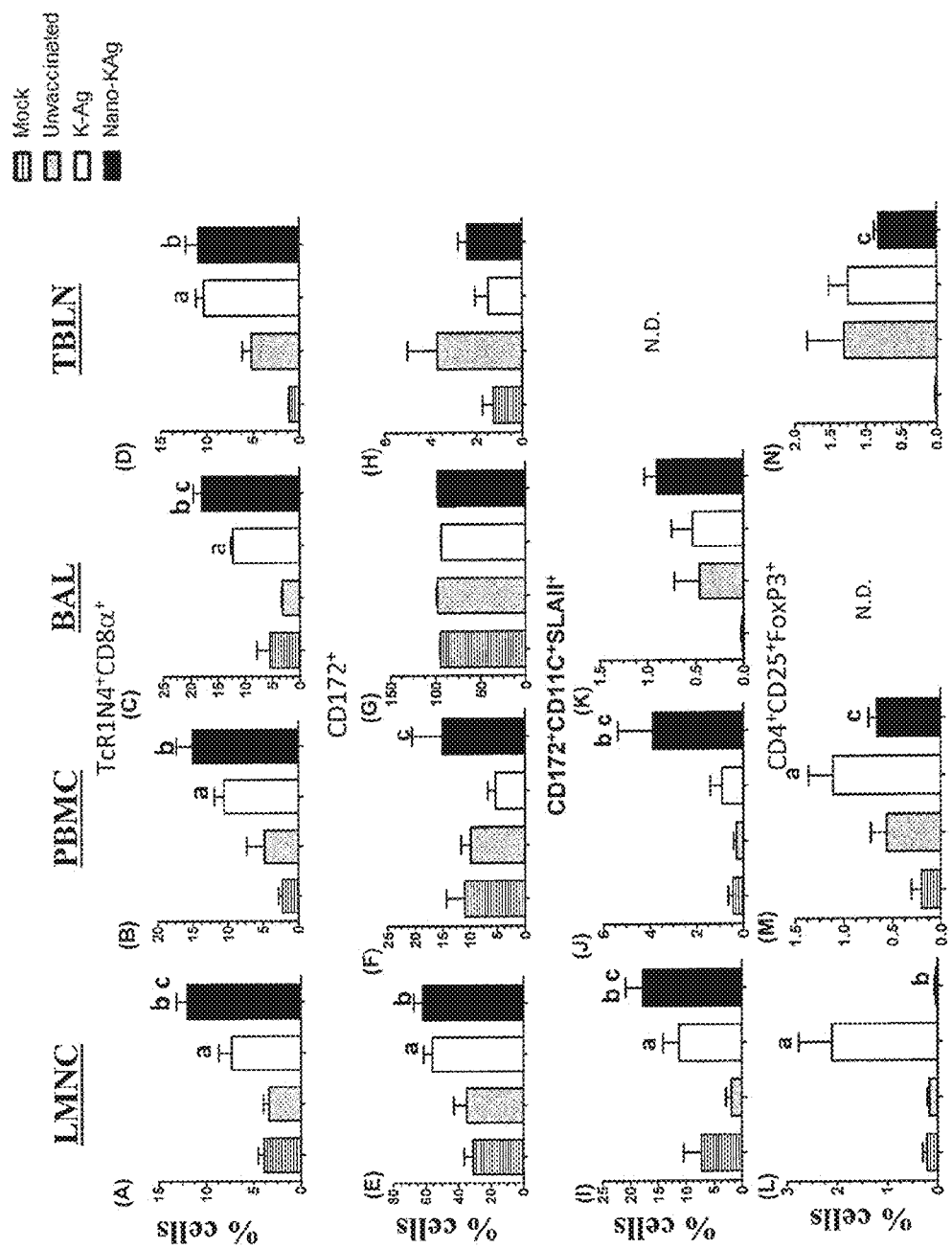
FIG. 6 shows cytometry analysis of innate and regulatory T cells. Indicated mononuclear cells were immunostained to determine the frequency of immune cells: (A to D) γδ T cells; (E to H) myeloid cells; (I to K) Dendritic cells rich fraction; and (L, M and N) Tregs. Each bar in the graph represents average percent of immune cells from three pigs±SEM. Alphabet 'a', 'b' and 'c' represents the statistical significant difference (p<0.05) between unvaccinated vs K-Ag, unvaccinated vs Nano-KAg, and K-Ag vs Nano-KAg pigs, respectively.

In Nano-KAg and K-Ag received pigs, frequency of T cells (TcR1N4+CD8+) in LMNC, PBMC, BAL, and TBLN-MNC was significantly higher compared to unvaccinated pigs (FIGS. 6ABC and D). In addition, their population in PBMC and BAL-MNC of Nano-KAg pigs was significantly higher than K-Ag vaccinated pigs (FIG. 6C). Myeloid cells and DCs rich fraction in PBMC and LMNC of Nano-KAg vaccinated pigs was significantly higher than K-Ag vaccinated pigs (FIGS. 6EFI and J). Also in LMNC of both Nano-KAg and K-Ag vaccinated pigs, myeloid cells and DCs rich fraction was significantly higher than unvaccinated pigs (FIGS. 6E and I). However, no alterations in myeloid cells and DCs rich fraction in BAL and TBLN (FIGS. 6GH and K) were found.

Frequency of Tregs in LMNC was significantly lesser in Nano-KAg immunized compared to unvaccinated pigs (FIG. 6L). While in pigs immunized with K-Ag, a significantly higher frequency of Tregs in LMNC compared to unvaccinated group was detected (FIG. 6L). Tregs frequency in PBMC in Nano-KAg immunized pigs compared to either control groups was significantly reduced (FIG. 6M). Also in TBLN of Nano-KAg immunized pigs significantly reduced population of Tregs compared to K-Ag immunized pigs was detected (FIG. 6N).

In spite of regular use of existing PRRSV vaccines prevention and control of the disease has remained as a challenge. There are outbreaks of PRRS in live vaccine immunized pig herd associated with isolation of reverted virus in unvaccinated sows in the same farm premises was reported (32, 96, 97).

PRRSV neutralizing antibodies protect pigs against viremia, virus replication in the lungs, transplacental spreading of the virus, and reproductive failure (98, 99). But the available killed PRRSV vaccines induce negligible VN antibody titers (35, 36, 100). A study has demonstrated that it is possible to elicit increased VN antibodies to a killed PRRSV vaccine by inactivating the virus using UV or binary ethylenimine (BEI), and co-administering the vaccine with a potent adjuvant (100). Each dose of UV or BEI treated vaccine had $1\times10^8$ TCID50 of the sucrose gradient purified PRRSV (100). As disclosed herein, each vaccine was having approximately $5\times10^6$ TCID50 of UV-treated PRRSV. This shows the advantage of using nanoparticle-mediated mucosal delivery of killed PRRSV vaccine in pigs, wherein a single reduced viral dose elicited protective immune response.

Incomplete anti-PRRSV immunity in immunized and infected pigs was associated with low levels of IFN-γ production (77). Enhanced IFN-γ response and antigen specific T-cell response (CD4+ and CD8+ T cells) is the hallmark of anti-PRRSV immunity (104, 105). A significant increase in IFN-γ levels and CD4+ and CD8+ T cell population in the lungs and blood of Nano-KAg vaccinated pigs were detected. T lymphocyte subset with CD4+CD8+ phenotype were abundant in pigs and they possess memory, T-helper, and cytolytic properties (106). In Nano-KAg immunized pigs, there was a significant increase in the population of $CD4^+CD8^+$ T cells in the lungs and blood. In pigs infected with an European strain of PRRSV a negative correlation between the frequency of $CD4^+CD8^+$ T cells and viremia was reported at 14 and 24 days post-infection, indicating their protective role in anti-PRRSV immunity (107). Recall cytokine responses in LMNC, PBMC, BAL, and TBLN-MNC of Nano-KAg immunized pigs revealed secretion of significantly increased Th1 cytokines (IFN-γ and IL-12). The cytokine, IL-12, plays an important role in host defense against viral infections (108).

A significant reduction in immunosuppressive cytokines (IL-10 and TGF-β) in the lungs of Nano-KAg immunized pigs was associated with enhanced IFN-α production both in the lungs and blood. In pigs, IL-10 reportedly inhibits IFN-γ production by T cells (109), and its immunosuppressive function with reduced IFN-γ production was reported in PRRSV infected pigs (77, 78). Infiltration of Tregs in infected pig lung microenvironment contributes to secretion of high levels of IL-10 and TGF-β (75). An increased frequency of Tregs in PRRSV infected pigs was reported (48, 110); but in Nano-KAg (but not K-Ag) immunized pigs a reduction in Tregs population in LMNC, PBMC, and TBLN was observed. Pigs possess a relatively large population of γδ T cells, and they are considered as an important innate immune cell at mucosal sites (111). In PRRSV infected pigs γδ T cells secrete IFN-γ (73). In Nano-KAg vaccinated pigs, there was an increased frequency of γδ T cells in the lungs, blood, and TBLN, indicating the protective role played by γδ T cells in PRRSV immunity.

In conclusion, the nanoparticle-mediated intranasal delivery of killed PRRSV vaccine elicits protective systemic and mucosal immune responses against PRRSV, and can clear the viremia early post-infection.

Example 2

Biodegradable Nanoparticle-Entrapped Vaccine Induces Cross-Protective Immune Response Against a Virulent Heterologous Respiratory Viral Infection in Pigs Material and Methods
Cells, PRRSV and Biodegradable Polymer A stable *Mycoplasma*-free MARC 145 cells (African Green monkey kidney cell line) which supports the growth of PRRSV (37) were used to prepare PRRSV stocks, killed viral Ags, and for immunological assays. Cells were maintained in Dulbecco's minimum essential medium (DMEM, Lonza) with 10% fetal bovine serum (Atlanta Biologicals) at 37° C. with 5% CO2. For virus infection and titration, the infection medium used was DMEM supplemented with 2% horse serum. The North American prototype PRRSV strain VR2332 (was used to prepare the vaccine, and for viral challenge studies an antigenically highly divergent virulent heterologous PRRSV strain MN184 (38) was used. For preparation of nanoparticles, PLGA [poly (DL-lactide-co-glycolide) 50:50, mol. wt. 40-75 kDa), polyvinyl alcohol (mol. wt. 30-70 kDa) (Sigma-Aldrich), Dicholoro methane (Acros Organics), and BCA protein assay kit (Pierce) were used.

Preparation of PRRSV Ags

MARC-145 cell-monolayer (>90% confluent) was infected with the VR2332 strain (38) at 0.001 MOI (multiplicity of infection) in roller bottles or T150 tissue culture flasks, and freeze-thawed three times after cells showed more than 80% cytopathic effect (approximately 3-4 days). Harvested infected cell culture fluid was clarified at 2000×g for 15 minutes and ultracentrifuged with a 20% sucrose overlay at 100,000×g for 2 hr at 40° C. Pooled crude viral pellet was suspended in sterile PBS and titrated to determine the viral titer, and UV irradiated (254 nm for 1 hr) to inactivate the virus, sonicated (probe sonicator at 80% amplitude, 30 seconds for 3 cycles), and the protein content was estimated using BCA kit (Biorad). Crude virus pellet was aliquoted and stored at −70° C. Control antigen was prepared similarly using uninfected MARC-145 cells.

Preparation of PLGA Nanoparticle-Entrapped Killed PRRSV Vaccine (Nano-KAg)

Nanoparticles were prepared using standard double emulsion solvent evaporation technique (40, 39). Briefly, 15% of PLGA 50/50 (750 mg) was dissolved in 5 ml of dichloromethane, and 100 μl of killed VR2332 proteins (5 mg) was added. The mixture was homogenized using a Brinkman Polytron homogenizer at 6000 rpm for 90 seconds. The homogenized mixture was added to aqueous solution of polyvinyl alcohol (10% PVA), and homogenized for 5 min. Finally, the preparation was stirred at room temperature (RT) overnight to allow solvent evaporation; and the nanoparticles were washed in distilled water three times by centrifugation at 11,000×g, freeze-dried and stored at 4° C.

Determination of Entrapment Efficiency of PRRSV Proteins in Nanoparticles

The amount of entrapped PRRSV protein in the nanoparticles was determined as described previously (41). Briefly, freeze-dried Nano-KAg (10 mg) was treated with 0.1N NaOH for 1 hr at 37° C., vortexed and the harvested supernatant was collected and analyzed for protein concentration, including a series of BSA standards prepared in 0.1 N NaOH in a BCA protein assay kit (Pierce, USA).

Determination of Morphology of PLGA Nanoparticles

The size and shape of nanoparticles was determined by scanning electron microscopy (Hitachi S-3500N). Briefly, freeze-dried nanoparticles were mounted on an adhesive stub coated with gold-platinum under vacuum using an ion coater, and examined under the microscope at 10 KV.

Characterization of Nano-KAg by Confocal Microscopy

Bronchoalveolar lavage fluid (BAL) collected from three 4-6 weeks old healthy SPF pigs was processed to isolate mononuclear cells (BAL-MNC) (42). BAL-MNC plated at a concentration of $1\times10^6$ per ml in a 24 well plate containing poly-L-lysine coated cover slips were incubated at 37° C. in 5% CO2 incubator for 1 hr. Non-adherent cells were aspirated and the coverslips with adherent cells were washed gently with PBS and used in the study. Freeze-dried Nano-KAg containing different concentrations of PRRSV proteins (0.2 µg/ml) was suspended in DMEM containing 10% FBS and added into a plate containing BAL cells and incubated for 3 hr at 37° C. BAL-MNC, either uninfected or infected with PRRSV (MN184 strain) at 0.1 MOI for 12 hr was included in the assay. Cells were fixed in 3% paraformaldehyde for 15 min on ice, permeabilized (0.1% Triton X-100 for 15 min) and blocked (PBS containing 5% BSA and 0.2% triton X-100 for 1 hr at RT). Subsequently, cells were treated with anti-PRRSV nucleocapsid specific mAb SDOW17 (Rural Technologies, Inc.) and early endosome cross-reactive anti-pig human antibody (Santa-Cruz) in PBS containing 1% BSA and 0.1% triton X-100 for 1 hr at RT. Followed by treatment with goat anti-mouse IgG Alexa Flour488 and donkey anti-goat Alexa flour 633 (Invitrogen) and incubated for 1 hr at RT. Cells were washed in between the treatment steps and treated with a mounting medium containing 2.5% DABCO (Sigma). Stained coverslips were mounted on a clean glass slide using transparent nail polish and viewed under a Leica confocal microscope. The acquired images were analyzed using Leica confocal software. BAL-MNC plated at a concentration of $1\times10^6$ per 96-well in a U-bottom plate treated and stained in a similarly also gave comparable results.

In Vitro Uptake of Nano-KAg by Pig Mφs and Determination of CD80/86 Expression by Flow Cytometry BAL-MNC were seeded in a 24 well plate at a density of $1\times10^6$ per ml and untreated or treated with K-Ag or Nano-KAg (containing a 2, 0.2, and 0.02 µg/ml of PRRSV protein) and incubated for 3 hr at 37° C. in a 5% $CO_2$ incubator. Cells uninfected or infected with PRRSV (MN184 strain) at 0.1 MOI for 12 hr at 37° C. in 5% $CO_2$ incubator served as controls. Cells were treated with anti-PRRSV N' mAb followed by goat anti-mouse IgG Alexa Flour488, washed and fixed before analysis. To assess the expression of CD80/86 on professional antigen presenting cells (APCs), BAL-MNC were treated as above for 16 hr at 37° C. in 5% $CO_2$ incubator, washed and stained using biotinylated human CTLA4-mouse immunoglobulin fusion protein (Ancell, MN) and PE-conjugated CD172 (Southern Biotech) (43), followed by streptavidin percpcy5.5. Cells were fixed using 1% paraformaldehyde and analyzed using FACS Aria II (BD Biosciences) flow cytometer.

Pigs and Inoculations

Conventional large White-Duroc crossbred weaned specific-pathogen-free pigs at 3-4 wks of age were transported to a BSL-2 facility, FAHRP, OARDC. The swine-herd was confirmed seronegative for antibodies to PRRSV, porcine respiratory corona virus, transmissible gastroenteritis virus, and porcine Circo virus 2. Blood samples collected from pigs on arrival was confirmed negative for PRRSV antibodies. Pigs were allowed to acclimate for an additional week, they received food and water ad libitum and maintained under the supervision of a veterinarian.

In a pre-challenge study, pigs (n=9) were grouped randomly into three groups (n=3 per group). Group I—mock pigs inoculated with DMEM and PBS; Group II—inoculated with K-Ag; Group III—inoculated with Nano-KAg, inoculated once intranasally. Each vaccine (Nano-KAg and K-Ag) dose has one mg of crude viral preparation containing $\sim5\times10^6$ $TCID_{50}$ of inactivated virus. All the pigs were euthanized on day post-immunization (DPI) 15 and evaluated for innate and the PRRSV specific immune responses. In a post-challenge study, pigs (n=12) were divided randomly into four groups (n=3 per group). Group I—mock pigs; Group II—inoculated with normal saline; Group III—inoculated with K-Ag; Group IV—inoculated with Nano-KAg. Each vaccine dose had same amount of Ags as described above. Groups II, III, and IV were challenged with PRRSV MN184 ($0.5\times10^6$ $TCID_{50}$/ml, 2 ml per pig) on DPI 21 and euthanized on day post-challenge (DPC or PC) 15. All the inoculations were performed once by intranasal route. Mock-inoculated pigs were separately euthanized before sacrificing virus challenged animals.

(1) Gross and Histological Analysis

Necropsies were performed on all of the pigs and the lungs and lymph nodes were examined grossly and histologically. Macroscopic pulmonary lesions were given an estimated score based on the percentage of consolidated lesions in individual lobes as described previously (44). The lung tissue samples collected from the caudal lobe was fixed in 10% neutral buffered formalin, processed into paraffin blocks, cut into sections (3 µm) and stained using hematoxylin-and-eosin (H&E) as described previously (44). Frozen lung sections (3 µm) were immunostained as described previously (45). Briefly, sections were dewaxed, dehydrated, quenched, washed in PBS, blocked using 2% goat serum, and treated with PRRSV nucleocapsid protein specific mAb (SDOW17) (Rural Technologies, Inc.,) or isotype control mAb. The sections were treated with ABC peroxidase staining kit (Vectastain Elite, Vector Labs) and the labeling was "visualized" by application of DAB (3,3'-diaminobenzidine) substrate (Vector Laboratories) and counterstained with hematoxylin. Immunostained lung slides were examined by an unbiased certified veterinary pathologist to score for the presence of PRRSV Ags.

Collection of Blood and Lung Samples for Analysis

For evaluation of viremia and for titration of PRRSV specific serum neutralizing antibodies, 3 to 5 ml of blood samples were collected on DPI 0 and 21, and DPC 7 and 15. Separated serum was aliquoted and kept at −20° C. Lung homogenates were prepared for cytokine and virus evaluation as described earlier (46, 12).

Isolation of PBMC, Lung MNC, and TBLN Cells

To isolate PBMC, blood was collected in acid citrate dextrose solution from euthanized pigs and processed as described (47). Lung-mononuclear cells (lung MNC/LMNC) from individual pigs were isolated as per the described procedure (48). The airways were lavaged to collect BAL cells using sterile ice cold PBS containing EDTA (0.03%) (49). Samples of tracheobronchial lymph nodes (TBLN), iliac lymph nodes (ILN), and tonsils were collected in DMEM, and MNCs were isolated as described previously (48).

Virus Titration and Virus Neutralizing Test (VNT)

PRRSV titer and virus neutralizing antibody titer in serum and in lung lysate was analyzed by indirect immunofluorescence assay (IFA) as previously described (37). Briefly, for virus titration confluent monolayer of MARC-145 cells in 96-well microtiter plate was treated with 10-fold dilution of serum for 48 hr. To measure VN titers in serum and lung lysates, samples were heat inactivated, UV treated, twofold diluted, and incubated with an equal volume of PRRSV (MN184) 250 TCID50 per well for 2 hr at 37° C. One hundred microliters of the suspension was transferred into 96-well plate containing confluent monolayer of MARC-145 cells, incubated for 24 hr at 37° C. in a CO2 incubator. The cells were fixed with 80% acetone and stained with anti-PPRSV N'mAb (SDOW-17) and Alexa-488 conjugated anti-mouse IgG(H+L). Plates were mounted using glycerol-PBS and examined for viral plaques under a fluorescent microscope.

PRRSV Specific Isotype Antibody Analysis in the Lungs and Blood

The presence of PRRSV specific IgA and IgG antibodies in serum and lung lysate were analyzed by ELISA. Briefly, ELISA plates were coated with pre-titrated quantity of crude killed PRRSV (MN184) Ags (10 µg/ml) in carbonate-bicarbonate buffer (pH 9.6) overnight at 4° C., washed and treated with blocking buffer (1% BSA and 0.1% Tween 20 in PBS) for 2 hr at RT; serum (1:100) and lung lysate (0.5 mg/ml, w/v) samples were added and incubated for 2 hr at RT. The bound virus specific isotype antibody was detected using anti-pig IgA and IgG secondary antibodies conjugated with HRP (KPL). Finally, plates were developed using the chromogen TMB and read at 450 nm. To eliminate the background activity, non-PRRSV specific antigen-coated control plates were also included, blocked and treated with test samples side-by-side. The OD values obtained from experimental plate were subtracted from the control plate.

PRRSV Specific Recall Cytokine Response

Five million pig PBMC, TBLN MNC, and lung MNC were subjected to ex vivo restimulation in the absence or presence of killed crude PRRSV MN184 Ags (50 µg/ml) as described previously (48), and the harvested supernatant was analyzed to measure cytokines Cytokines secreted by immune cells cultured in the absence of PRRSV Ags was subtracted from the corresponding test value.

Analysis of Cytokine Response and Flow Cytometric Analysis of Immune Cells

Serum samples, harvested culture supernatants, and lung lysates were analyzed for Th1 (IFN-γ and IL-12), Th2 (IL-4), pro-inflammatory (IL-6), and immunosuppressive (IL-10 and TGF-β) cytokines by ELISA (48). Amount of cytokines present in the lung lysate was normalized to picogram per gram of lung tissue. Flow cytometry analysis was performed to determine the phenotype and the frequency of different immune cells by a multicolor immunoassay as described previously (48). Briefly, 50,000 events of immunostained cells were acquired using a FACS Aria II (BD Biosciences) flow cytometer and analyzed using FlowJo software (Tree Star, Inc.,). The analysis was done to determine different immune cell populations based on the following phenotypes: NK cell rich fraction (CD3−CD4−CD8+); T-helper cells (CD3+CD4+CD8−); CD8+ T cells (CD3+CD4−CD8+]; T-helper/memory cells (CD3+CD4+CD8+); γδ T cells (CD8+TcR1N4+); T-regulatory cells (CD4+CD25+Foxp3+); myeloid cells (CD172+); and dendritic cell rich fraction (CD172+CD11C+SLAII+).

Statistical Analysis

All data were expressed as the mean of three pigs+/−SEM. Statistical analyses were performed using one way analysis of variance (ANOVA) followed by post-hoc Tukey's test using GraphPad InStat (software version 5.0) to establish differences between K-Ag and Nano-KAg pig groups. Statistical significance was assessed as $P<0.05$.

Results

In Vitro Characterization of PRRSV Entrapped-Nanoparticles

Figure 7:
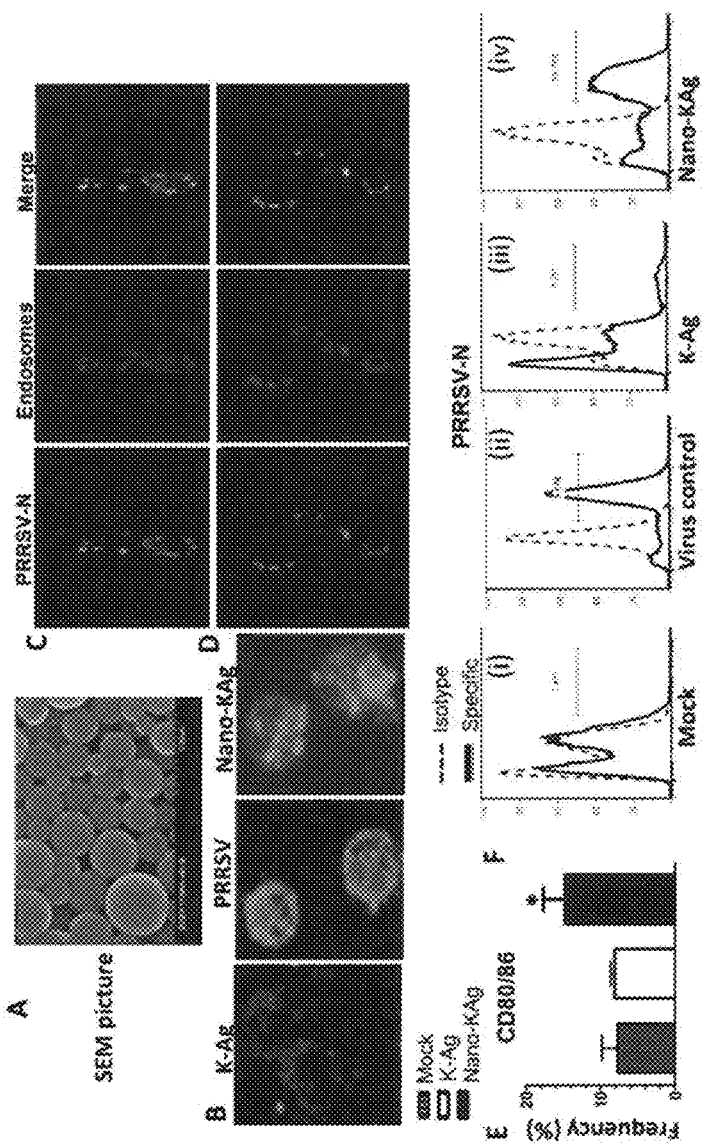
FIG. 7 shows characterization of Nano-KAg in pig alveolar Mφs in vitro. (A) Scanning electronic photomicrograph of PRRSV Ags entrapped PLGA nanoparticles prepared by a standard multiple emulsion method. Confocal microscopy pictures: (B) Mφs were treated with killed PRRSV (K-Ag), Nano-KAg, or infected with PRRSV and then treated with PRRSV N' protein specific mAb followed by Alexa 488 anti-mouse antibody; Co-localization of PRRSV N protein in endosomes of Mφs, (C) Nano-KAg treated and (D) PRRSV infected. (E) Upregulation of CD80/86 in myeloid cells (CD172$^+$) treated with Nano-KAg. Each bar represents average percent of Mφs positive for CD80/86 marker in mock, K—Ag and Nano-KAg treated BAL cells harvested from three pigs+/−SEM. Asterisk represents the statistical significant difference (p<0.05) between Nano-KAg and K-Ag received pig groups. (F) Representative histogram showing the presence of PRRSV-N protein in Mφs treated as indicated. Similar results were obtained in three independent trials.

Morphology of sham and PRRSV Ags entrapped PLGA nanoparticles was determined by scanning electron microscopy (SEM) which revealed the size of particles to be 200-600 nm (FIG. 7A). The average protein content in nanoparticles or core-loading was 0.50-0.55% (w/w), which represents an encapsulation efficiency of 50-55%. Upon re-dispersion of the Nano-KAg in PBS, PRRSV proteins were released slowly in the first 48 hr, later a gradual release profile was observed over the next 5-weeks.

Uptake of Nano-KAg by APCs was studied using BAL-MNC harvested from three healthy SPF pigs. The confocal images revealed preferential uptake of Nano-KAg by APCs but not unentrapped viral Ags (K-Ag), and PRRSV infected cells served as a positive control (FIG. 7B). Engulfed nanoparticles delivered the PRRSV Ags to early endosomes and it was comparable to virus-infected control (FIGS. 7C & D). Further, Nano-KAg engulfed APCs underwent maturation as indicated by significantly increased expression of CD80/86 on APCs compared to K-Ag treated cells (FIG. 7E). In addition, 57% BAL-MNC treated with Nano-KAg were positive for PRRSV protein comparable to virus infected cells (FIG. 7F ii & iv). In contrast, only 9% BAL-MNC treated with K-Ag were positive for viral protein (FIG. 7F iii). The results show that PRRSV Ags delivered in nanoparticles were phagocytosed by APCs and the released protein was found inside the endosomes.

Potential of PRRSV Ags Entrapped Nanoparticle (Nano-KAg) as a Candidate Vaccine

Figure 8:
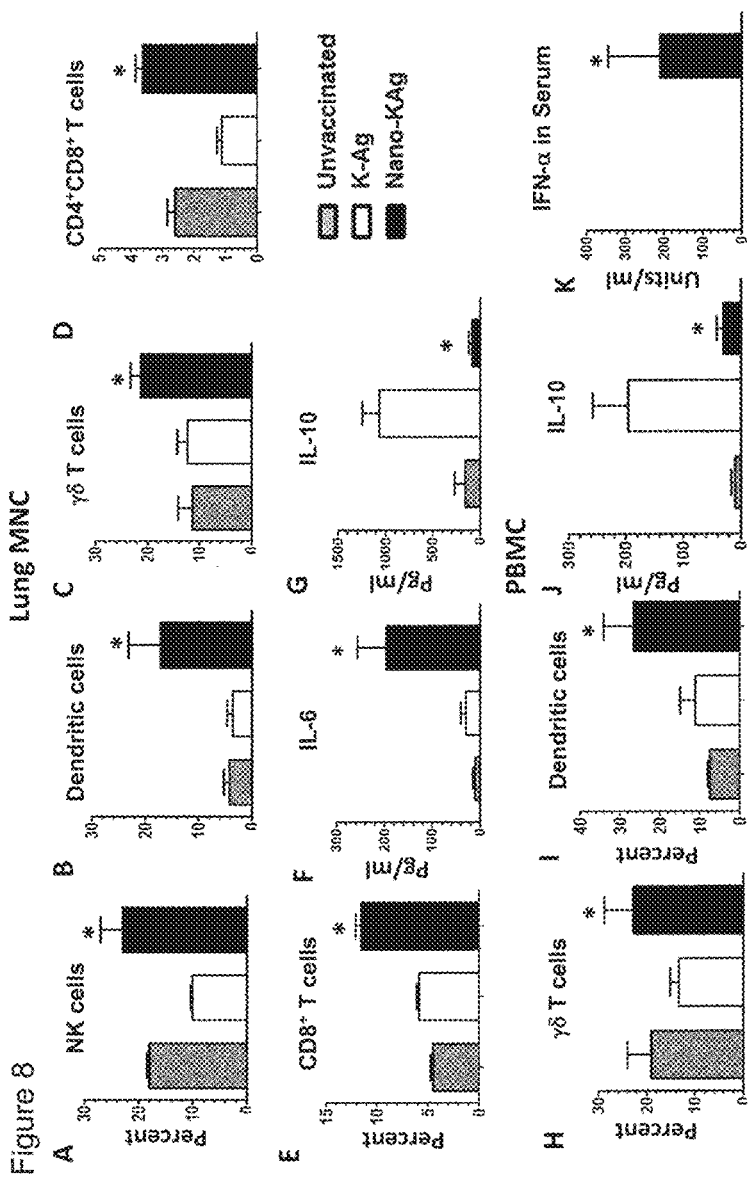
FIG. 8 shows Nano-KAg elicited enhanced innate and suppressed regulatory response in a pre-challenge study. Pigs were unvaccinated or vaccinated with either K-Ag or Nano-KAg once intranasally. Immunostained to analyze the frequency of immune cells: (A) NK cells, (B) Dendritic cells, (C) γδ T cells, (D) Th/memory cells, (E) CD8+ T cells in Lung MNC; and (H) γδ T cells and (I) Dendritic cells in PBMC. Harvested culture supernatants from restimulated immune cells were analyzed for cytokines (F) IL-10 and (G) IL-6 in lung MNC; and (J) IL-10 in PBMC; also (K) IFN-α in serum by ELISA. Each bar represents the average amounts from three pigs±SEM. Asterisk represents the statistical significant difference (p<0.05) between Nano-KAg and K-Ag received pig groups.

In a pre-challenge study, intranasal delivery of Nano-KAg resulted in induction of innate immune response at both mucosal and systemic sites, indicated by a significant increase in the frequency of NK cells, DCs, and γδ T cells. In addition, immune cells involved in adaptive arm of the immunity, such as Th/memory cells and CD8+ T cells were increased significantly in the lungs of Nano-KAg compared to K-Ag immunized pigs (FIG. 8 A-E). Similarly, PBMC of Nano-KAg vaccinated pigs showed a significant increase in the frequency of γδ T cells and DCs (FIGS. 8 H & I). Interestingly, K-Ag vaccinated pigs had a reduction in the frequency of NK cells and Th/memory cells in the lungs (FIGS. 8 A & D). Further, lung MNC and PBMC from Nano-KAg immunized pigs secreted significantly reduced levels of the cytokine IL-10, and higher amounts of IL-6 in a recall response (FIG. 8 F, G, J). In addition, innate cytokine IFN-α was secreted in pigs immunized with Nano-KAg and not K-Ag (FIG. 8K).

Figure 9:
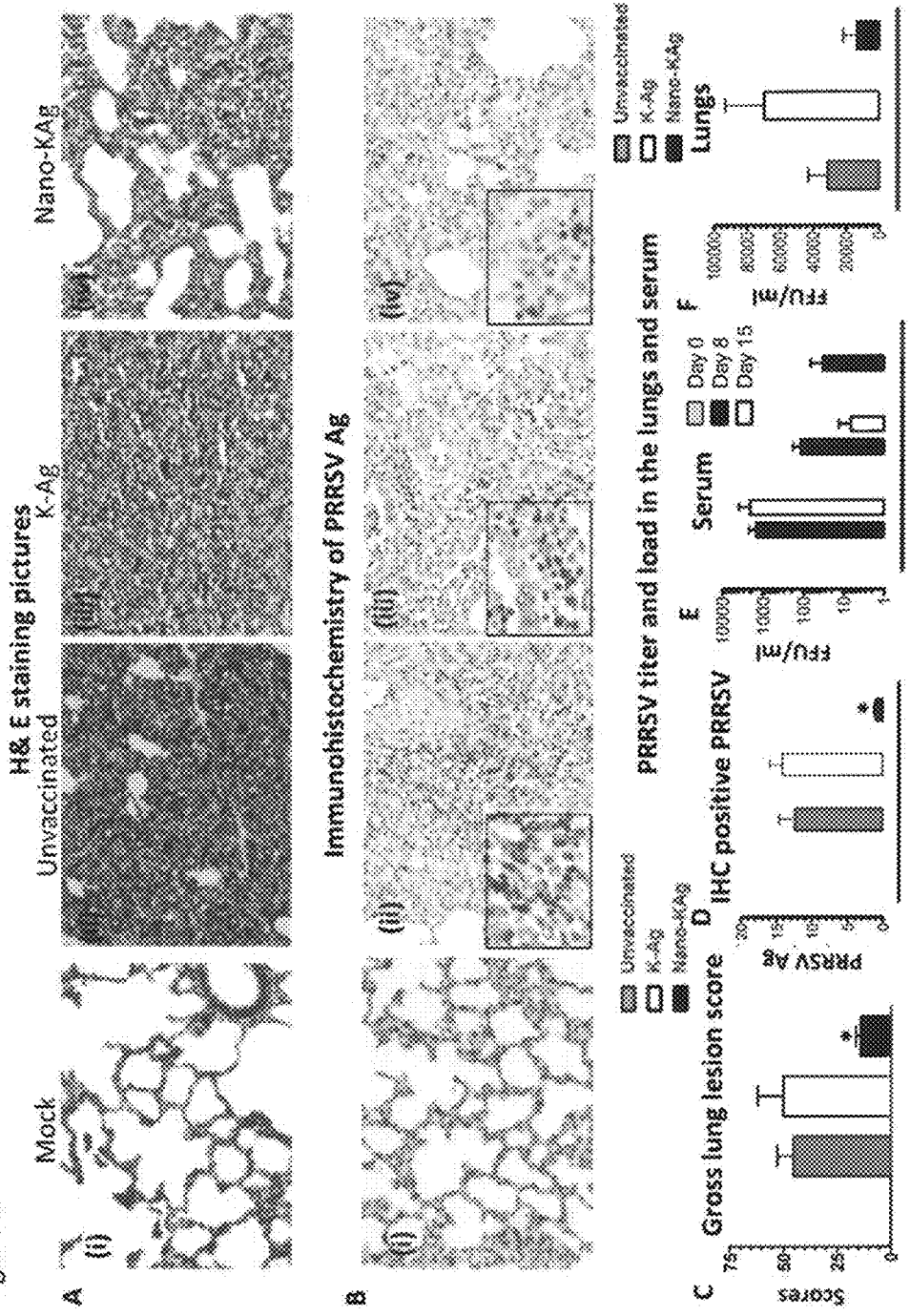
FIG. 9 shows reduced lung pathology and viral load in Nano-KAg vaccinated MN184 challenged pigs. Pigs were unvaccinated or vaccinated with either K-Ag or Nano-KAg once intranasally, challenged with PRRSV MN184 strain at PID 21 and euthanized at DPC 15. (A) A representative pig lung H&E picture from indicted pig group. (B) A representative lung immunohistochemistry (IHC) picture from indicted pig group showing PRRSV N antigen positive cells (asterisk in the magnified image) stained by Nova red. (C) Gross lung lesions were graded based on percentage of the lung area affected and severity of inflammatory pathology. (D) PRRSV N antigen positive cells in IHC were counted in 10 random fields from each pig. The PRRSV titer in fluorescence foci units at indicated DPC in (E) serum, and (F) in the lungs at DPC 15 was determined by immunofluorescence assay. Each bar represents average values from three pigs±SEM. Asterisk represents the statistical significant difference (p<0.05) between Nano-KAg and K-Ag received pig groups. A similar trend in results was obtained in an independent second trial.

Significant Reduction in the Lung Pathology and Virus Load in Nano-KAg Vaccinated Pigs Initially, dose-dependent response to the Nano-KAg candidate vaccine was performed in vivo in pigs using doses of 0.2 and 1 mg per pig ($\sim 1\times10^6$ and $5\times10^6$ TCID50 of inactivated virus), and detected appreciable immune response with one mg dose. Therefore, all the subsequent trials were performed with a dose of one mg per pig. In a post-challenge study, Nano-KAg immunized MN184 challenged pigs were clinically healthy with no fever or respiratory distress. In contrast, both K-Ag and unvaccinated, MN184 virus challenged pigs had fever with reduced feed intake during the first week post-challenge. During necropsy, significantly reduced gross lung lesions were observed in the Nano-KAg immunized group compared to other two virus challenged groups (FIG. 9C). Microscopic examination of H&E stained lung sections of unvaccinated and K-Ag vaccinated, MN184 challenged pigs had severe pneumonic lesions with massive infiltration of mononuclear cells with large infected area. In contrast, significantly reduced lung lesions were observed in Nano-KAg immunized virus challenged pigs (FIG. 9A).

Figure 10:
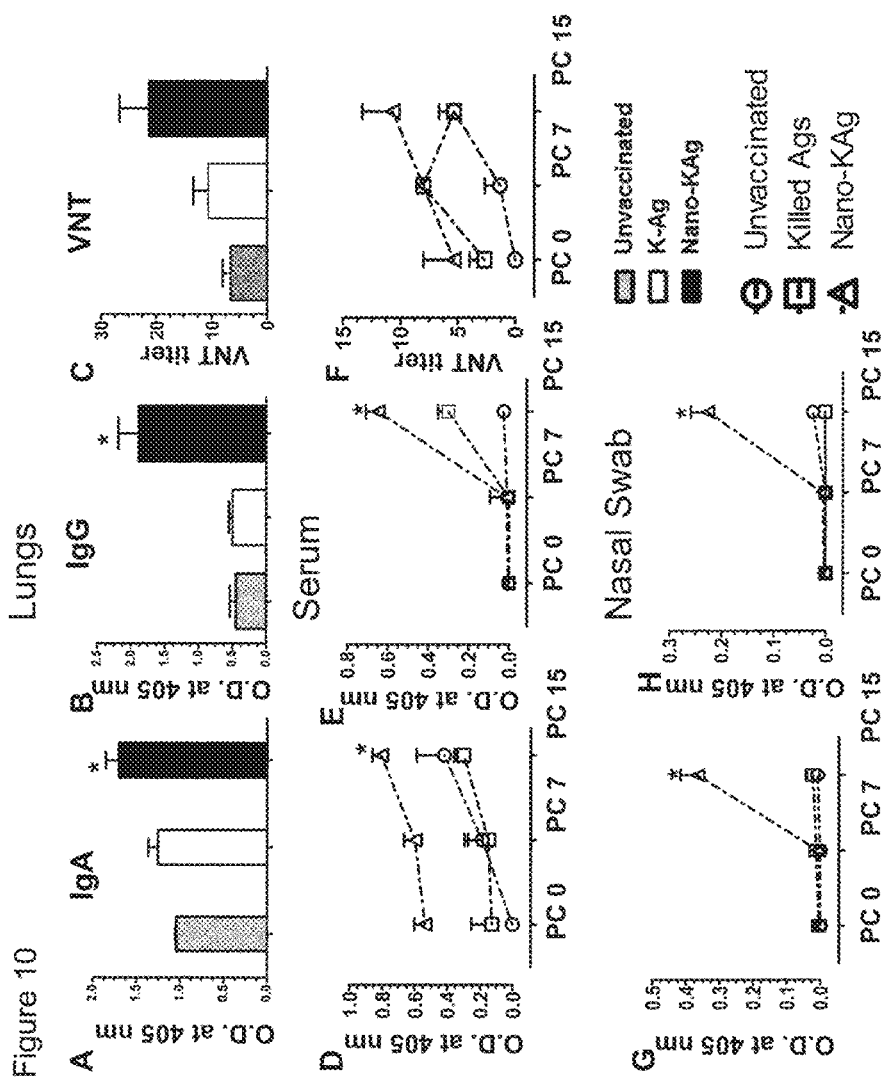
FIG. 10 shows enhanced PRRSV specific IgA and neutralizing antibody response in Nano-KAg vaccinated MN184 strain challenged pigs. Pigs were unvaccinated or vaccinated with either K-Ag or Nano-KAg once intranasally, challenged with PRRSV MN184 strain at PID 21 and euthanized at DPC 15. Anti-PRRSV IgA antibody response in (A) lungs, (D) serum, and (G) nasal swabs; and IgG antibody response in (B) lungs, (E) serum, and (H) nasal swabs was determined by ELISA. PRRSV neutralizing antibody response in (C) lungs and (F) serum was determined by immunofluorescence assay. Each bar represents average optical density value or VN titer from three pigs±SEM. Asterisk represents the statistical significant difference (p<0.05) between Nano-KAg and K-Ag received pig groups. A similar trend in results was obtained in an independent second trial.

Immunohistochemistry analysis has revealed abundant inactivated PRRSV positive cells in the lung sections of unvaccinated and K-Ag immunized, MN184 virus challenged pigs compared to Nano-KAg pig group (FIGS. 10 B&D). PRRSV virus titer in serum samples and lung homogenate has indicated reduced viral load by greater than one log at day post-challenge (DPC or PC) 7 with complete viral clearance by DPC 15 in Nano-KAg vaccinated pigs compared to K-Ag vaccinated and unvaccinated pigs (FIG. 9E). The K-Ag vaccinated pigs also cleared the viremia better than the unvaccinated pigs (FIG. 9E). Similarly, PRRSV load in the lungs was also reduced in Nano-KAg compared to K-Ag immunized, MN184 virus challenged pigs (FIG. 9F). Also the PRRSV titer values (TCID50/ml) in both the serum and lung homogenate showed a reduction in Nano-KAg immunized compared to control pigs.

Humoral Immune Response in Serum, Lungs and Nasal Swab

Lung homogenates of Nano-KAg immunized pigs contained significantly higher levels of secreted virus specific IgA and IgG antibodies compared to unvaccinated or K-Ag immunized, MN184 challenged pigs (FIGS. 10 A&B). In the serum samples of Nano-KAg immunized pigs increased IgA antibody levels at PC 0, with a significant increase at PC 15 compared to either unvaccinated or K-Ag immunized, MN184 challenged pigs was detected (FIG. 10D). The PRRSV specific IgG antibody levels in serum (FIG. 10E), and both IgA and IgG levels in the nasal swab (FIGS. 10G&H), were significantly higher in Nano-KAg immunized compared to K-Ag immunized pigs at DPC 15. Although increased PRRSV specific neutralizing antibody (VN) titers in the lungs and serum were detected at DPC 15, the data was not statistically significant (FIGS. 10 C&F).

Nanoparticle-Based PRRSV Vaccine Showed Enhanced Innate Immune Response in Pigs

Figure 11:
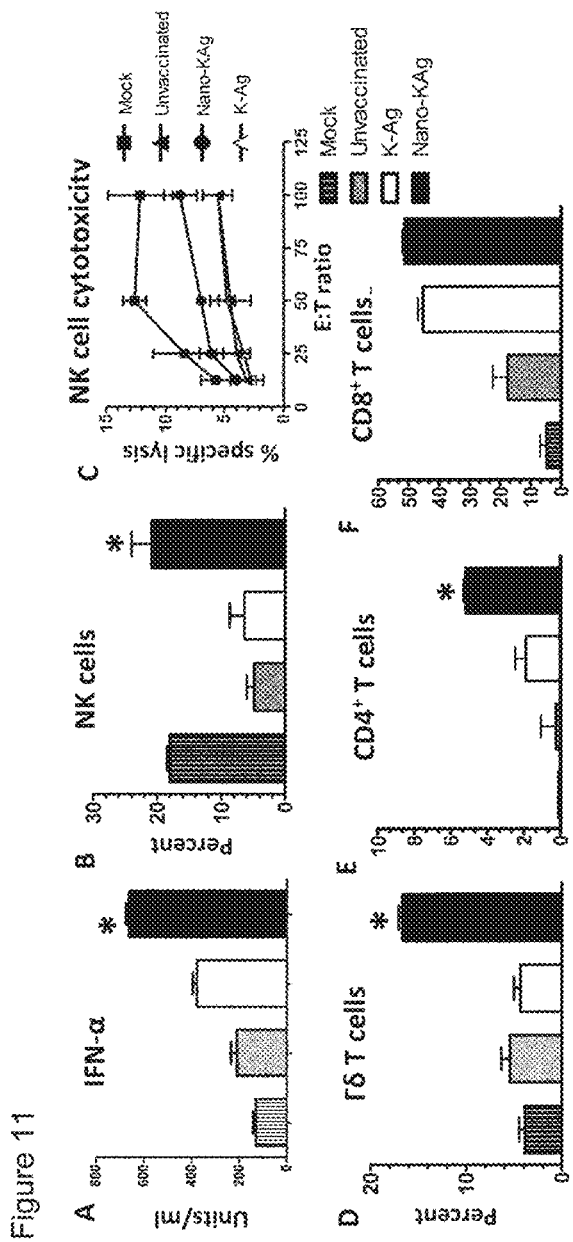
FIG. 11 shows Nano-KAg elicited enhanced innate immune response in the lungs of pigs. Pigs were unvaccinated or vaccinated with either K-Ag or Nano-KAg once intranasally, challenged with PRRSV MN184 strain at PID 21 and euthanized at DPC 15. Lung homogenate was analyzed for the cytokine (A) IFN-α by ELISA. Lung MNC were analyzed for (B) NK cells, (D) γδ T cells, (E) CD4+ T cells, and (F) CD8+ T cells by flow cytometry. (C) NK cells present in the lung MNC were analyzed from cytotoxic function by LDH assay. Each bar or data point in the graph represents average values from three pigs±SEM. Asterisk represents the statistical significant difference (p<0.05) between Nano-KAg and K-Ag received pig groups. A similar trend in results was obtained in an independent second trial.

Nano-KAg vaccine received MN184 virus challenged pigs had significantly increased innate IFN-α production in the lungs (FIG. 11A). In K-Ag immunized virus challenged pigs a fourfold reduction in NK cell frequency compared to mock pigs was detected; in contrast, in Nano-KAg vaccine inoculated pigs the NK cell population was comparable to mock pigs (FIG. 11B). Further, lung NK cell-cytotoxic function in unvaccinated and K-Ag immunized, MN184 virus challenged pigs was completely suppressed; however, in Nano-KAg received pigs it was partially decreased (FIG. 11C). The frequency of γδ T cells and CD4+(but not CD8+) T cells in the lungs of Nano-KAg vaccinated animals were significantly increased compared to K-Ag and unvaccinated, virus challenged pigs (FIGS. 11 DE&F). In the peripheral blood of Nano-KAg immunized pigs a significantly increased frequency of DCs, and in TBLN significantly increased frequency of both DCs and γδ T cells was observed (Table 1).

Table 1 shows pigs that were unvaccinated or vaccinated with either K-Ag or Nano-KAg once intranasally and challenged with PRRSV strain MN184 and euthanized on DPC 15. Different immune cell subsets present in PBMC and TBLN MNC were enumerated by flow cytometry. [a] $CD172^+$ cells were gated to enumerate CD11c and SLAII expression and the percent of DCs rich fraction ($CD172^+CD11c^+$ $SLAII^+$) is shown. [b] $CD3^+$ cells were gated to enumerate CD4 and CD8α expression and the percent of NK cell rich fraction ($CD3^-CD4^-$ $CD8α^+$) is shown. [c] $CD25^+$ cells were gated to enumerate CD4 and Foxp3 expression and the percent of $CD4^+CD25^+Foxp3^+$ cell is shown. Each number is an average percent of immune cells from three pigs+/−SEM. Asterisk represents the statistical significant difference ($p<0.05$) between Nano-KAg and K-Ag received pig groups.

TABLE 1

Frequency of immune cells in PBMC and TBLN of Nano-KAg vaccinated pigs.

| Immune cells | Mock | Unvaccinated | K-Ag | Nano- |
|---|---|---|---|---|
| PBMC | | | | |
| Myeloid cells | 21.1 ± 0.5 | 59.3 ± 4.3 | 69.9 ± 3.7 | 72.8 ± 2.5 |
| Dendritic Cells | 3.1 ± 0.6 | 0.01 ± 0.3 | 0.7 ± 0.1 | 3.03 ± 0.6* |
| γδ T cells | 2.2 ± 0.5 | 1.1 ± 0.1 | 2.7 ± 0.3 | 4.7 ± 0.7 |
| NK cells [b] | 4.1 ± 0.3 | 32.6 ± 10.0 | 13.2 ± 1.6 | 16.4 ± 1.6 |
| Tregs [c] | 0.3 ± 0.1 | 0.9 ± 0.2 | 1.8 ± 0.1* | 0.9 ± 0.1 |
| TBLN MNC | | | | |
| Myeloid cells | 1.7 ± 0.8 | 18.2 ± 0.6 | 15.9 ± 3.6 | 18.6 ± 5.2 |
| Dendritic Cells | 1.5 ± 0.0 | 0.8 ± 0.1 | 0.1 ± 0 | 5.6 ± 1.2* |
| γδ T cells | 1.8 ± 0.1 | 1.1 ± 0.4 | 1.5 ± 0.3 | 8.6 ± 0.9* |
| NK cells | 5.1 ± 0.6 | 3.7 ± 0.3 | 1.3 ± 0.2 | 8.5 ± 3.7 |
| Tregs | 1.3 ± 0.7 | 3.1 ± 0.2 | 2.1 ± .02 | 1.8 ± 0.04 |

Figure 12:
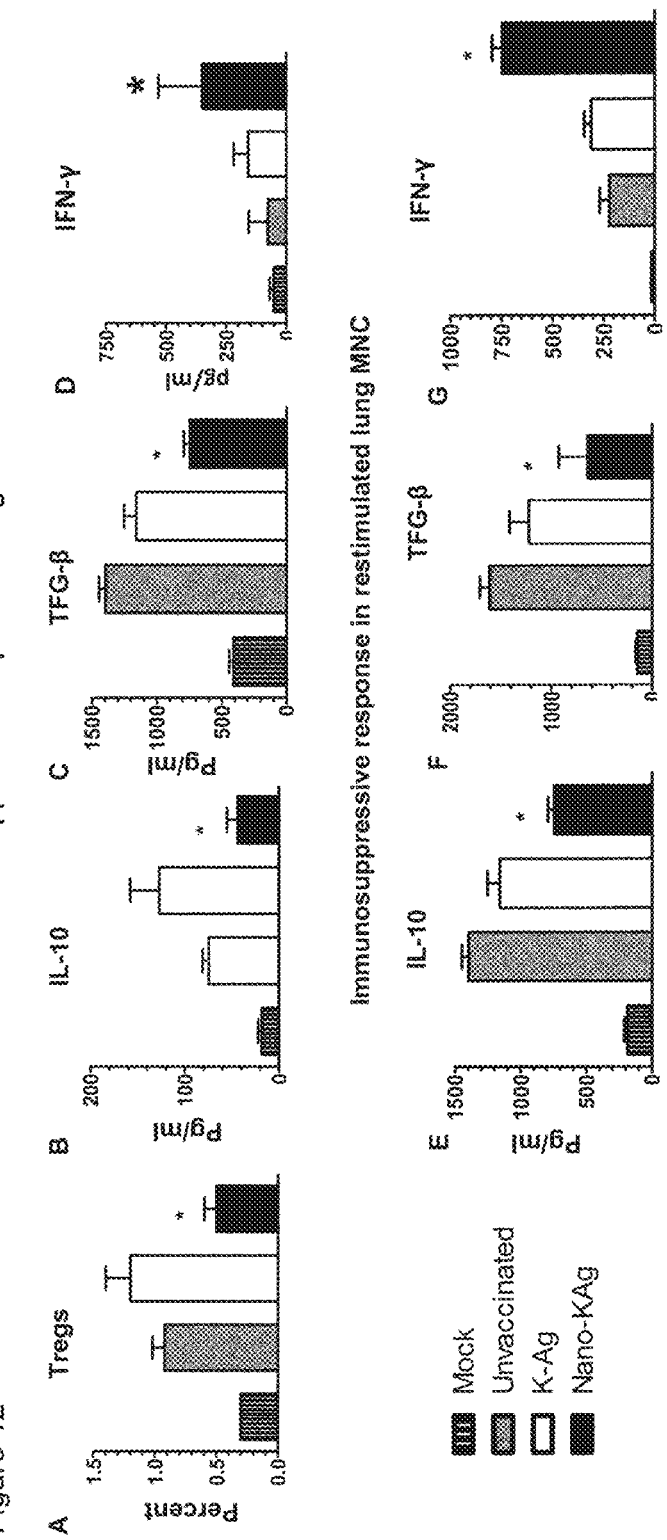
FIG. 12 shows a reduction in the immunosuppressive response in Nano-KAg vaccinated MN184 challenged pig lungs. Pigs were unvaccinated or vaccinated with either K-Ag or Nano-KAg once intranasally, challenged with PRRSV MN184 strain at PID 21 and euthanized at DPC 15. Lung MNC were analyzed for (A) Tregs population by flow cytometry. Lung homogenates were analyzed for (B) IL-10, (C) TGF-β, and (D)(IFN-α. Harvested culture supernatants from restimulated lung MNC were analyzed for cytokines (E) IL-10, (F) TGF-β, and (G) IFN-γ by ELISA. Each bar represents average values from three pigs±SEM. Asterisk represents the statistical significant difference (p<0.05) between Nano-KAg and K-Ag received pig groups. A similar trend in results was obtained in an independent second trial.

Suppression of Immunosuppressive Cytokine but Boosting of IFN-γ Response by Nano-KAg Pigs immunized with Nano-KAg vaccine showed significantly reduced Treg population in the lungs comparable to mock pigs (FIG. 12A). In contrast, unvaccinated and K-Ag immunized MN184 virus challenged pigs had higher levels of Treg cells compared to Nano-KAg group (FIG. 12A). Immunosuppressive cytokine response was strongly suppressed in Nano-KAg vaccinated pigs, indicated by significantly reduced levels of IL-10 and TGF-β in the lung homogenate; and also their increased secretion in a recall response of lung MNC was observed in Nano-KAg vaccinated compared to both unvaccinated and K-Ag immunized virus challenged pigs (FIGS. 12 B, C, E, & F). In contrast, a significantly increased IFN-γ in lung homogenate and its secretion in a recall response of lung MNC was detected in Nano-KAg vaccinated compared to control pigs (FIGS. 12 D&G).

Figure 13:
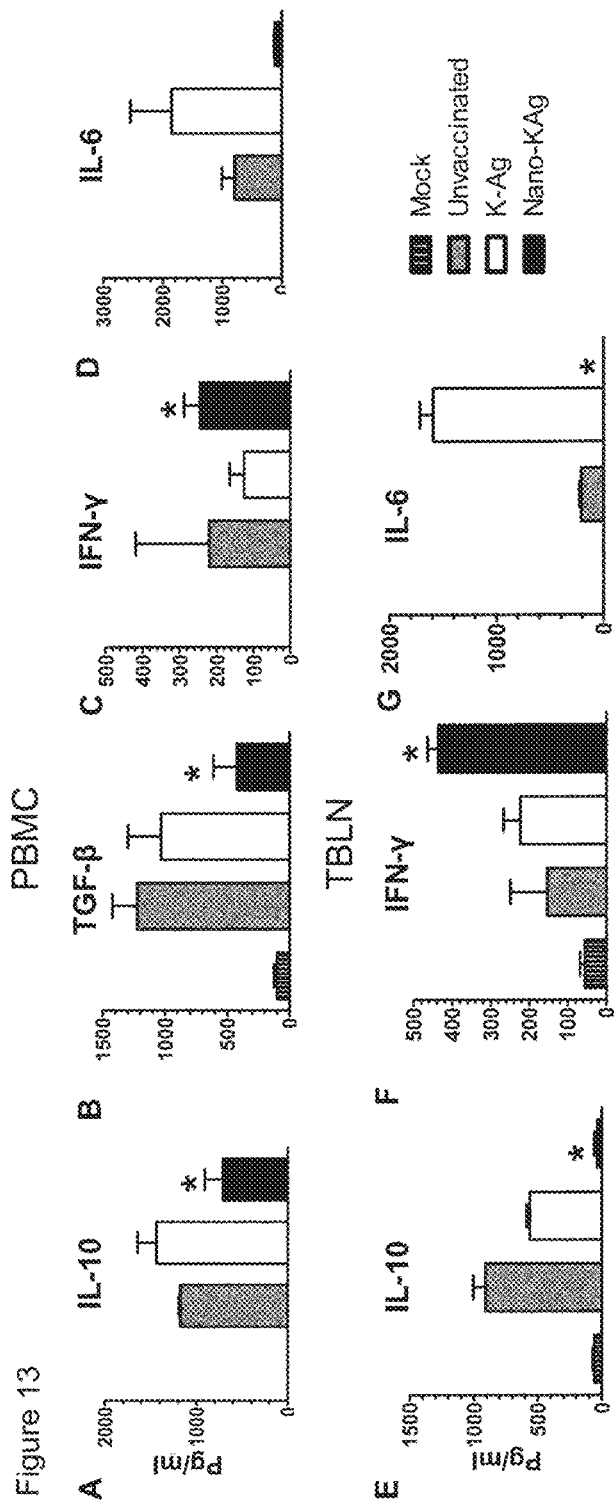
FIG. 13 shows an increased PRRSV specific recall cytokine response in PBMC and TBLN of Nano-KAg vaccinated MN184 strain challenged pigs. Pigs were unvaccinated or vaccinated with either K-Ag or Nano-KAg once intranasally, challenged with PRRSV MN184 strain at PID 21 and euthanized at DPC 15. Harvested culture supernatants from restimulated PBMC and TBLV MNC were analyzed for cytokines by ELISA: (A & E) IL-10, (B) TGF-β, (C & F) IFN-γ, and (D & G) IL-6. Each bar represents average values from three pigs±SEM. Asterisk represents the statistical significant difference (p<0.05) between Nano-KAg and K-Ag received pig groups. A similar trend in results was obtained in an independent second trial.
Figure 14:
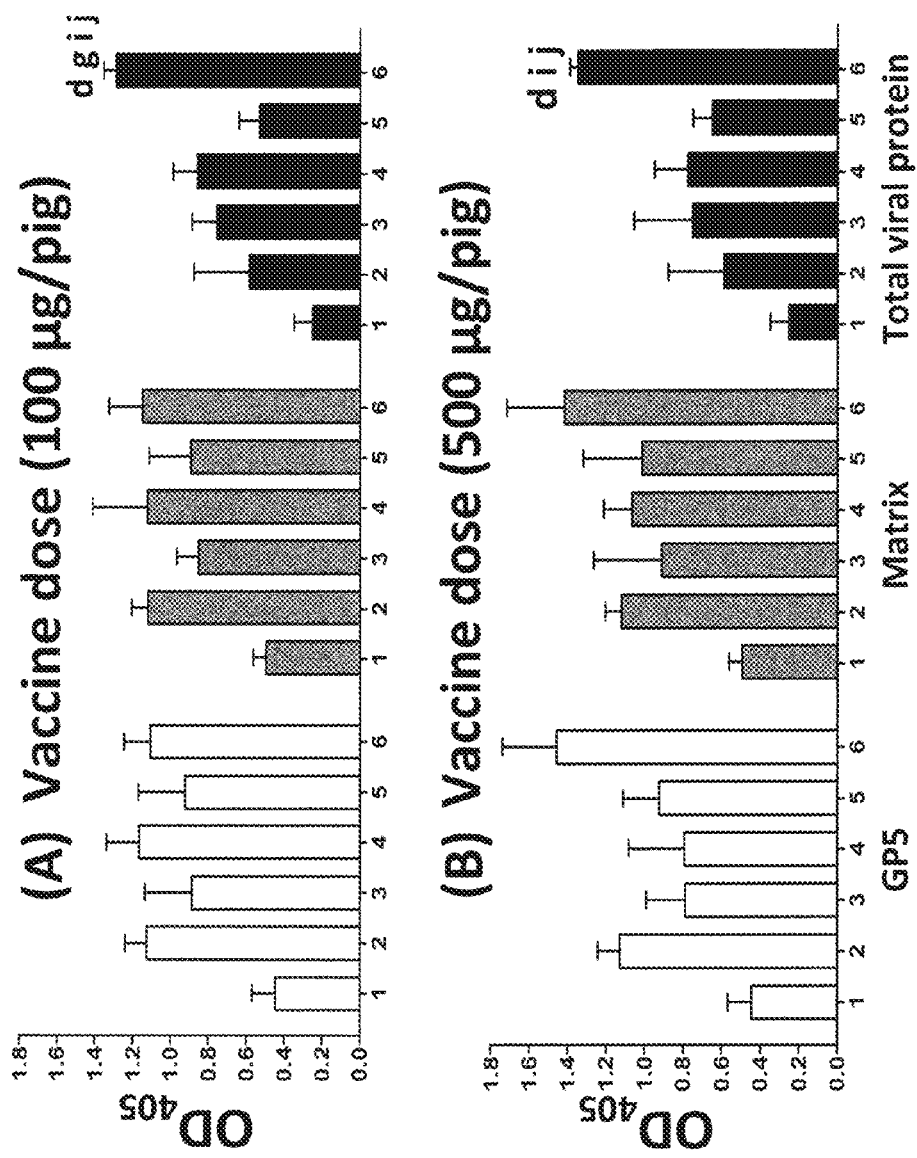
FIG. 14 shows an estimation of PRRSV specific IgA antibody production in bronchoalveolar lavage fluid of pigs against indicated PRRSV structural proteins and total viral protein by ELISA.
Figure 15:
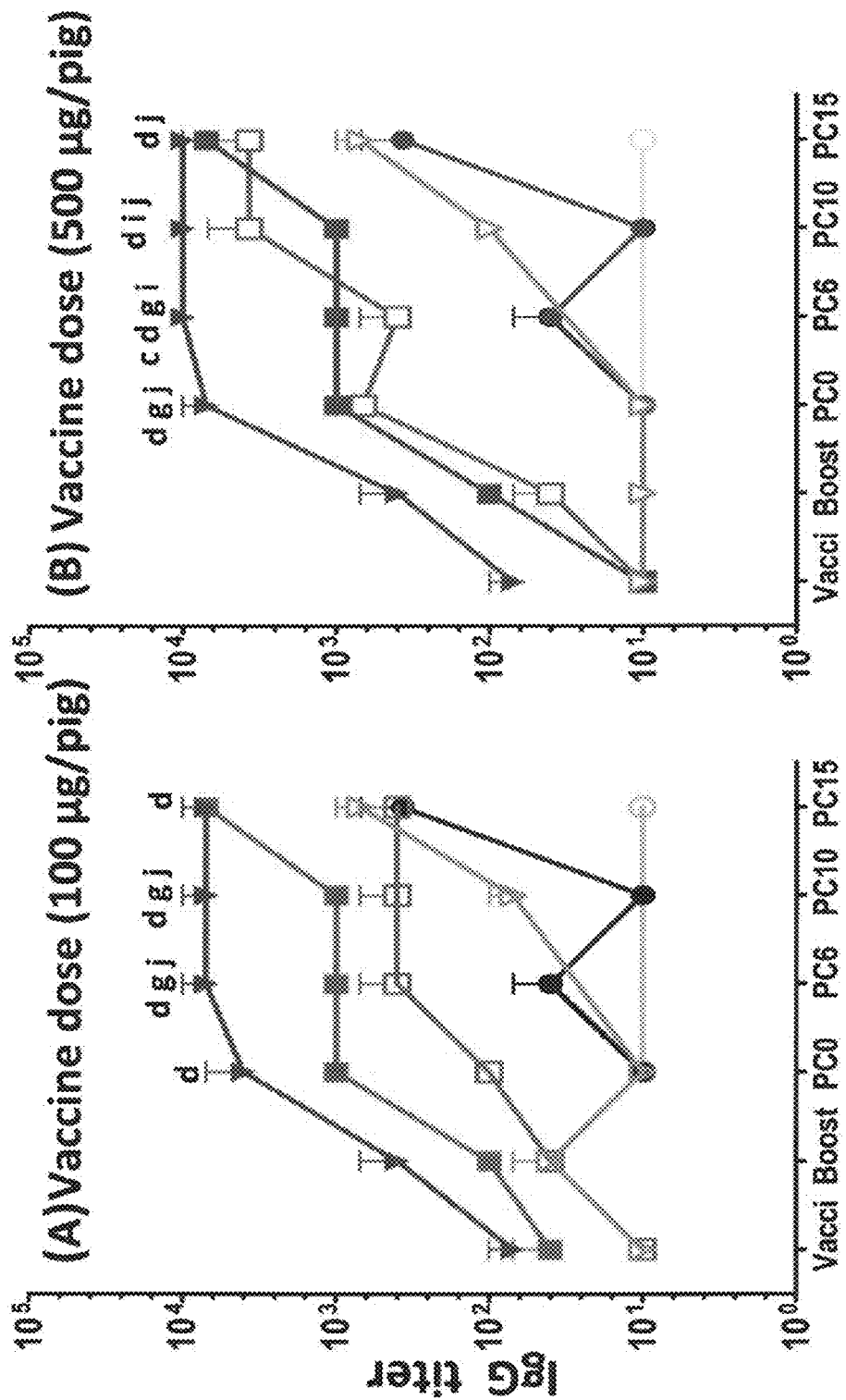
FIG. 15 shows an estimation of PRRSV specific total IgG antibody titer in the blood against total PRRSV protein by ELISA. PC—post-challenge day; Vacci.—1st vaccination; Boost—Booster dose.
Figure 16:
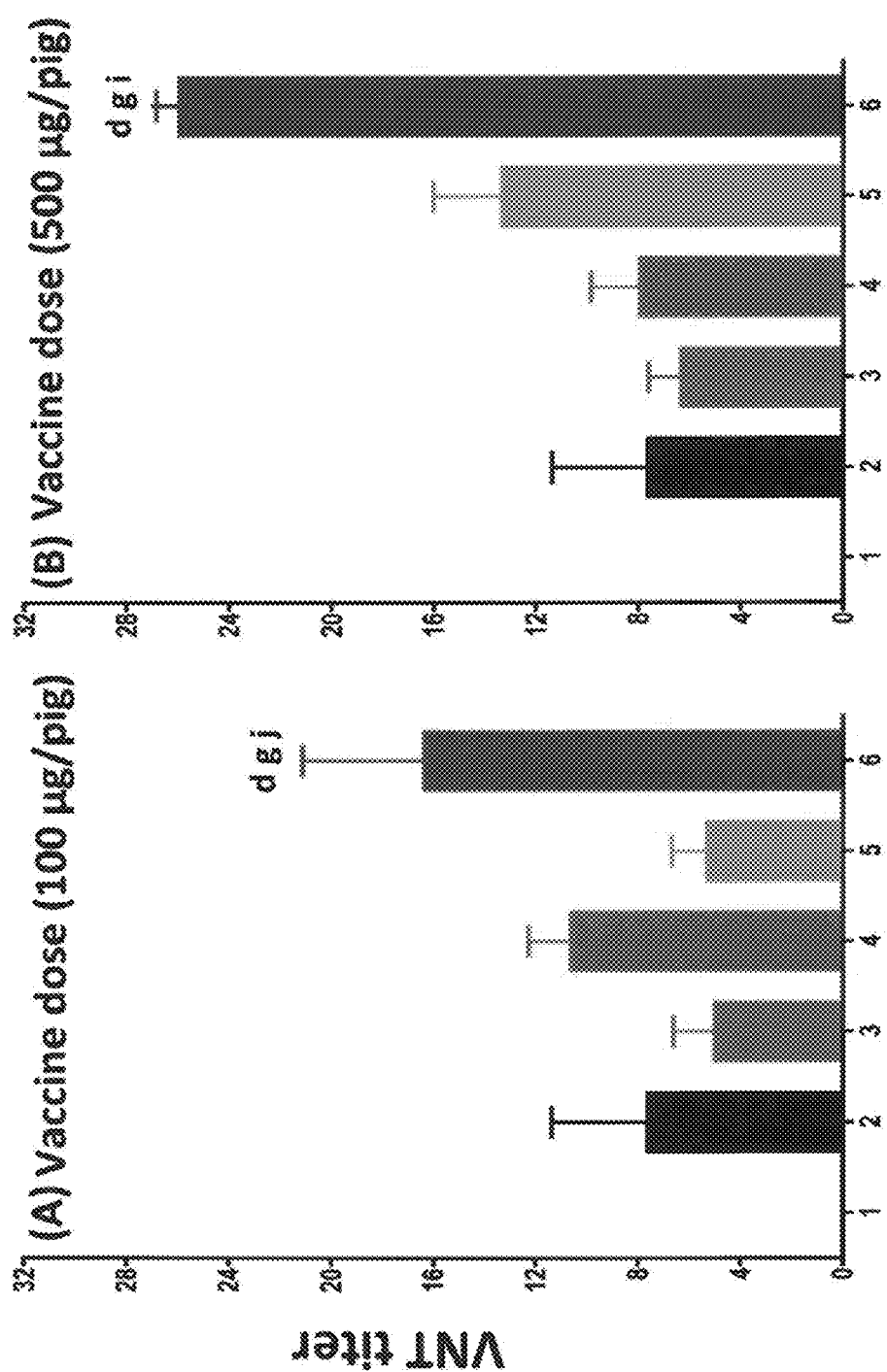
FIG. 16 shows an estimation of PRRSV specific neutralization titers (VNT) in the lungs of pigs by immunofluorescence assay.
Figure 18:
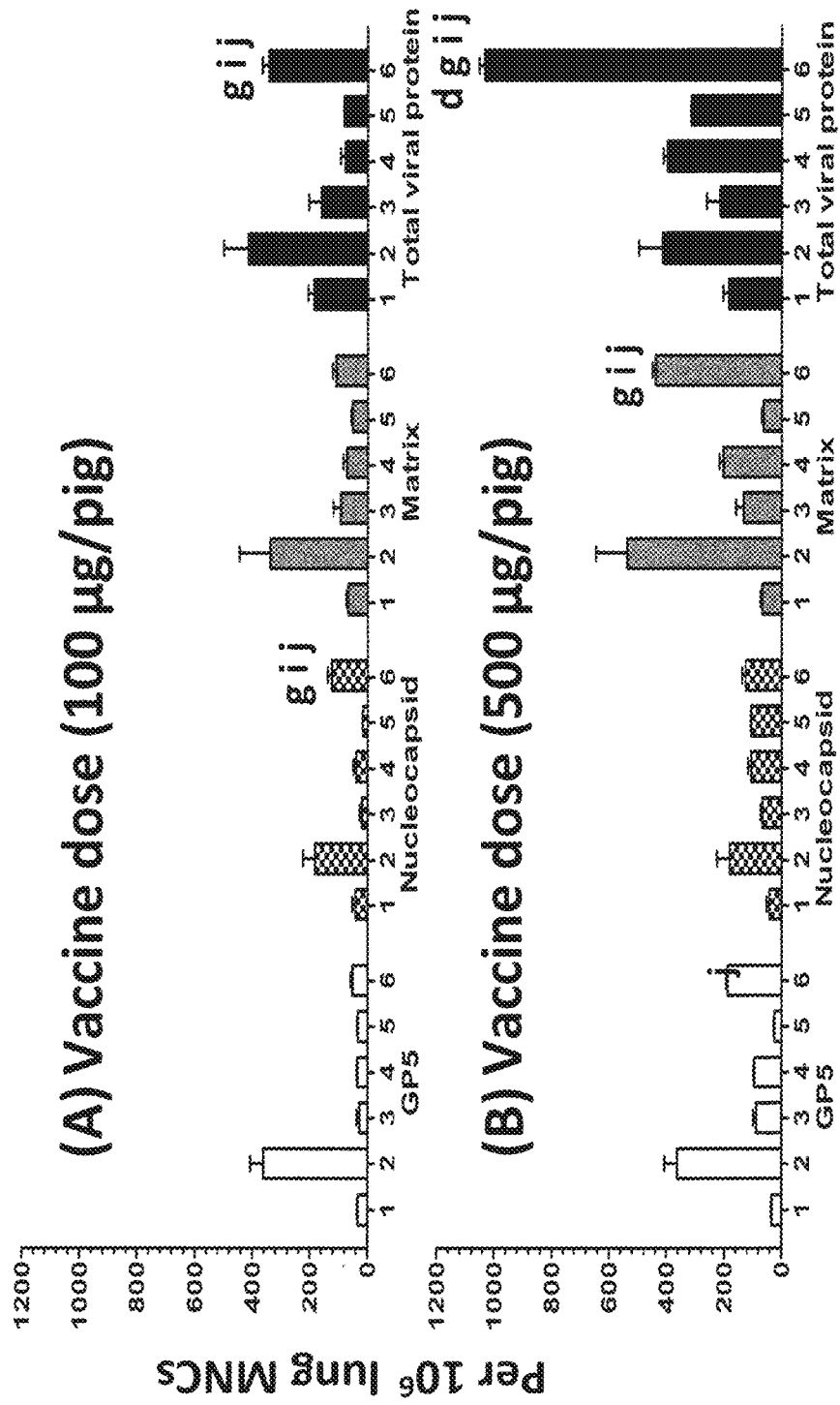
FIG. 18 shows an estimation of the frequency of IFN-γ secreting cells in the lungs of pigs specific to indicated PRRSV structural proteins and total viral protein determined by ELISPOT assay.
Figure 20:
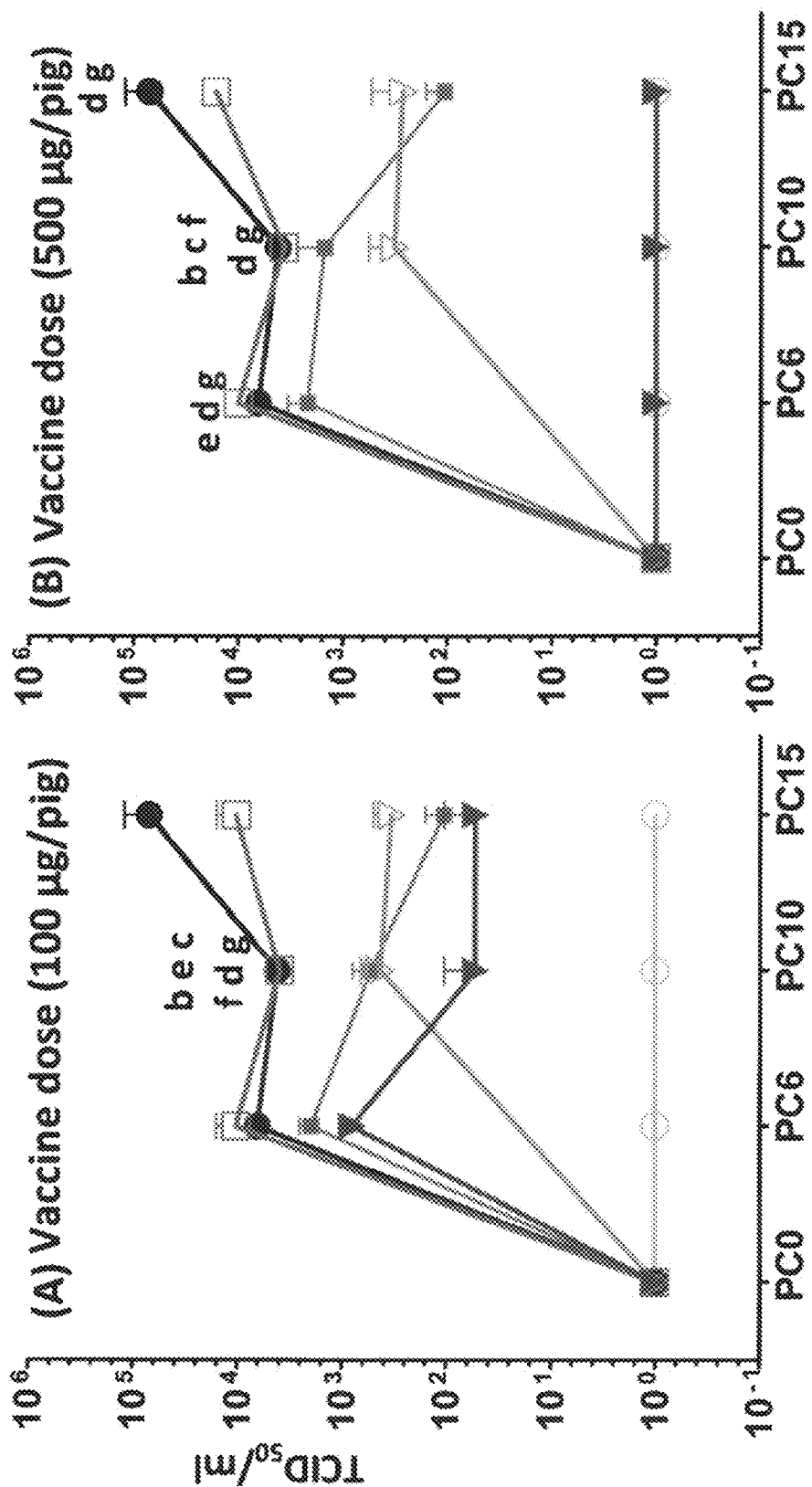
FIG. 20 shows a determination of infective PRRSV load in the blood samples of pigs determined by immunofluorescence assay.
Figure 22:
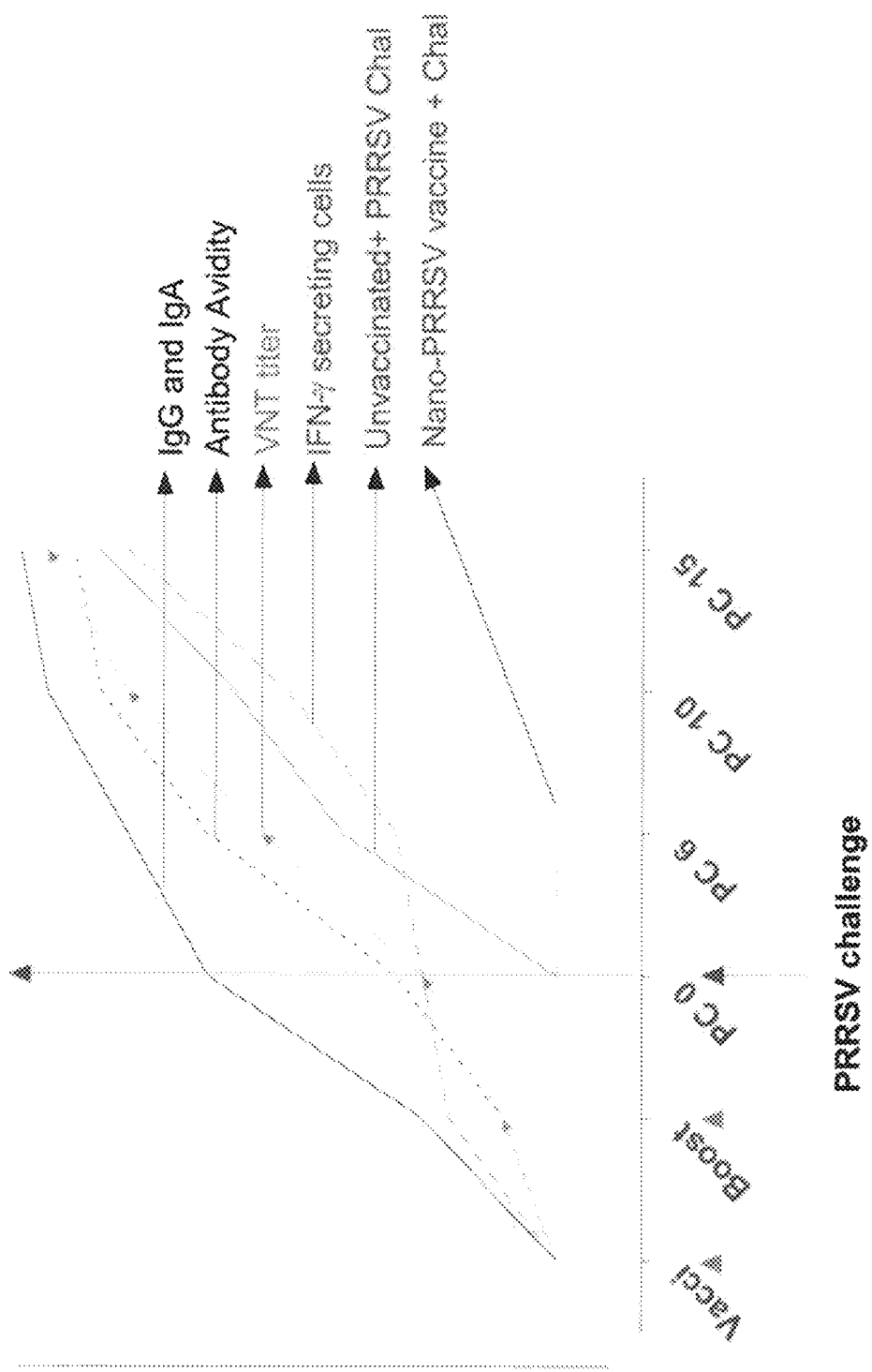
FIG. 22 shows a summary of immune responses and virus clearance in Nanoparticle entrapped PRRSV K-Ag+Mtb WCL vaccinated and heterologous PRRSV challenged pigs.

Cultured restimulated immune cells of Nano-KAg immunized pigs secreted significantly reduced IL-10 (both PBMC and TBLN-MNC) and TGF-β (PBMC), and an increased secretion of IFN-γ (both PBMC and TBLN-MNC) compared to unvaccinated and K-Ag immunized MN184 challenged pigs (FIGS. 13 A, B, C, E, & F). The level of proinflammatory cytokine, IL-6, in a recall response was significantly reduced in both PBMC and TBLN-MNC in Nano-KAg compared K-Ag immunized virus challenged pigs (FIGS. 13 D&G).

As disclosed herein, a rapid uptake of Nano-KAg vaccine by lung APCs followed by translocation of viral Ags into endosomal compartment, and increased expression of the activation marker CD80/86 on APCs were observed. These data show that virus specific adaptive immune response could be elicited in the respiratory tract of pigs using PLGA nanoparticle-based killed PRRSV vaccine. Differential cell counts from BAL fluid harvested from healthy mice, humans, and pigs have indicated that greater than 90% of cells are alveolar macrophages (62; 63; 64), showing that intranasally delivered Nano-KAg are phagocytosed by alveolar macrophages which serve as principle APCs in the lungs.

The pre-challenge study disclosed herein has demonstrated the capability of intranasally delivered candidate Nano-KAg vaccine to significantly increase the frequency of CD8+ T cells, Th/memory cells, with concomitant increase in the secretion of innate (IFN-β), proinflammatory (IL-6), and Th1 (IFN-γ) cytokines.

The post-challenge study using a virulent heterologous PRRSV has proved the ability of Nano-KAg vaccine to induce better cross-protective immunity in pigs. Immunologically, PRRSV modulates the innate immune function of pigs by dampening the IFN-α production, reduces the NK cell population and its cytotoxic function, which lead to weak/delayed adaptive immune response (28, 57). However, pigs vaccinated intranasally with Nano-KAg prevented a majority of virus induced immunosuppressive mechanisms with concomitant boost in innate and virus specific adaptive immune responses. γδ T cell is an important innate immune cell at mucosal sites and they possess non-MHC class I cytolytic activity. In Nano-KAg immunized pigs, increased population of γδ T cells, in addition to NK cells, CD4+ and CD8+ T cells, and increased secretion of IFN-γ were detected at both mucosal and systemic sites.

PRRSV infected pigs can be immunosuppressed due to increase in the population of Tregs and secretion of immunoregulatory cytokines, IL-10 and TGF-β (28, 75), and inhibition of IFN-γ production in pigs (77, 109, 78). Nano-KAg immunized pig lungs, TBLN and blood had significantly reduced Tregs associated with decreased IL-10 and TGF-β and increased IFN-γ secretion compared to unvaccinated and K-Ag vaccinated virus challenged pigs. In a pre-challenge study, increased secretion of proinflammatory cytokine IL-6 in Nano-KAg immunized pigs appears to be involved in initiation of adaptive immune response, and its diminished production in immunized post-challenged pigs was associated with reduced inflammatory lung pathology.

In Nano-KAg immunized pigs increased levels of PRRSV specific IgA, IgG, and VN antibody titers in the lungs, blood, and nasal wash were observed. Mucosal immunization can induce the production of IgA antibodies and effector response at distant tissues (21). The IgA antibody is protective against various viral infections and they possess significant virus neutralization activity at both mucosal surfaces and blood (50-53).

An important discovery to swine farmers and researchers is that the pigs immunized with Nano-KAg vaccine cleared the viremia of a virulent heterologous PRRSV in two weeks. Microscopic lung study in Nano-KAg immunized pigs was associated with the protective immune correlates and reduced viral load in the lungs.

Example 3

Nanoparticle-Based Adjuvanted Inactivated Porcine Reproductive and Respiratory Syndrome Virus Vaccine Elicits Superior Cross-Protective Immunity in Pigs Porcine reproductive and respiratory syndrome (PRRS) is responsible for greater than $664 million direct annual loss to the US pork industry (8). The causative agent, PRRS virus (PRRSV), is an enveloped positive strand RNA virus belongs to the family Arteriviridae. There are two known PRRSV genotypes, European (type I) and the North American (type II), with varying inter and intra genotypic genetic and antigenic diversity, signifying extreme mutagenic nature of PRRSV (38).

For about the last 20 years both modified live (PRRS-MLV) and inactivated PRRSV vaccines have been in use, but still control of PRRS remained unsuccessful. Moreover, PRRS-MLV has been implicated in the spread of mutated vaccine virus to susceptible pigs (32). Available inactivated vaccines are safe but poorly immunogenic (117). Therefore, development of a potent inactivated PRRSV vaccine is warranted. PRRSV primarily infects pigs through respiratory and genital mucosa, and its primary targets are macrophages (118). Intranasal delivery of a vaccine is non-invasive and has the ability to stimulate a protective immune response not only at the respiratory tract, but also in the genital tract and systemically (119). UV-irradiation or BEI inactivation of PRRSV preserves the functional immunogenic epitopes (100). Efficient Th1 response-inducing adjuvants are necessary in subunit/inactivated vaccines (120). Recently, the potent adjuvanticity of *M. tb* whole cell lysate (WCL) to PRRS-MLV was identified (28).

Biodegradable PLGA (poly lactide-co-glycolide) based micro/nanoparticles are widely used for targeted/sustained delivery of drugs and vaccines (121). PLGA is an FDA and European Medicines Agency (EMEA) approved agent (92). Intranasally delivered particulate antigens are sampled by M-cells of nasal lymphoid tissues, which in turn deliver to underlying professional antigen presenting cells (APCs) in the respiratory tract (122). Recently, it has been shown that a single dose of PLGA nanoparticle (NP) based inactivated PRRSV (NP-KAg) vaccine delivered intranasally to pigs elicits an immune response with substantial viral clearance (123). Coadministration of NP-KAg vaccine twice with nanoparticle entrapped/unentrapped *M. tb* WCL, intranasally, can elicit robust anti-PRRSV cross-protective immunity with complete viral clearance in pigs. These results demonstrate that NP-KAg vaccine coadministered with unentrapped *M. tb* WCL completely cleared the infective heterologous PRRSV both from the lungs and systemically.

Materials and Methods

Reagents

MARC 145 cells (14) were used to prepare PRRSV stocks and assays. Cells were maintained in DMEM with 10% FBS. For virus infection, DMEM with 2% horse serum was used. North American prototype PRRSV strain VR2332 (15) was used in vaccine preparation, and PRRSV MN184 (15). *Mycobacterium tuberculosis* whole cell lysate (*M. tb* WCL) was prepared as previously described (21).

Preparation of Vaccine Antigens and PLGA Nanoparticle-Based Vaccine Formulations PRRSV strain VR2332 (38) antigens was grown and UV-killed (KAg) as described previously to use in the vaccine (123). PLGA NPs entrapped with KAg (NP-KAg) or *M. tb* WCL (NP-*M. tb* WCL) were prepared by double emulsion method (w/o/w) as described (123, 41).

Determination of Protein Entrapment Efficiency and Characterization of NP-KAg

Entrapped protein in NPs was estimated as described (123). Morphology of the Nano-KAg was visualized using the Philips XL30-FEG scanning electron microscope (SEM) at 20 kV at 30,000× magnification. Size distribution of the sham or KAg entrapped NPs was measured using NICOMP 370 particle sizer (Particle Sizing Systems, CA). The zeta potential of the NPs was determined by ZetaPALS (Brookhaven Instruments Corp., NY).

Determination of In Vitro Protein Release from NP-KAg Vaccine

The assay was performed as previously described (124). Briefly, 50 mg NP-KAg was suspended in one ml PBS and the supernatant was collected immediately to estimate the burst release. The pellet of NP-KAg was resuspended repeatedly with one ml PBS and the supernatants were collected at 1, 5, 10, 15, 20, 25, and 30 days and stored at −20° C. On day 30, undegraded NPs were lysed to recover the protein, and all the samples were estimated for protein concentration by BCA method.

In Vitro Uptake of Nano-KAg by PAM Cells

Nano-KAg vaccine containing 2 μg of PRRSV KAg were suspended in one ml of RPMI and incubated with PAM cells (3D4/2, ATCC) for 0, 5, 20, 30 min, 3, 12, and 24 hr. KAg (2 μg), sham NPs, and cells infected for 24 hr with PRRSV VR2332 strain (MOI=1) were included as controls. Cells were washed and fixed with acetone and incubated with PRRSV N$^r$ mAb SDOW17 (Rural Technologies, Inc., SD) followed by anti-mouse IgG (H+L) Alexa-488 (Life Technologies, Grand Island, N.Y.), and observed under the inverted fluorescent microscope.

Pigs and Inoculations

Conventional Large White-Duroc crossbred, specific-pathogen-free weaned (3-4 weeks) piglets were procured from a swineherd seronegative for PRRSV, PRCV, TGV, and PCV2 antibodies. A total of 30 pigs were randomly divided into one of the 10 groups (3 pigs/group), and indicated vaccine formulation was inoculated (2 ml) twice at two-week interval (Table 2). Except pigs in group 1 all the other groups were challenged on post-vaccination day 28 with a virulent heterologous North American PRRSV (type II) strain MN184 ($5 \times 10^5$ TCID$_{50}$/pig) (38). Adjuvant and vaccine were entrapped separately and combined before administering them intranasally. The doses of the adjuvant and NP-KAg were tested earlier (123, 95). Pigs were euthanized on post-challenge day (PC) 15. Animals were maintained with food and water ad libitum, samples collected and euthanized as per the approved protocol of Institutional Animal Care and use Committee, The Ohio state University.

Table 2 shows a total of 30 pigs (N=30) were divided in ten groups each having three pigs (n=3). Groups 1 and 2 served as mock and mock vaccinated-challenged respectively. Other 8 groups were divided in to two dose categories of either 100 or 500 μg/pig of vaccine dose as detailed above. For statistical comparison, groups 1 and 2 were considered with both the categories.

TABLE 2

Pig groups used in the experiment.

| GP. No. | Experimental groups | |
| --- | --- | --- |
| 1 | Mock pigs (PBS and DMEM) | |
| 2 | Mock + Challenged with PRRSV- MN184 strain | |
| | Vaccine Dose (100 μg/pig) + Chal. | Vaccine Dose (500 μg/pig) + Chal. |
| 3 | 100 μg of K-Ag | 3. 500 μg of K-Ag |
| 4 | 100 μg of K-Ag + M. tb WCL | 4. 500 μg K-Ag/pig + M. tb WCL |
| 5 | 100 μg of NP-KAg + NP-M tb WCL | 5. 500 μg of NP-K-Ag + NP-M. tb WCL |
| 6 | 100 μg of NP- K-Ag + M. tb WCL | 6. 500 μg of NP-K-Ag + M. tb WCL |

Collection of Blood and Lung Samples for Analysis

Maximum PRRSV load in blood, lymphoid tissues, and lungs are detected at days 6 to 15 post121challenge/infection (125). Therefore, heparinized blood samples (3-5 ml) were collected on the day of vaccination and at PC 0, 6, 10, and 15, and plasma was aliquoted and preserved at −70° C. Pigs were monitored daily for the respiratory disease and rectal temperature, and the body weights were recorded twice weekly.

Preparation of Lung Homogenate and Isolation of MNCs from the Lungs and Blood

Lung homogenate was prepared as described (19). The lungs were lavaged with cold PBS containing antibiotics and bronchoalveolar lavage (BAL) fluid was recovered, clarified, aliquoted, and stored at −70° C. Blood was collected in ACD solution and peripheral blood mononuclear cells (PBMC) isolated (20), and from lung tissue samples lung MNCs (LMNC) were isolated (52).

Analysis of PRRSV Specific Antibodies

The assay was performed as described previously (53). Briefly, ELISA plates were coated with pre-titrated MN184 Ags or with PRRSV recombinant N, M, or GP5 proteins in carbonate buffer. For plasma mean OD value of 10-fold dilution of 30 PRRSV negative samples plus 2 times standard deviation (SD) was considered as the positive-negative cut-off. Reciprocal of the highest dilution of the plasma sample which had the OD value above the cut-off OD was considered as the end titer. PRRSV specific IgG1 and IgG2 antibodies in the lungs and plasma samples were analyzed as described (54).

PRRSV Specific IFN-γ Secreting Cells (ISCs) and Estimation of Cytokines

ELISPOT assay was performed to analyze ISCs as described (55). In the recall cytokine response, the supernatant harvested from PBMC cultures restimulated with killed MN184 Ags was analyzed for IL-4, IL-6 and IL-10 by ELISA as described (56). Lung homogenates were analyzed for IFN-γ, IL-12, IL-6, IL-10, and TGF-β by ELISA (21).

Avidity of the PRRSV Specific Antibodies in the Lungs and Blood

The assay was performed as described (57) with a few modifications. Briefly, to PRRSV Ags coated plate, test samples 1:100 diluted plasma, 1:10 lung homogenate, or undiluted BAL fluid was added and incubated; subsequently, serial two-fold diluted NH$_4$CN (5M to 0.313M) was added. The OD value of the test samples in NH$_4$CN untreated (0 M) wells was considered as 100%, and the test samples OD value in NH$_4$CN treated wells was calculated to reveal the percent retained Ag-Ab complex, expressed in percent.

Hematoxylin and Eosin Staining of Lung Tissue

The lung tissue samples collected from the right cranial lobe was fixed in 10% neutral buffered formalin and processed into paraffin blocks. Five micron sections were cut and stained for hematoxylin-and-eosin (H&E) as described previously (58).

Virus Titration and Virus Neutralization Assays

PRRSV titer and virus neutralizing antibody (VN) titer in lung homogenates and plasma samples were analyzed by the indirect immunofluorescence assay (37, 48). For VN assay, serially diluted samples were incubated with one of the PRRSV s 128 trains, MN184 (250 TCID$_{50}$), PRRSV 1-4-4 (accession #10-16734) (126) (100 TCID$_{50}$), or SD03-15 (21) (200 TCID$_{50}$). The PRRS viral titers in each gram of lung tissue or per ml of plasma, and virus specific VN titers were determined.

Determination of PRRSV RNA

Viral RNA copy number was detected in the lung homogenate (per gm of lung tissue) and BAL fluid (per ml) by quantitative real-time PCR as described (128).

Statistical Analysis

The data were expressed as the mean±SEM of three pigs. Statistical analyses were performed by one way ANOVA followed by Tukey's t-test using GraphPad Instat3 software.

Comparisons were performed between different treatment groups as mentioned below, and p<0.05 was considered for statistical significance (alphabets a to j).

a→Group 2 vs Group 3, b→Group 2 vs Group 4, c→Group 2 vs Group 5
d→Group 2 vs Group 6, e→Group 3 vs Group 4, f→Group 3 vs Group 5
g→Group 3 vs Group 6, h→Group 4 vs Group 5, i→Group 4 vs Group 6, and
j→Group 5 vs Group 6

Results

Figures 24A, 24B, 24C:
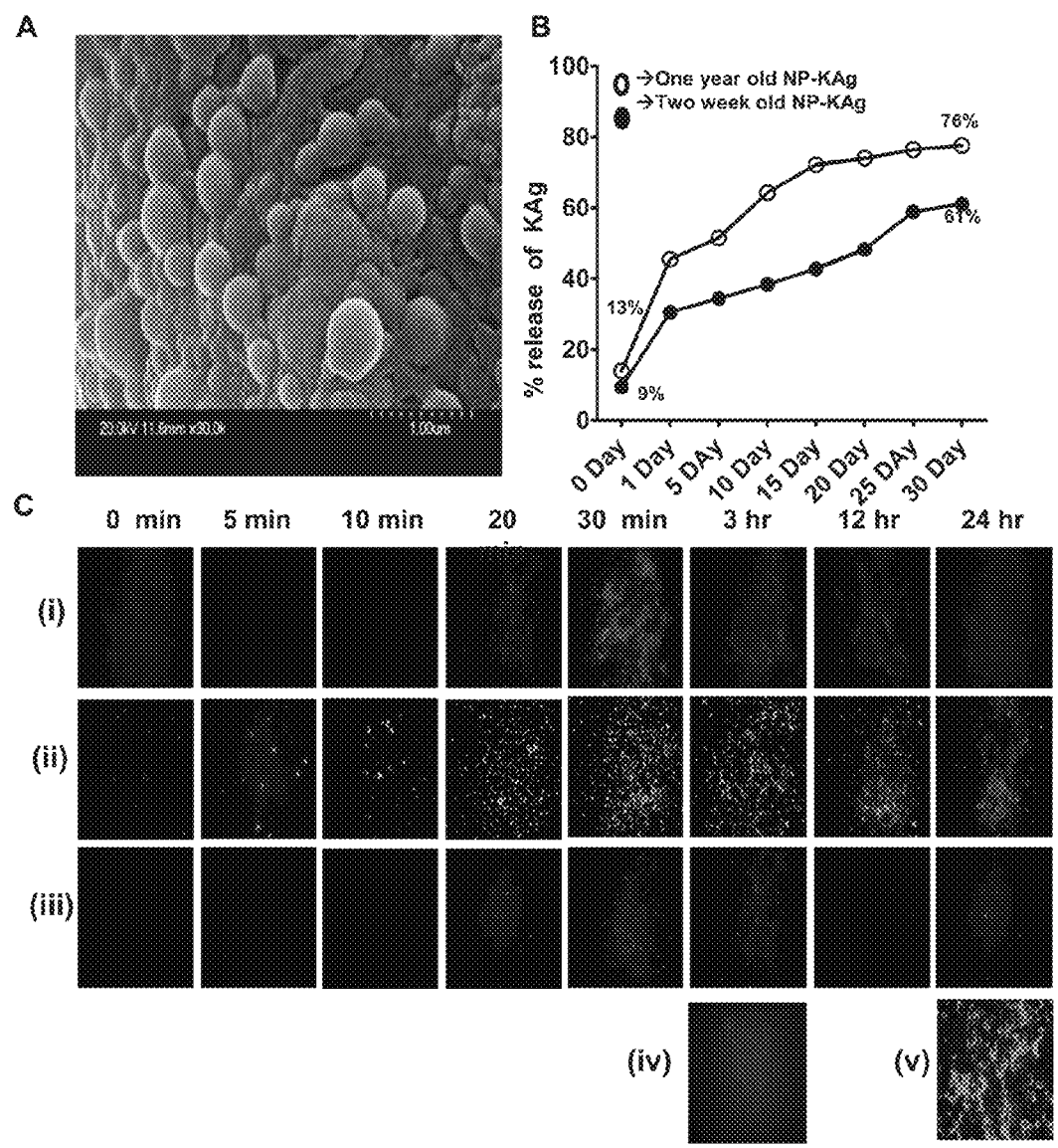
FIGS. 24A, 24B and 24C show the characterization of PRRSV KAg entrapped PLGA nanoparticles (NP-KAg). (A) The pictures were taken by Philips XL30-FEG SEM at 20 kV with 30,000× magnification. (B) PRRSV Ags release profile from NP-KAg was performed under normal physiological conditions. (C) Uptake of NP-KAg by pig PAM cells at indicated time point post-treatment. Each immunofluorescence picture is a representative of each treatment condition: (i) KAg; (ii) NP-KAg; (iii) Sham NPs; (iv) cells control; (v) PRRSV (VR2332) infected. Similar results were obtained in other two independent experiments.

NP-KAg Vaccine was Rapidly Endocytosed by Porcine Alveolar Macrophages (PAMs) and Sustained Release of Entrapped Ags Over Several Weeks Potency of NP mediated delivery of drugs or vaccines depends on their loading capacity and size (129). The entrapment efficiency of killed-PRRSV (KAg) and $M.\ tb$ WCL in NPs was about 50-60%. Sham or entrapped NP particles were circular with smooth surface (FIG. 24A). Dynamic light scattering (DLS) of NPs measured their diameter based distribution, and the mean diameter±SD of sham, NP-KAg, and 151 NP-$M.\ tb$ WCL were 480±53, 520±41, and 650±98 nm, respectively. Further, 85% of sham NPs, 92% of NP—$M.\ tb$ WCL, and 78% of NP-KAg were in the size range of 400-700 nm. Interestingly, there was no difference among all three NPs with respect to surface electrostatic potential (-26 mV) as measured by Zeta potential, indicating that differential surface charge of entrapped proteins did not influence the net electrostatic potential of finally formed NPs.

In Vitro Protein Release Profile of Nanoparticle Entrapped Inactivated PRRSV (NP-KAg)

The surface associated protein in nanoparticles is equivalent to the amount of protein released at time zero (i.e., immediately after reconstitution in PBS), called as burst release (130); and it was 9.5% in NP-KAg vaccine. The release during first 24 hr after reconstitution was 30.5% (FIG. 24B), and after 30 days 61% of the entrapped protein was released (FIG. 24B). The remaining 39% of viral Ags was recovered in the un-lysed NPs. Even one year old NP-KAg stored at -20° C. had 13.6% burst release, and 76% of released antigens by 30 days, indicating that PLGA NPs retain the entrapped vaccine beyond one year and allow its sustained release over a period of several weeks under normal physiological conditions (FIG. 24B). Thus, the results indicated that as expected PLGA nanoparticles could efficiently retain and permit sustained release of entrapped PRRSV Ags over a long period of time.

In Vitro Uptake of NP-KAg Vaccine by PAM Cells

PRRSV is host-specific, infects only pigs and the virus infects pulmonary alveolar macrophages (PAM). Treatment of PAM cells with the vaccine preparations revealed very little uptake of unentrapped KAg over 24 hr (FIG. 24Ci). In contrast, a rapid uptake of NP-KAg as early as 5 min and reached the peak by 30 min, followed by a gradual reduction in the fluorescence signals after 3 hr post-treatment (FIG. 24Cii); possibly due to degradation of Ags. Control sham nanoparticles treated and untreated PAM cells did not show any fluorescence signals (FIG. 24Ciii & Civ), while the PRRSV infected cells had virus specific green signals (FIG. 24Cv).

Figures 25A, 25B, 25C, 25D, 25E, 25F:
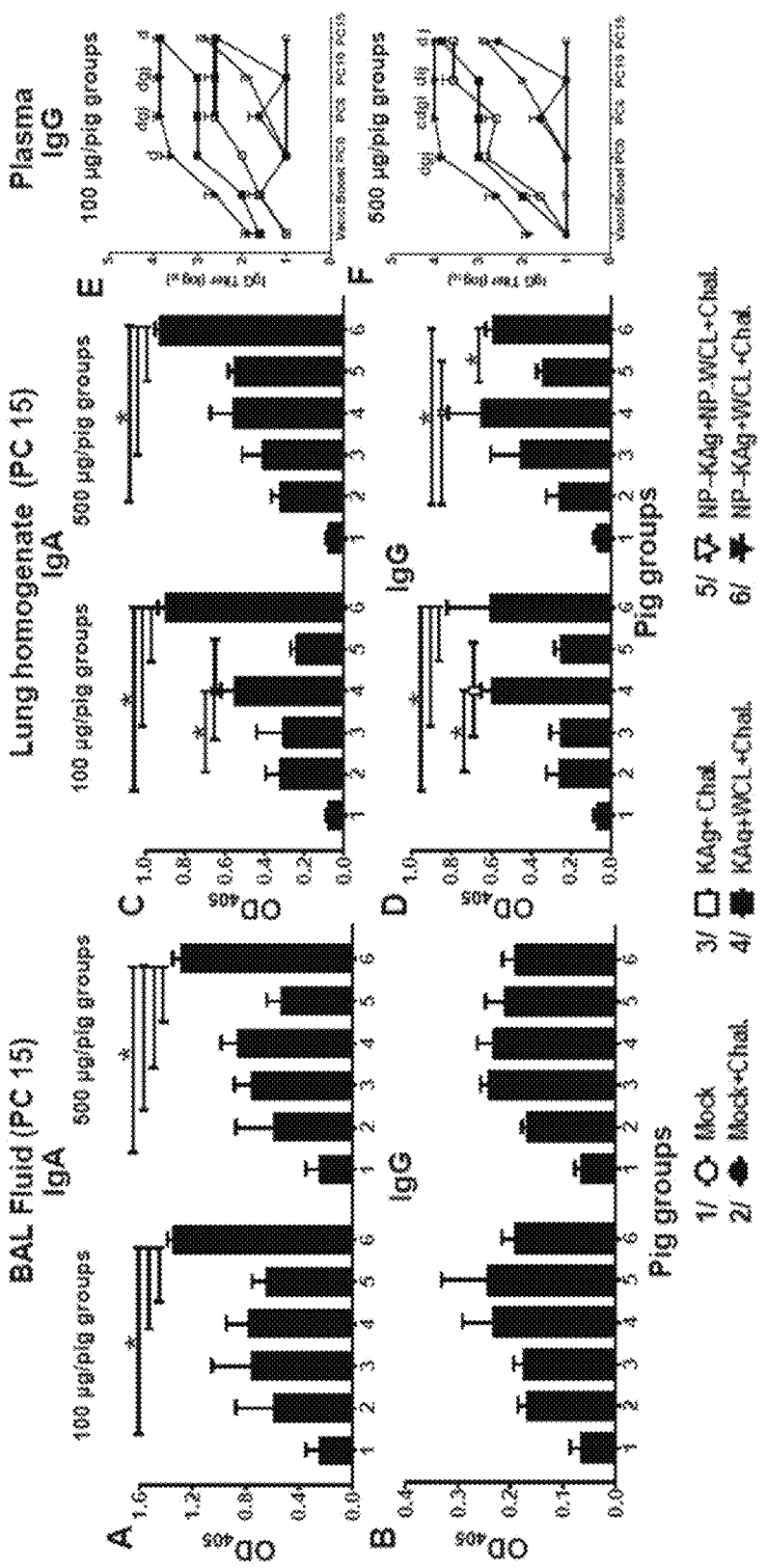
FIGS. 25A-25F show the significant increase in PRRSV specific antibodies in pigs vaccinated with adjuvanted NP-KAg. Pigs were vaccinated or unvaccinated with indicated vaccine and adjuvant combination and challenged with PRRSV MN184. The lung and blood samples collected at indicated PCs were analyzed for virus specific IgA (A & C) and IgG (B, D, E & F) by ELISA: (A&B) BAL fluid; (C, D) lung homogenate; (E, F) plasma samples. Each bar and each symbol in the line graph indicate the average value of three pigs±SEM. Asterisk and lowercase alphabets indicate statistically significant difference between indicated groups as described in methods. A similar trend in result was obtained in another independent experiment.
Figures 30A, 30B, 30C, 30D, 30E, 30F:
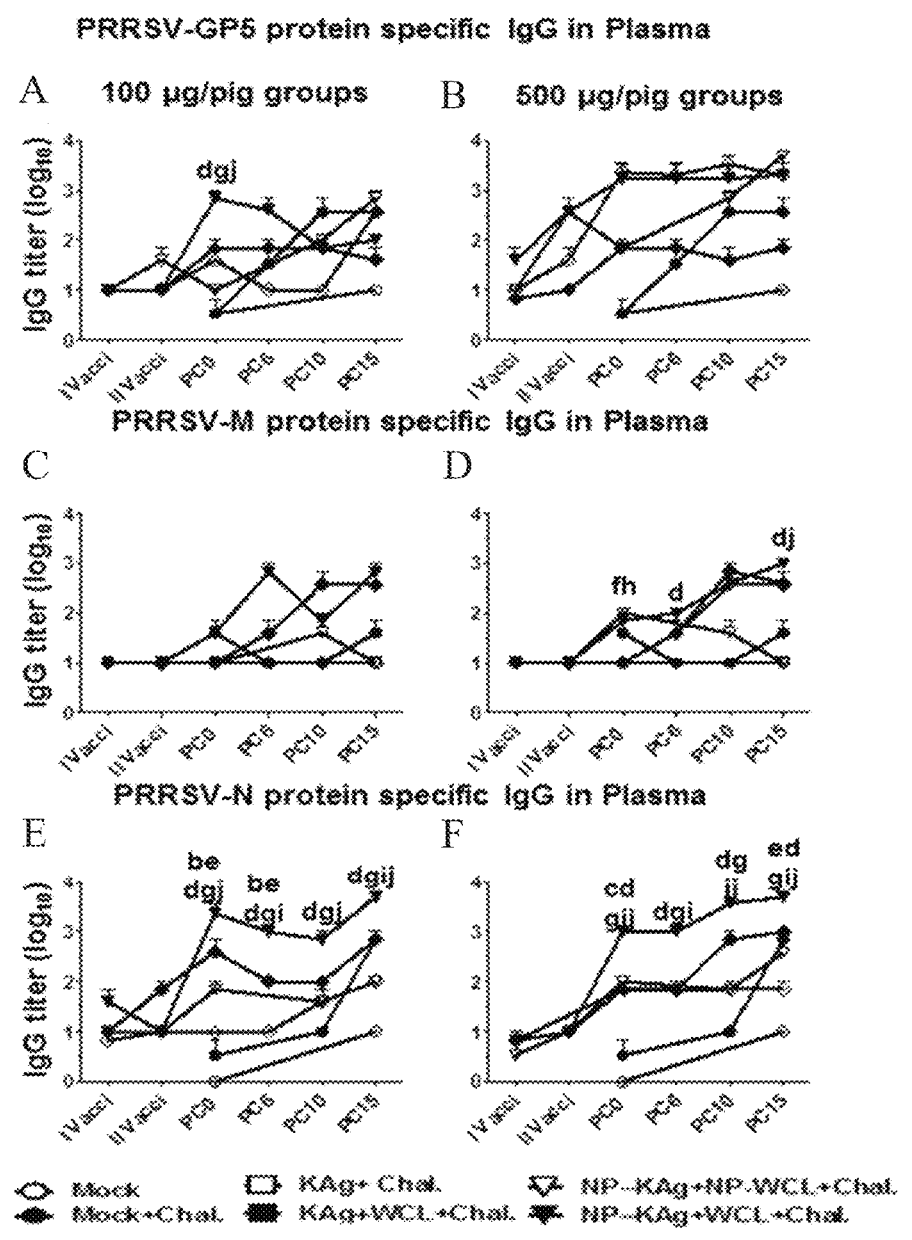

Enhanced Production of PRRSV Specific IgA in the Airway Surface and Both IgA and IgG in the Lung Parenchyma in Adjuvanted NP-KAg Immunized Pigs PRRSV specific IgA response was significantly higher in the BAL fluid and lung homogenate in group 6 pigs at PC 15 (both with 100 and 500 µg vaccine doses) compared to other test groups (FIGS. 25A & C). In contrast, comparable levels of virus specific IgG were detected in the BAL fluid of all the vaccine trial groups (FIG. 25B). In the lung homogenate a significantly higher levels of virus specific IgG were observed in pig groups 4 and 6 (FIG. 25D). The results indicated that in adjuvanted NP-KAg vaccinated pigs, virus specific IgA is a major antibody isotype in alveolar surfaces, while both IgA and IgG in the lung parenchyma. In the plasma of group 6 pigs (both vaccine doses), IgG response was significantly higher compared to group 2 pigs from PC 0 to 15 (FIGS. 25E & F). Overall, significantly increased levels of PRRSV specific antibodies were produced in NP-KAg+$M.\ tb$ WCL vaccinated pigs. Furthermore, PRRSV specific IgG response against recombinant structural proteins was evaluated and comparable levels of IgG titers against viral surface glycoprotein GP5 and M protein were found (FIGS. 30 A, B, C & D). While PRRSV nucleocapsid (N) protein specific IgG antibodies were significantly high in group 6 pigs (FIGS. 30E & F). These results indicated that NP-KAg+$M.\ tb$ WCL induced a strong humoral immune responses.

Figures 26A, 26B, 26C, 26D, 26E, 26F, 26G, 26H:
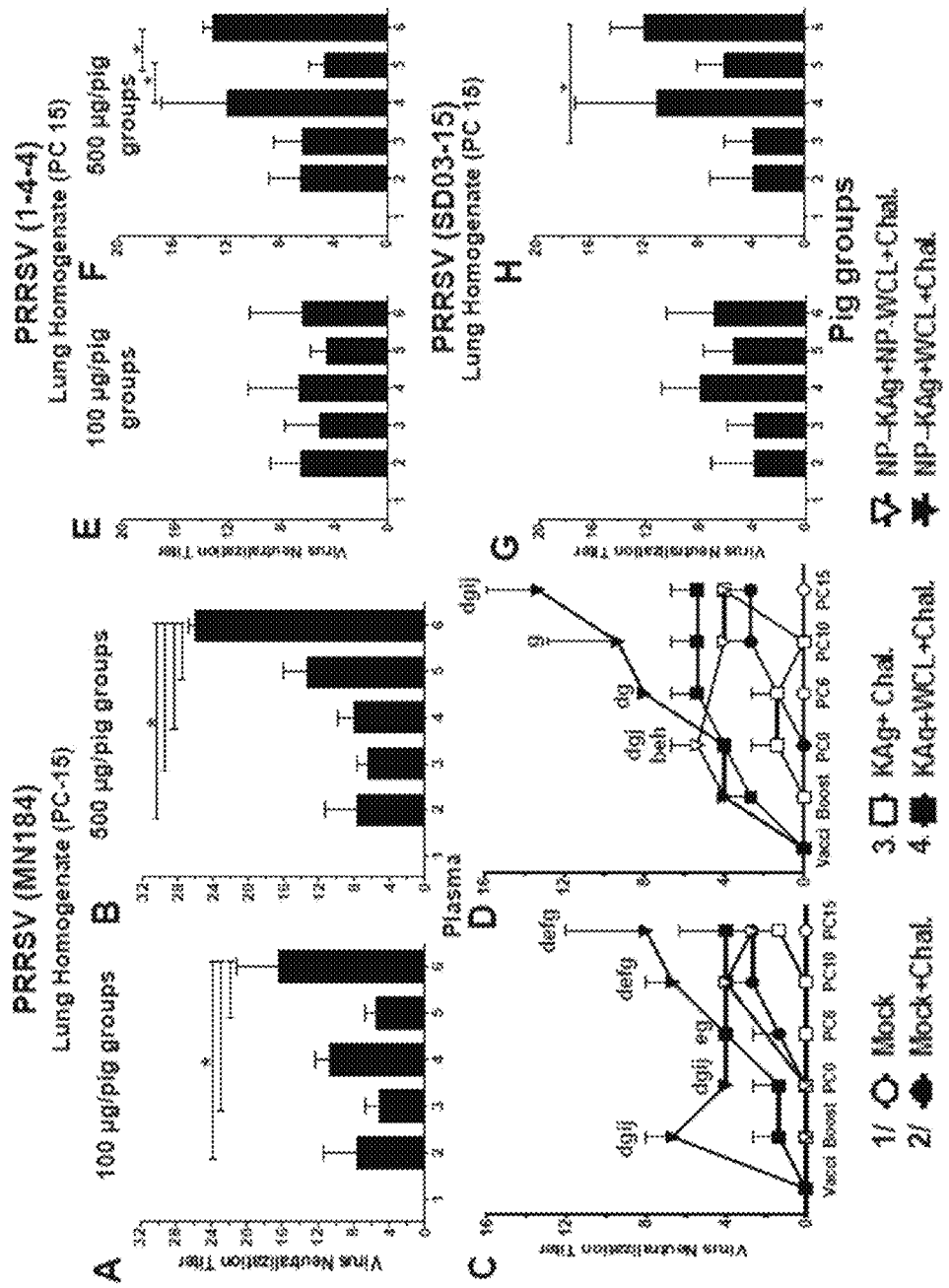
FIGS. 26A-26F show the enhanced heterologous and heterogenotype PRRSV neutralizing antibody (VN) titers in pigs vaccinated with adjuvanted NP-KAg. Pigs were vaccinated and challenged as described in figure legend 25. The lung homogenate (A, B, E-H) and plasma (C, D) samples collected at indicated PCs were analyzed for PRRSV VN titers: (A-D) VN titers against challenged PRRSV (MN184); (E, F) PRRSV (1-4-4); (G, H) PRRSV (SD03-15). Each bar and each symbol in the line graph indicate the average value of three pigs±SEM. Asterisk and lowercase alphabets indicate statistically significant difference between indicated groups as described in methods.

Broadly Cross Protective PRRSV Neutralization Response Elicited by Adjuvanted NP-KAg Neutralizing antibodies play an important role in the clearance of PRRSV infection (131). In group 6 pigs, the virus neutralization (VN) titers in the lungs against MN184 strain was significantly higher with mean titers 16 and 27 in pigs received 100 and 500 µg vaccine doses, respectively, compared to other groups (FIGS. 26 A & B). Plasma of group 6 pigs (at both the vaccine doses) had significantly higher VN titers compared to other groups (FIGS. 26C & D). Compared to 100 µg vaccine dose, the 500 µg dose elicited a steady increase in plasma VN titers in group 6 pigs (FIG. 26D). Against another antigenically divergent type II PRRSV strain 1-4-4 and a type I PRRSV strain SD03-15 (both these strains are genetically highly divergent from VR2332 and MN184 strains), significantly increased VN titers were detected in the lung homogenate of group 6 pigs (only with 500 µg dose) compared to group 5 and 3, respectively (FIGS. 26F & H). While the VN titers against PRRSV 1-4-4 and SD03-15 strains remained undetectable in the plasma until PC 10; and only in group 6 pigs (500 µg dose) a VN titer of eight against SD03-15 was detected at PC 15. These results indicated that adjuvanted NP-KAg elicits could elicit cross-reactive VN response.

Figures 27A, 27B, 27C, 27D, 27E, 27F, 27G, 27H, 27I:
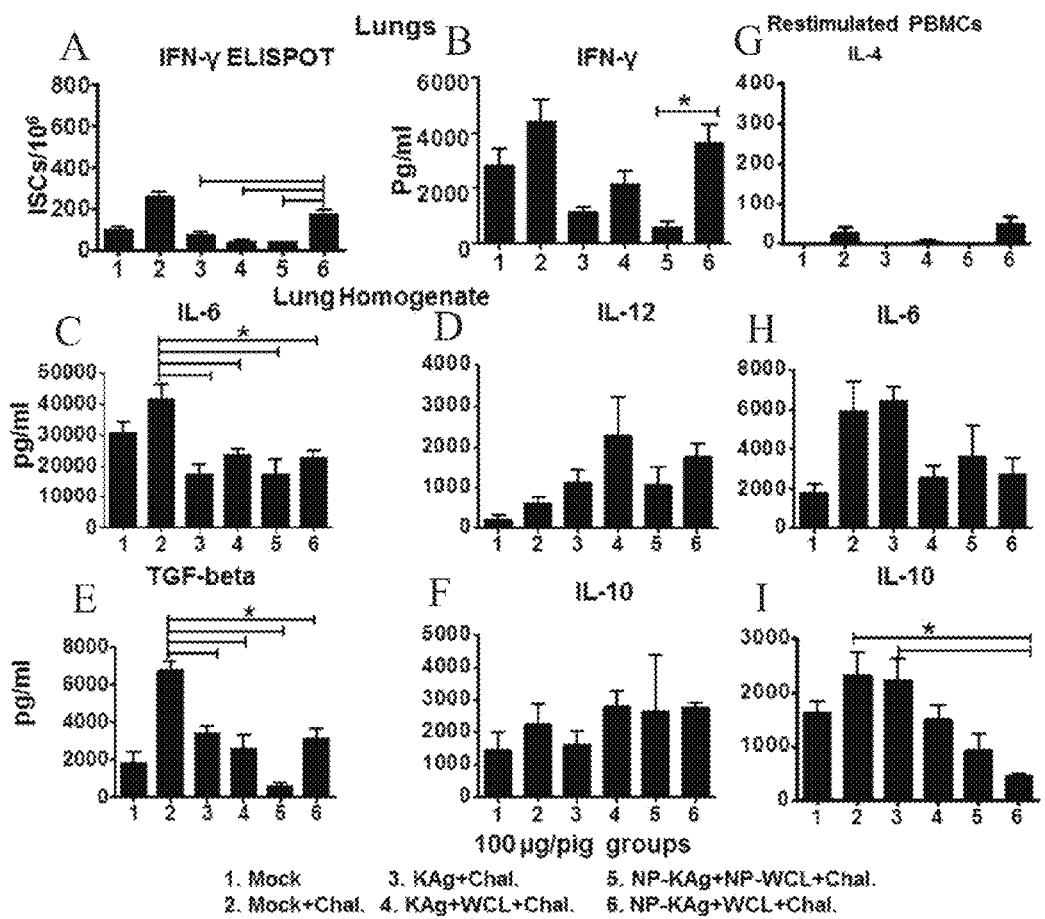
FIGS. 27A-27I show the enhanced production of Th1-Th2 and suppressed immunosuppressive cytokines in pigs vaccinated with adjuvanted NP-KAg vaccine (500 µg/pig category). Pigs were vaccinated and challenged as described in figure legend 25. (A) Lung MNCs were restimulated with killed MN184 Ags and the frequency of IFN-γ secreting cells (ISCs) was measured by ELISPOT. Lung homogenates were analyzed for: (B) IFN-γ; (D) IL-12; (C) IL-6; (E) TGF-β; (F) IL-10 by ELISA. PBMC were restimulated with killed MN184 Ags and the supernatant was analyzed for: (G) IL-4; (H) IL-6; (I) IL-10 by ELISA. Each bar indicates the average number of ISCs per million LMNC or average of cytokines from three pigs±SEM. Asterisk indicates statistically significant difference between the indicated pig groups. A similar trend in result was obtained in an independent second experiment.
Figures 32A, 32B:
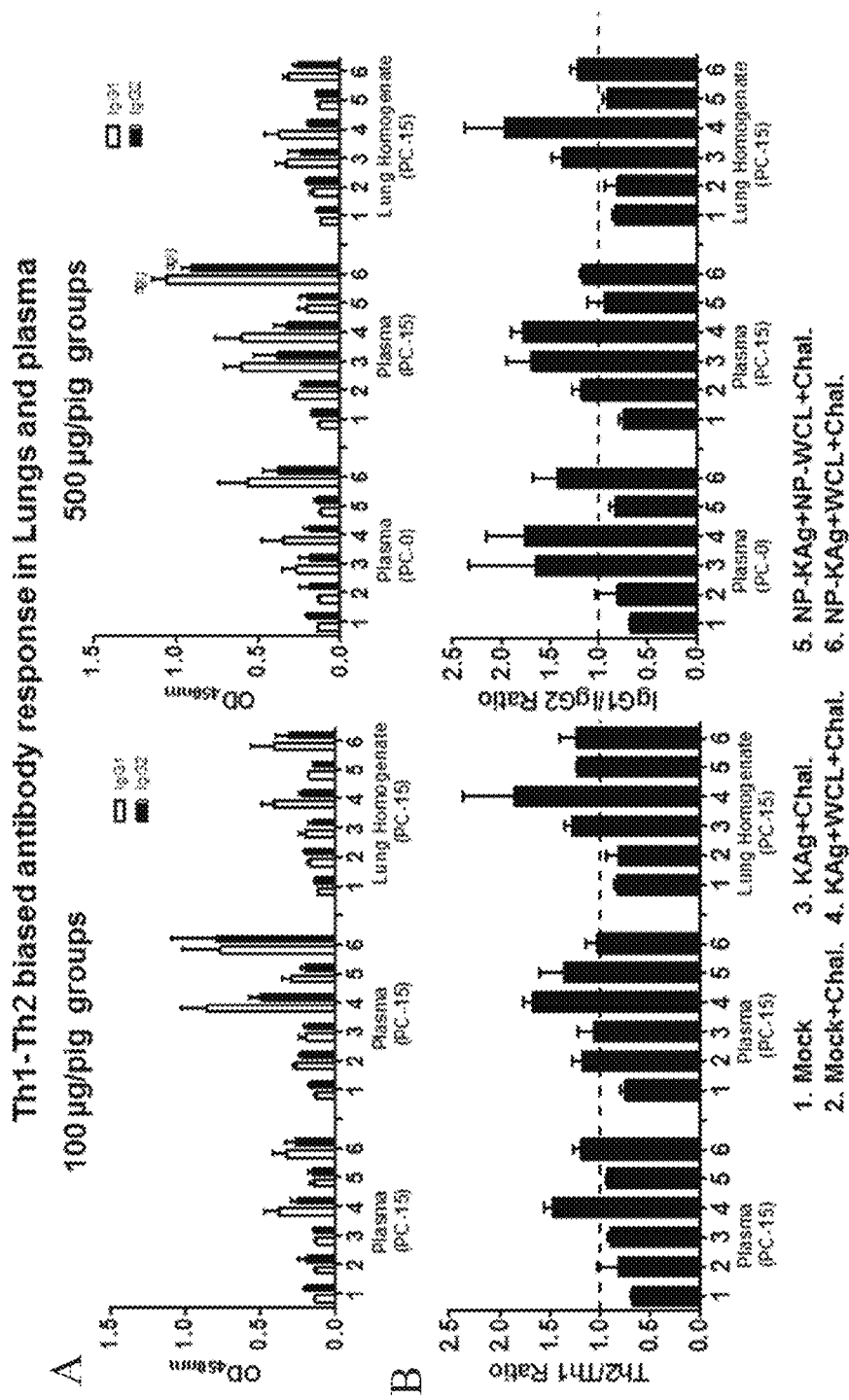
FIGS. 32A and 32B show increased levels of PRRSV specific IgG2 (Th1) and IgG1 (Th2) antibodies and Th1-Th2 balanced response in pigs vaccinated with adjuvanted NP-KAg vaccine. Pigs were vaccinated or unvaccinated with indicated vaccine and adjuvant combination and challenged with PRRSV MN184. The lung homogenate and plasma samples were analyzed for PRRSV specific IgG1 and IgG2 isotype specific antibodies by ELISA. (A) Each bar indicates the average OD value of three pigs±SEM. (B) Ratio of IgG1:IgG2 denotes Th1 or Th2 biased response. Each bar indicates the average ratio and the trend line indicates the cut-off ratio. Ratio of >1 and <1 indicates Th2 and Th1 biased response, respectively. Lowercase alphabet indicates statistically significant (p<0.05) difference between two indicated groups of pigs as described in materials and methods. A similar trend in result was obtained in an independent second experiment.
Figures 33A, 33B, 33C, 33D, 33E, 33F, 33G, 33H, 33I:
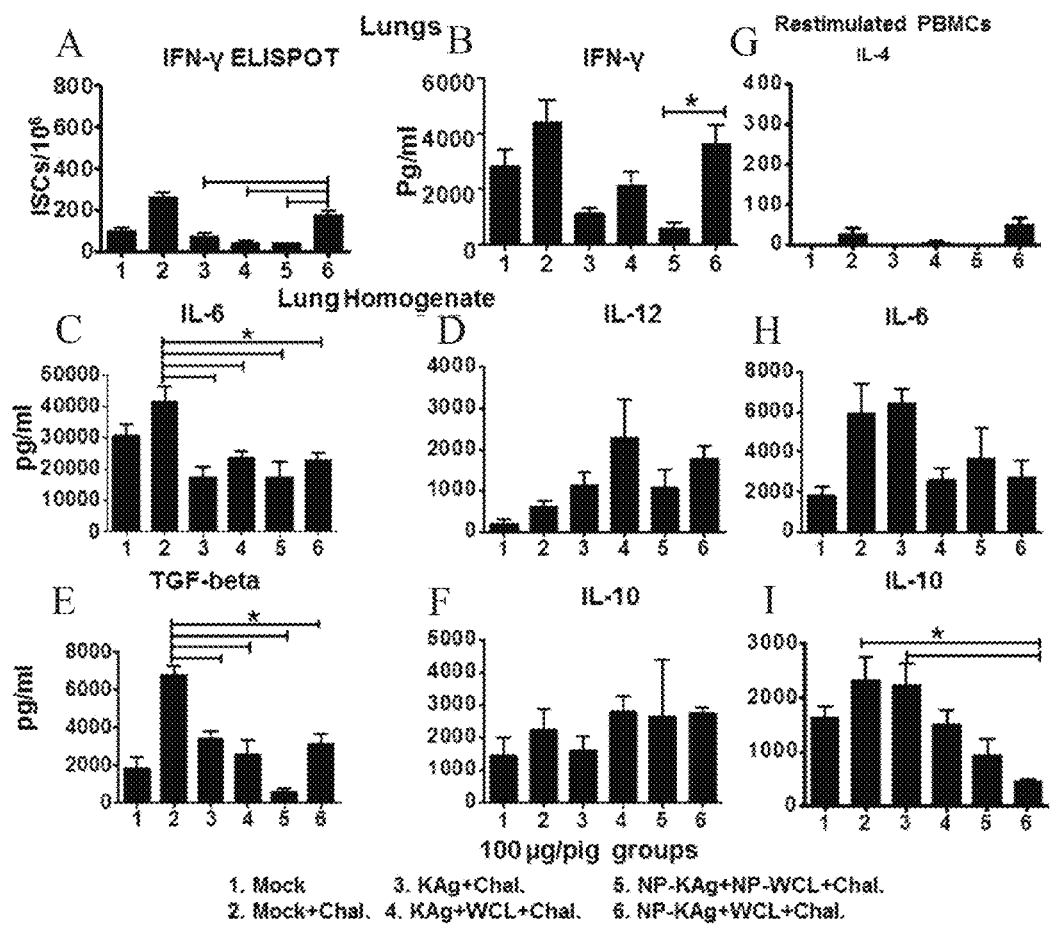

Downregulated Immunosuppressive and Enhanced (and Balanced) Th1-Th2 Cytokine Response in Adjuvanted NP-KAg Inoculated Pigs Group 6 pigs (both the vaccine doses) had significantly increased interferon-γ secreting cells (ISCs) in lung mononuclear cells (LMNC) compared to groups 3, 4, and 5 (FIGS. 27A & 33A). The IFN-γ production in the lung homogenate at PC 15 was significantly increased in group 6 pigs compared to groups 4 and 5 in 500 µg dose category (FIG. 27B), and compared to only group 5 in 100 µg dose category (FIG. 33B). Production of another important Th1 cytokine, IL-12, was significantly increased in groups 4 and 220 6 pigs (500 µg dose) (FIG. 27D). Production of a proinflammatory cytokine IL-6 in the lungs was significantly reduced in all the vaccine trial groups compared to group 2 (FIGS. 27C & 33C). The cytokines TGF-β and IL-10 are considered as immunoregulatory and immunosuppressive in nature. Production of TGF-β was significantly reduced in the lungs of group 6 pigs compared to group 2 (FIGS. 27E & 33E), and the levels of IL-10 were comparable in all the tested groups at PC 15 (FIGS. 27F & 33F). Secretion of IL-6 by restimulated PBMC of group 6 pigs was significantly reduced compared to group 2 (500 µg dose) (FIG. 27H). Interestingly, secretion of IL-10 by PBMC in a recall response was significantly reduced in group 6 pigs compared to groups 2 and 3 in both the vaccine dose category (FIGS. 27I and 33I). The cytokine IL-4 is an important indicator of a Th2 response, and significantly increased secretion of IL-4 by restimulated PBMC was observed in group 6 pigs compared to all other groups which received 500 µg dose of vaccine (FIG. 27G). These data clearly indicated that adjuvanted NP-KAg induced increased Th1 and Th2 and reduced immunosuppressive cytokines production, which was correlated with the production of balanced Th1-Th2 antibody sub-isotypes (FIGS. 32A & B).

Enhanced Frequency of IFN-γ Secreting Lymphocytes and APCs in Adjuvanted NP-KAg Immunized Pigs LMNC and PBMC were immunostained and analyzed for lymphoid and myeloid cells, and IFN-γ$^+$ cells. Groups 6 pigs showed significantly higher population of total IFN-γ producing cells both in LMNC and PBMC (FIGS. 28A & J and 34A & J). Pig groups 3, 4, and 6 (500 µg dose) had significantly increased activated CD4 cells (CD4$^+$CD8$^-$CD25$^+$241) in LMNC (Table 3, B), but significantly increased IFN-γ$^+$CD4$^+$ cells only in group 6 pigs in both LMNC and PBMC (FIGS. 28B & K). IFN-γ$^+$CD8$^+$ cells were significantly increased in group 6 pigs in both LMNC and PBMC (FIGS. 28C & L). In the lungs, IFN-γ$^+$CD4$^+$ CD8$^+$ cells were significantly higher in group 6 pigs than all other tested groups (FIG. 28D), and compared to groups 3 and 5 in PBMC (FIG. 28M). Increased frequency of activated γδ T cells in group 6 pigs was detected in group 6 pigs compared to other groups (Table 3, A & B). Both in LMNC and PBMC a significantly increased IFN-γ$^+$ γδ T cell population in group 6 pigs were detected (FIGS. 28E & N). Although there was no significant difference in NK (CD56+) cell frequency (FIGS. 28F & O), a significant increase in IFN-γ+ 250 NK cell frequency was detected in group 6 pigs compared to other tested groups (FIGS. 28G & P). With regards to myeloid cells in LMNC, significantly increased SLAII$^+$ macrophages (MΦs) (CD172$^+$CD163$^+$SLAII$^+$) in group 6 pigs compared to group 5 (FIG. 28H), but not in PBMC were detected (FIG. 28Q). In addition, dendritic cells (DCs) rich population (CD172+CD11c+SLAII+) was significantly higher in group 6 pigs compared to group 5 in LMNC (FIG. 28I), and compared to all other tested groups in PBMC (FIG. 28R). A similar trend (but not significant in some groups) in lymphoid and myeloid cell frequencies in 100 µg/pig dose received group 6 pigs was observed (FIG. 34 and Table 3, A).

Table 3 shows the frequency of indicated activated (CD25$^+$) lymphocyte subsets present on the day of euthanization in the LMNC (A) and PBMC (B) of pigs vaccinated or unvaccinated with indicated vaccine and adjuvant combination and challenged with PRRSV MN184. Each number is an average frequency of indicated immune cell from three pigs±SEM. Lower case alphabet indicates statistically significant (p<0.05) difference between two indicated groups of pigs as described in materials and methods.

TABLE 3

The populations of activated lymphocyte subsets.

| | Mock (1) | Mock + Ch (2) | KAg + Ch. (3) | KAg + WCL + Ch. (4) | NP (KAg + WCL) + Ch (5) | NP-KAg + WCL + Ch. (6) |
|---|---|---|---|---|---|---|
| (A) 100 µg/pig vaccine dose category | | | | | | |
| LMNC | | | | | | |
| CD4$^+$CD8$^-$CD25$^+$ | 7.2 ± 0.7 | 7.3 ± 1.2 | 19.9 ± 9.2 | 16.3 ± 1.2 | 3.3 ± 1.1 | 20.7 ± 2.2 |
| CD4$^-$CD8$^+$CD25$^+$ | 4.5 ± 0.4 | 4.2 ± 0.4 | 0.3 ± 0 | 0.5 ± 0.2 | 0.2 ± 0.1 | 2.1 ± 0.7$^{gij}$ |
| γδ$^+$CD25$^+$ | 0.1 ± 0 | 0.4 ± 0.3 | 0.5 ± 0.3 | 0.7 ± 0.3 | 0.2 ± 0 | 1.9 ± 0.3$^{dgij}$ |
| PBMC | | | | | | |
| CD4$^+$CD8$^-$CD25$^+$ | 5.0 ± 1.3 | 7.7 ± 1.7 | 10.7 ± 6.2 | 17.8 ± 3.0 | 4.41 ± 1.62 | 12.2 ± 1.0 |
| CD4$^-$CD8$^+$CD25$^+$ | 6.1 ± 2.8 | 6.9 ± 1.1 | 2.6 ± 1.4 | 3.3 ± 0.2 | 1.68 ± 1.19 | 5.2 ± 2.1 |
| γδ$^+$CD25$^+$ | 0.2 ± 0.1 | 0.3 ± 0.1 | 0.2 ± 0.1 | 1.0 ± 0.5 | 0.54 ± 0.16 | 0.8 ± 0.2 |
| (B) 500 µg/pig vaccine dose category | | | | | | |
| LMNC | | | | | | |
| CD4$^+$CD8$^-$CD25$^+$ | 7.2 ± 0.7 | 7.3 ± 1.2 | 17.0 ± 1.5$^{af}$ | 16.2 ± 1.1$^{bh}$ | 3.3 ± 1.2 | 10.8 ± 2.2$^j$ |
| CD4$^-$CD8$^+$CD25$^+$ | 4.5 ± 0.4 | 4.2 ± 0.4 | 1.2 ± 0.6 | 0.9 ± 0.4 | 0.1 ± 0 | 1.3 ± 0.3 |
| γδ$^+$CD25$^+$ | 0.1 ± 0 | 0.4 ± 0.3 | 1.4 ± 0.5 | 0.8 ± 0 | 0.3 ± 0 | 2.3 ± 0.2$^{dij}$ |
| PBMC | | | | | | |
| CD4$^+$CD8$^-$CD25$^+$ | 5.0 ± 1.3 | 7.7 ± 1.7 | 13.3 ± 6.2 | 19.3 ± 7.4 | 5.7 ± 0.7 | 31.3 ± 13.6 |
| CD4$^-$CD8$^+$CD25$^+$ | 6.1 ± 2.8 | 6.9 ± 1.1 | 4.1 ± 0.7 | 1.8 ± 1.0 | 1.6 ± 0.4 | 7.3 ± 3.4 |
| γδ$^+$CD25$^+$ | 0.2 ± 0.1 | 0.3 ± 0.1 | 0.2 ± 0.1 | 0.8 ± 0.3 | 1.3 ± 0.3 | 2.3 ± 0.8$^{dg}$ |

Figures 29A, 29B, 29C, 29D, 29E, 29F, 29G, 29H, 29I, 29J, 29K:
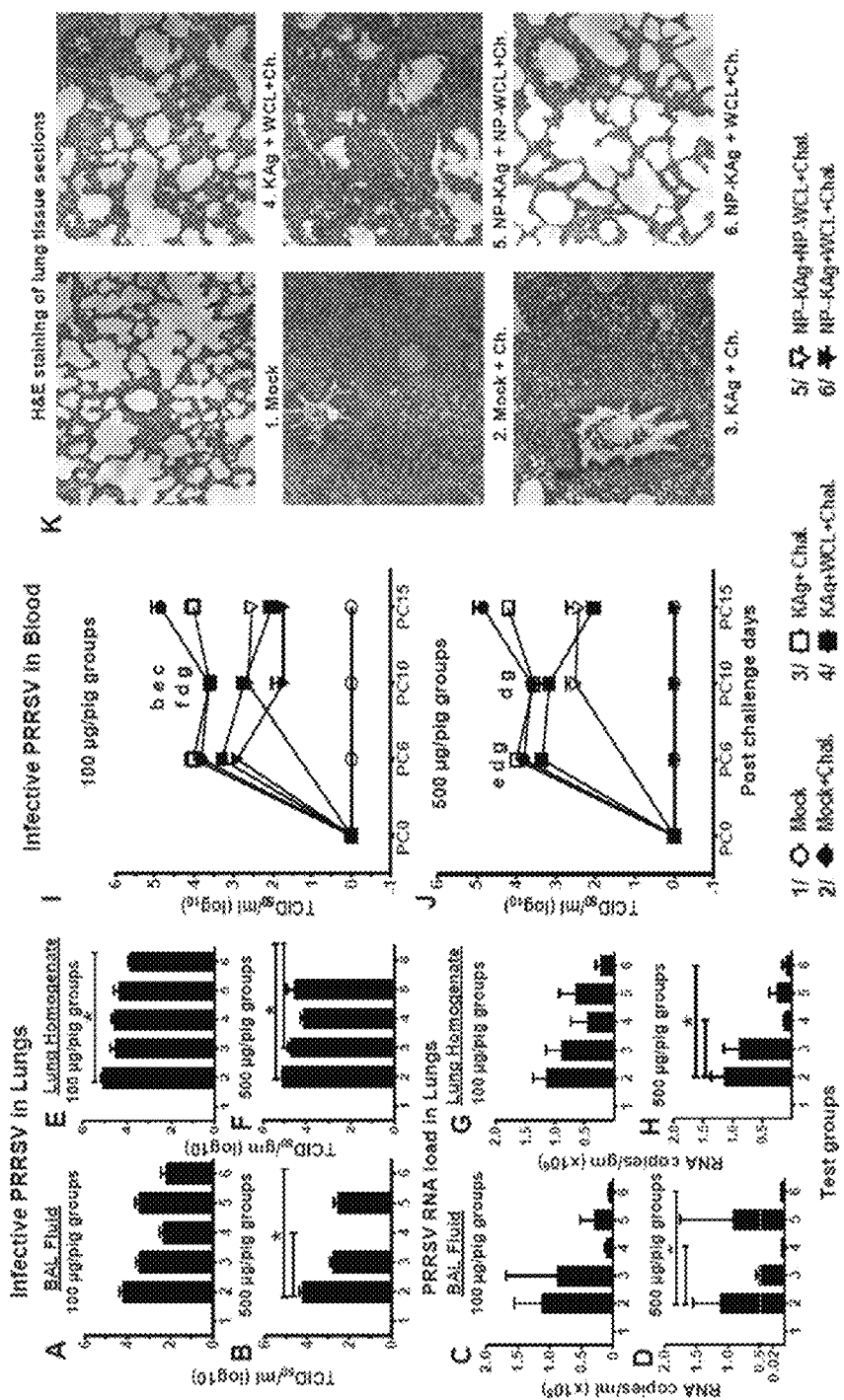
FIGS. 29A-29K shows the complete clearance of replicating PRRSV from the lungs and blood of pigs vaccinated with adjuvanted NP-KAg (500 µg/pig dose) vaccine. Pigs were vaccinated and challenged as described in figure legend 2. (A, B) BAL fluid, (E, F) lung homogenate, and (I, J) plasma samples collected at indicated PCs were analyzed for the presence of replicating PRRSV titer by indirect immunofluorescence assay. PRRSV viral RNA copy numbers in BAL fluid (C, D) and lung homogenate (G, H) were analyzed by qRT-PCR. (K) Representative images of H&E stained lung sections. Each bar or symbol indicates the mean viral titer or viral RNA copy number of three pigs±SEM. Asterisk or lowercase alphabet indicates statistically significant difference between indicated pig groups as described in methods.

Reduced Lung Pathology, Complete Clearance of Replicating PRRSV, and Reduced Viral RNA Load in Adjuvanted NP-KAg Vaccinated Pigs In order to assess the efficacy of the vaccine combinations, the viral clearance was estimated in BAL fluid, lung parenchyma, and blood of heterologous virus challenged pigs. In the BAL fluid of groups 4 and 6 pigs (100 µg dose) the replicating viral titer was reduced compared to group 2 animals, but were comparable to other vaccinated groups. However, in the lung homogenate of group 6 pigs the viral titer was significantly reduced (FIGS. 29A & E) compared to group 2 pigs. In pig groups 4 and 6 (500 µg dose), the replicating 266 virus was absent in the BAL fluid (FIG. 29B); but it was completely cleared in the lungs (lung homogenate) of only group 6 pigs (FIGS. 29E & F). Further, in groups 4 and 6 (100 µg dose) the viral RNA copy numbers were reduced in both the BAL fluid and lung homogenate (FIGS. 29C & G). While in the same groups with 500 µg vaccine dose a significant reduction in the viral RNA load was detected compared to group 2 pigs (FIGS. 29D & H). The data indicated that adjuvanted 500 μg of NP-KAg vaccine dose was efficacious in total clearance of replicating challenged heterologous PRRSV both from the pig lungs and from circulation. In the blood of pig groups 4, 5, and 6 (100 μg dose), a significantly reduced PRRSV titer was detected compared to groups 2 and 3 at PC 10 (FIG. 29I). Again in group 6 pigs (500 μg dose), the replicating PRRSV was completely absent in the blood of virus challenged pigs, at all the tested PCs (FIG. 29J).

Microscopic examination of H&E stained lung sections revealed severe pneumonic lesions with massive infiltration of mononuclear cells with perivascular cuffing in group 2 and 3 pigs. In contrast, remarkable reduction in inflammatory cells infiltration in adjuvanted 500 μg of NP-KAg vaccine dose received pigs was observed compared to all other groups (FIG. 29K).

Adjuvanted NP-KAg Induced High Avidity PRRSV Specific Antibodies

Figures 31A, 31B, 31C, 31D, 31E, 31F:
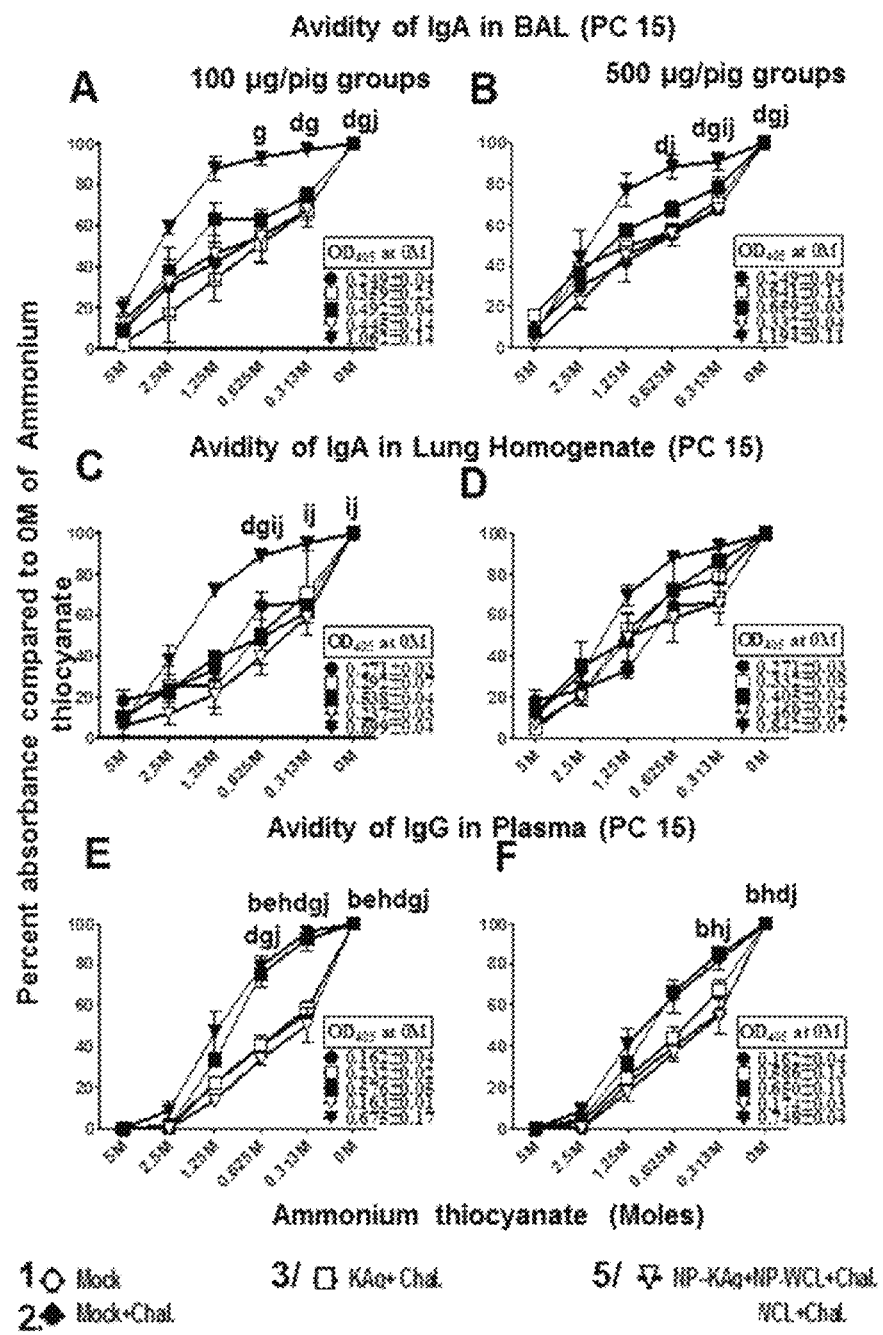
FIGS. 31A-31F shows the high avidity PRRSV specific antibodies produced in pigs vaccinated with adjuvanted NP-KAg vaccine. Pigs were vaccinated or unvaccinated with indicated vaccine and adjuvant combination and challenged with PRRSV MN184. The lung and blood samples were analyzed for avidity of PRRSV specific IgA: (A, B) BAL fluid; (C, D) lung homogenate; (E, F) PRRSV specific IgG in plasma samples by avidity ELISA. Each symbol indicates the mean percent retained absorbance compared to control ($NH_4CN$ at 0 M=100% absorbance)±SEM of three pigs. OD405 at 0 M indicate the mean OD±SEM of three pigs of the indicated group at 0M or no treatment of Ammonium thiocyanate. Lowercase alphabet indicates statistically significant ($p<0.05$) difference between the two indicated pig groups as described in materials and methods. A similar trend in result was obtained in an independent second experiment.

The binding strength of heterogeneous polyclonal antibodies to cognate antigens is defined as avidity (151). At PC 15 in group 6 pigs an increased avidity of PRRSV specific lung IgA and plasma IgG compared to other test groups were detected (FIG. 31). In particular, significantly higher avidity of IgA in BAL and lung homogenate in group 6 pigs compared to other test groups was detected (FIGS. 31A, B & C). Similarly, comparably increased avidity of IgG was observed in lung homogenate of group 6 pigs compared to other test groups. Surprisingly, avidity of IgG in plasma was high and comparable in pig groups 4 and 6 (FIGS. 31E & F). However, at PC 0 and 6, there was no difference in the avidity of IgG in plasma among all the tested groups. Overall, these data indicated increased production of high avidity PRRSV specific antibodies in adjuvanted NP-KAg vaccinated pigs both in the lungs and blood.

Adjuvanted NP-KAg Induced Balanced Th1 and Th2 Response Indicating IgG Isotypes

Typically killed vaccines elicit predominantly Th2 responses, but NP-based vaccines drive either Th1-Th2 balanced or Th1 biased responses (138). Therefore, PRRSV specific IgG sub-isotypes were quantified, and in pigs higher IgG1 and IgG2 levels indicate Th2 and Th1 biased response, respectively (149). The levels of PRRSV specific IgG1 and IgG2 in plasma (PC 0) and in lung homogenate (PC 15) in pig groups 2 to 5 were low and comparable, but their levels were significantly higher in the plasma (PC 15) of group 6 pigs (500 μg vaccine dose) compared to other groups (FIG. 32A). To assess Th2 or Th1 biased response, the ratio of IgG1/IgG2 was assessed, wherein the ratio of >1 or <1 indicates Th2 or Th1 biased response, respectively. In group 6 pigs at PC 15, balanced response (ratio close to 1) was detected both in the plasma and lung homogenate, while groups 3 and 4 pigs had Th2 biased antibody response (FIG. 32B). A similar trend was observed in pigs received 100 μg vaccine dose (FIGS. 32A & B). The data indicated that adjuvanted NP-KAg elicited Th1-Th2 balanced response.

Discussion

PLGA nanoparticle has the ability to mediate activation, maturation, and antigen presentation by APCs (132). It facilitates sustained release of vaccine Ags and mediates induction of robust B and T-cell responses (133). PLGA (75:25) was used to entrap UV-inactivated PRRSV (VR2332) Ags, and in vitro protein release profile from entrapped nanoparticles was consistent with other studies (134). Size and surface characteristics of NPs play an important role in their opsonization and clearance kinetics (135). The NP-KAg was 400-700 nm in diameter, which was ideal for uptake by mucosal M-cells and APCs (136). A few changes were made to NP-KAg preparation compared to an earlier study (123), aimed to enhance the vaccine immunogenicity. NP-KAg were made hydrophilic (by Polaxamer 188) to facilitate easy uptake by APCs (41), sucrose was used as a stabilizer and $Mg(OH)_2$ to buffer the acidic pH generated during hydrolysis of PLGA (137). Such a modified NPs vaccine delivered intranasally elicits enhanced and prolonged IgG and IgA production (138).

PLGA vaccine coadministered with a potent adjuvant elicits protective immune responses (119). Adjuvant *M. tb* WCL was demonstrated to boost the efficacy of PRRS-MLV (28), and also a single dose of NP-KAg elicits partial cross-protective immunity in pigs (123). To further potentiate the efficacy of NP-KAg, the vaccine was coadministered with entrapped/unentrapped *M. tb* WCL and evaluated various immune correlates of protection in heterologous PRRSV (MN184) challenged pigs. The results indicated that unentrapped *M. tb* WCL significantly potentiated the immunogenicity of NP-KAg vaccine (group 6 pigs), as indicated by the following immune correlates: (i) increased PRRSV specific IgG and IgA titers with enhanced antibody avidity; (ii) balanced Th1 and Th2 responses with enhanced VN titers; (iii) increased secretion of Th1 (IL-12 and IFN-γ) and Th2 (IL-4) cytokines, with enhanced frequency of ISCs and IFN-γ producing $CD4^+$, $CD8^+$, $CD4^+CD8^+$ T cells, $\gamma\delta^+$ 305 T cells, and NK cells, and expanded frequency of APCs; (iv) reduced production of immunosuppressive cytokines (IL-10 and TGF-β) and importantly, (v) complete clearance of the replicating challenged virus from both the lungs and blood.

PRRSV primarily infects both interstitial and alveolar Mφs (118), and greater than 90% BAL cells are Mφs (62), while lung MNCs are rich in both interstitial Mφs and lymphocytes. $CD11c^+$ APCs are present in both BAL fluid and lung parenchyma, but they differ in their antigen presentation potential, with the former activates only antigen primed T cells and the latter activates both naïve and antigen primed T cells (139). Therefore, responses in the BAL fluid, lung homogenate, and lung MNCs were analyzed.

Both at mucosal sites and blood of adjuvanted NP-KAg vaccinated (group 6) pigs, significantly enhanced levels anti-PRRSV antibodies were detected, along with increased antibody avidity and VN titers. The avidity of polyclonal antibodies in vaccinated or infected animals is shown to be positively correlated with VN titers (140). Consistent with a previous report, avidity of PRRSV specific IgG levels in the plasma of group 6 pigs increased gradually and reached the peak at post-challenge day 15, which was due to gradual domination of high affinity antibody secreting B cell clones (140). Nanoparticles have been shown to interact with pathogen recognition receptors on APCs (B cells) leading to affinity maturation and production of high avidity antibodies (141). Further, the avidity results were correlated with PRRSV VN titers both at mucosal surfaces (IgA) and lung parenchyma (IgA and IgG), which contributes to protection.

Typically killed vaccines elicit predominantly Th2 response, but to efficiently clear virus infected cells balanced Th1 and Th2 responses are necessary (142). NPs based vaccines drive either balanced or Th1 biased responses (138). In group 6 pigs, enhanced and balanced Th1-Th2 humoral and cell-mediated immune (CMI) responses were detected. VN antibodies against putative neutralizing epitopes on PRRSV GP5 and M glycoproteins play an important role in PRRSV clearance (131). In group 6 pigs, high levels of cross neutralizing VN titers were detected against challenged PRRSV strain (MN184), and also increased VN titers were detected against other genetically divergent viruses including the type I virus strain, indicating the presence of a broadly reactive VN response elicited by adjuvanted NP-KAg.

A NK cell is a major innate immune player in antiviral defense. In the group 6 pigs, the population of IFN-γ+ NK cells was significantly upregulated. PRRSV suppresses the NK cell activity (95, 143), but adjuvanted NP-KAg appears to rescue the NK cell function. Increased production of IL-12 in the lungs of group 6 pigs can influence the NK cell function. The γδ T cells are present in high frequency in pigs and are involved in both innate and adaptive immunity. Enhanced frequency of activated γδ T cells was observed in group 6 pigs. A robust CMI response is important for complete protection against PRRSV infection (28). A crucial Th1 cytokine, IFN-γ, is produced by NK cells, γδ T cells, CD4+ and CD8+ T cells, and CD4+CD8+ T cells. In group 6 pigs, increased frequency of IFN-γ secreting lymphocyte and their subsets were identified. In addition, significantly reduced production of IL-6 in group 6 pigs indicated the absence of inflammatory reaction at PC 15 in group 6 pigs. The observed enhanced CMI response in NP-KAg received pigs can be due to PLGA mediated cross-presentation of entrapped Ags to CD8+ T cells by APCs in vivo (144). An enhanced memory response is associated with production of high avidity antibodies and enhanced B and T cell responses (145). Thus, the immune response results in post-challenged pigs indicate the possible induction of a strong memory response in adjuvanted NP-KAg received pigs.

The importance of immediate availability of unentrapped potent adjuvant to intranasally delivered NP-KAg vaccine was critical to elicit a robust immune response, because inadequate anti-PRRSV response with partial viral clearance was observed earlier with only NP-KAg vaccine (123), and now in NP-KAg and NP-*M. tb* WCL received pigs (group 5). Consistent with these results, PLGA entrapped Hepatitis B subunit vaccine coadministered with an encapsulated adjuvant failed to induce adequate antibody response (146). Further, both vaccine and adjuvant unentrapped formulation (group 4 pigs) elicited robust Th2 biased responses with incomplete clearance of challenged PRRSV, confirming the necessity of a PLGA system to deliver PRRSV KAg. Consistent with the presence of low PRRSV RNA copy number and absence of replicating virus in adjuvanted NP-KAg vaccinated (group 6) pig lungs, previous reports have shown that qRT-PCR fails to differentiate infectious and noninfectious virus and the inactivated PRRSV is relatively stable in the environment (125). Samples with low levels of PRRSV RNA copies failed to replicate in cell culture (56).

The results have shown a potent adjuvant like *M. tb* WCL can induce a better cross-protective immunity by PLGA-NanoPRRS. But, *M. tb* grows slowly in culture and it is a biosafety level-3 (BSL-3) pathogen. Thus, large-scale production of *M. tb* WCL represents risk, time, and cost. Therefore, a cost-effective potent alternate adjuvant to use with PLGA-NanoPRRS is ideal. Four nonpathogenic species of *Mycobacterium* whose cell wall and protein composition is comparable to *M. tb* have been identified. They include *M. smegmatis, M. vaccae, M. alvei*, and *M. fallax*. These four mycobacterial species are fast-growing, nonpathogenic, like *M. tb* they possess rough colony morphology with cord formation, cell wall characteristics close to *M. tb*, non-commensal of pigs, BSL1 facility is sufficient to grow them, and available in American Type Culture Collection (ATCC) (112). Moreover, *M. smegmatis* preparations are used as candidate adjuvants to generate protective immune responses against pathogens (113, 114). In a pilot study, PRRS-MLV and *M. smegmatis* WCL were co-administered intranasally to pigs and challenged with a heterologous virus; clinically, pigs did not have PRRS symptoms, and immunologically detected enhanced IFN-γ and IL-12 production compared to control PRRS-MLV group. *M. vaccae* preparation was used as an adjuvant in oral vaccines (115, 116).

A PLGA based delivery system reduces the required vaccine dose by several folds, demonstrated recently with a PLGA NPs-based tumor peptide vaccine, wherein a 63 times reduced vaccine dose elicited a comparable response (147). Since PLGA NPs are getting global recognition, they are an effective delivery system for inactivated mucosal vaccines, moreover their size, contents, and cell targeting properties could be engineered (119). In conclusion, intranasal delivery of a potent adjuvanted PLGA nanoparticle-entrapped inactivated PRRSV vaccine in pigs has the potential to induce superior cross-protective immunity. Further validation of this vaccine formulation involving large numbers of pigs will envisage its field of application. This strategy can also be applied to control important human respiratory pathogens.

Example 4

PRRSV VLPs

PRRSV excretes from all the body secretions at low levels or perhaps intermittently in saliva, nasal secretions, urine, milk, colostrum, feces of infected pigs, and also in semen of infected boars [174-179]. The PRRSV elicits poor innate and adaptive immune responses in infected pigs [57, 180, 181, 12], associated with increased immunosuppressive response [77, 182, 183, 48, 95]. As a result in PRRSV infected pigs there will be incomplete viral clearance and increased susceptibility to secondary microbial infections [125, 165, 12, 184, 15]. Since the 1990s within PRRSV genotypes (European-Type I and North American-Type II) there have been constant emergence of several genetically variant subtypes and strains in the US, resulting in a display of significant differences in their pathogenicity in pigs [38]. Therefore, immunity induced by one PRRSV strain in pigs may provide partial to no protection to reinfection [185, 186, 117, 187]. Within North American PRRSV isolates genetic variation is from 84-100%, and one such field isolate, MN184, is a virulent and genetically highly variant strain [38]. Although many reports have demonstrated satisfactory immunity induced by MLV-PRRS in growing pigs, others reported reversion in virulence of vaccine virus and transmission to unvaccinated pigs and sows [96, 32, 97]; also recombination between vaccine and field strains [188, 88]. Thus, prevention of virus transmission from the infected pig herd is critical to control PRRS. All these limitations made the research on development of a better cross-protective killed PRRSV vaccine a high priority.

Activated innate immune response at mucosal sites play a major role in mucosal immunity against enteric and lung infections [189]. Immune responses elicited by potent mucosal vaccines is associated with enhanced cytotoxic T-lymphocyte (CTLs) and central memory immune responses, targeted to a greater number of viral structural proteins and to many conserved epitopes, resulting in enhanced cross-protective immunity against genetically divergent field viral strains [190, 191, 54, 192-194]. Nanotechnology has become one of the important research endeavors of future vaccinology approach. Nanoparticles offer the advantage of increasing the potency of drug and vaccine delivery, possess adjuvant properties, and thus improves the vaccine efficacy [60]. Due to inherent ability of APCs to readily phagocytose particulate structures, PLGA nanoparticle-based vaccines and VLPs prime long-lasting antibody and T cell responses [195-197]. Moreover, due to the nature of PLGA nanoparticles to protect entrapped vaccine antigens from proteases-mediated degradation at mucosal surfaces, nanoparticle-based vaccine delivery is gaining increased attention to induce protective mucosal immunity. A killed influenza virus vaccine entrapped in nanoparticles administered intranasally to mice, rabbits, and pigs induced protective immunity, and immune responses elicited in pigs by intranasal delivery was significantly higher than intramuscular immunization [25]. PLGA nanoparticles entrapped vaccines containing hepatitis B, rotavirus, influenza, or parainfluenza viruses delivered to mucosal sites of mice generated protective immunity [54, 25, 55, 102]. Biodegradable and biocompatible PLGA nanoparticles are free from any toxicity and have proved safe to use in humans. PLGA polymers are used to prepare suture materials and are approved materials by the U.S. Food and Drug Administration [198, 90, 92]. It has been demonstrated that cross-protective immunity against PRRSV can be elicited with the help of PLGA nanoparticle-based PRRSV vaccine. However, for large-scale production of such a particulate vaccine, a cost-effective strategy in bulk preparation of vaccine antigens is essential.

Recombinant baculovirus-mediated insect cell production technology allows rapid production of virus-like-particles (VLPs) [199]. Such technology has been proved effective for both enveloped and non-enveloped viruses like calici, influenza, parvo, polyoma, reo, paramyxo, orthomyxo, hepatitis C, Ebola, Marbug, Chikungunya, SARS corona etc., (reviewed in [200, 201]). Co-expression of multiple (2-4) viral surface proteins still results in VLPs that are indistinguishable from authentic viral particles [202, 203]. In addition, production of a vaccine with DIVA (differentiation of infected from vaccinated animals) potential is possible with VLP based subunit vaccines. Using already published standard procedures, PRRSV-VLPs can be prepared. VLP based vaccines have several advantages over the conventional vaccine antigens; they are as follows. (i) Extremely large-quantities of correctly folded recombinant proteins can be produced in high density cell-culture conditions in eukaryotic cells, thus baculovirus system is amenable to scale-up for large-scale vaccine production [204]. (ii) Insect cells based vaccine production can be done without the need of mammalian cell-derived supplements, thus the risks of co-culturing opportunistic pathogens is minimized. (iii) There is no threat from baculovirus in vaccinated individuals because this virus has a very narrow host-range in a few species. (iv) VLPs are quite stable with no alteration of particle morphology or reduction in immunogenicity even after 9 weeks storage at room temperature [205]. (v) To further boost the vaccine potency, PRRSV-VLPs can be entrapped in PLGA nanoparticles and delivered to pigs, intranasally. (vi) Unlike MARC-145 cell derived semi-purified crude inactivated PRRSV, the dose of VLPs in a Nano-PRRSV-VLP vaccine is quantifiable.

VLPs promote immunogenicity and have been developed for several viral vaccines. Papilloma virus VLP vaccine is licensed for use in humans, and a few other VLP vaccines are in phase I clinical trial [201]. Vaccination of pigs using less than 10 μg dose of porcine parvo virus VLPs in a water-in-mineral oil emulsion adjuvant was found to be highly immunogenic, and also efficient in preventing trans-placental virus transmission and number of reproductive failures in gilts [206]. The VLPs of hepatitis B surface antigen entrapped in PLGA-nanoparticles have been found to be effective in trans-mucosal delivery of the vaccine, representing an approach for the delivery of VLPs [207]. Also PLGA nanoparticle-based vaccine delivers the associated VLPs to the immune system in a controlled manner for up to 14 days, without any compromise in its immunogenicity [207]. Delivery of PLGA nanoparticle-entrapped PRRSV-VLPs vaccine can elicit an adequate cross-protective immune response in pigs, indicated by enhanced-neutralizing antibody titers and increased clearance of challenged virulent heterologous PRRSV.

PRRSV Isolates for Candidate Vaccine Construction

Type I virus, SD01-08, and Type II virus, SD09-28, cab be used. The SD01-08 isolate represents a group of emerging Type I PRRSV in North America, which has been used in our previous studies for vaccine development [170, 171]. The PRRSV SD09-28 was originally obtained in 2009 from a PRRSV-infected farm, which represents current field circulation strains (contains 1-8-4 RFLP pattern in ORFS).

Cloning of PRRSV Surface Protein Genes and Generation of PRRSV-VLPs in Baculovirus System Recombinant baculovirus protein expression system is an established system [208, 209]. Four important PRRSV surface protein genes, GP3, GP4, GP5, and matrix proteins can be amplified by RT-PCR from the viral RNA and subcloned into a baculovirus transfer vector 'pAcAB4' (BD Biosciences, BD BAculoGold™ Cat#554770) using Rapid Ligation Kit (Promega Corp.). Earlier, co-expression of 3 to 4 viral capsid proteins to make VLPs of influenza virus [210] and bluetongue virus [211] in insect cells have been demonstrated. To generate PRRSV-VLPs, pAcAB4 vector containing PRRSV genes constructs in the correct orientation can be co-transfected to Sf9 insect cells using Linearized Baculovirus DNA Transfection Kit (BD Biosciences, BD BaculoGold™). To detect generated PRRSV-VLPs, media from the transfected Sf9 cells can be examined using PCR for the presence of PRRSV nucleotide sequences in the recombinant baculovirus. Further, PRRSV-VLPs can be visualized with the help of Transmission Electron Microscope (TEM) (Hitachi S-3500N), by comparing side-by-side with sucrose purified wildtype PRRSV.

Preparation of Nano-PRRSV-VLPs

PLGA nanoparticle-based PRRSV vaccine can be prepared as previously described [60, 198]. Briefly, PRRSV-VLPs of both the PRRSV strains can be entrapped in PLGA nanoparticles by double emulsion method, separately. The following chemicals can be used to make the nanoparticles hydrophilic and stable, such as, poloxamer 188, sucrose, $Mg(OH)_2$, polyvinyl alcohol [212, 41, 213]. Briefly, 15% of PLGA (75/25) can be dissolved in dichloromethane and PRRSV-VLPs, and the mixture can be homogenized by sonication, then added to aqueous solution of polyvinyl alcohol, and again homogenized. Nano-PRRSV-VLPs can be stirred at room temperature, washed, freeze-dried, and stored at 4° C. To use on control pigs, empty PLGA nanoparticles can be prepared by a similar method.

Characterization of Nano-PRRSV-VLPs:

The concentration of VLPs in Nano-PRRSV-VLPs can be determined as described previously [41] using a BCA protein assay kit (Biorad, CA). Morphology (size and shape) of Nano-PRRSV-VLPs can be determined by coating the freeze-dried vaccine powder with gold-platinum under vacuum with the help of an ion coater and examined using TEM at 10 KV. Further, phagocytosis of Nano-PRRSV-VLPs by pig alveolar MΦs can be determined by treating BAL cells with freeze-dried Nano-PRRSV-VLPs or PRRSV-VLPs and immunostained for confocal microscopy (Leica confocal microscope). Further, to determine Nano-PRRSV-VLPs induced activation of alveolar MΦs, treated BAL cells can be subjected to phenotypic analyses using FACS Aria II (BD Biosciences) flow cytometer.

Evaluation of Efficacy of Nano-PRRS-VLPs Vaccine in Pigs

Conventional 4-6 weeks old healthy pigs can be procured (n=35) from a SPF swine herd free from PRRS at The Ohio State University, OARDC. Serum samples collected before starting the study can be confirmed negative for PRRSV antibody. Pigs can be unvaccinated (group 1), vaccinated with empty nanoparticles (group 2), equal amounts of Nano-PRRS-VLPs of both the viral genotypes (group 3&4), PRRS-VLPs (groups 5&6), or with a commercial killed PRRSV vaccine (group 7), inoculated twice at 2 weeks interval (Table 4). On day post-vaccination (DPV) 28, pigs can be challenged using a heterologous PRRSV strain, MN184 [38, 214] ($1 \times 10^6$ pfu/pig). Animals can be monitored daily for clinical disease and rectal temperature, and on every 3rd day record body weight. Serum samples can be collected at different DPV as indicated (Table 4), aliquoted and stored at −70° C. Pigs can be euthanized on DPV 42 (2 weeks post-challenge) and the lungs and lymph nodes can be examined for gross lesions. The lung tissue samples can be collected in neutral buffered formalin for histological studies. During necropsy blood, bronchoalveolar lavage (BAL) fluid, tracheobronchial lymph nodes (TBLN), tonsils, and lung tissue can be collected for virus detection; and also to isolate PBMC, TBLN mononuclear cells (MNC), BAL cells, and lung MNC for immunological studies [47, 162, 95].

TABLE 4

Evaluation of the efficacy of Nano-PRRS-VLPs in pigs Groups 2-6: two doses of vaccine, $1^{st}$ dose intranasally, and 2 weeks later the $2^{nd}$ dose (booster) by intramuscular route. Group 7: administered by intramuscular route.

| Pigs group | Vaccine combination (n = 5 pigs/group) | Vaccine dose per pig Two doses | PRRSV challenge MN184 (DPV 21) | Collection of blood samples (DPV) |
|---|---|---|---|---|
| 1 | Mock | None | No Challenge | 0, 14, 28, 35, 42 |
| 2 | Mock | Empty nanoparticles | Challenge | 0, 14, 28, 35, 42 |
| 3 | Nano-PRRS-VLPs | 50 μg/dose/pig | Challenge | 0, 14, 28, 35, 42 |
| 4 | Nano-PRRS-VLPs | 250 μg/dose/pig | Challenge | 0, 14, 28, 35, 42 |
| 5 | PRRS-VLPs | 50 μg/dose/pig | Challenge | 0, 14, 28, 35, 42 |
| 6 | PRRS-VLPs | 250 μg/dose/pig | Challenge | 0, 14, 28, 35, 42 |
| 7 | Commercial killed PRRSV vaccine | As per recommendation of the manufacturer | Challenge | 0, 14, 28, 35, 42 |

Detection of Immune-Correlates of Protection and Cross-Protective Immunity

Determine Humoral Immunity

To compare humoral immune responses, all the serum samples (Table 4) can be evaluated using the IDEXX HerdChek® PRRS 3XR ELISA and virus neutralization assay [179, 165, 164]. To assess cross-protective neutralizing antibody titer induced in Nano-PRRS-VLPs vaccinated pigs, a panel of six field isolates can be used in the assay. Twenty three field PRRSV isolates have been collected at the SD Animal Disease Diagnostic Laboratory since 2010. The GP5 sequence data can be entered into the current PRRSV database (prrsvdb.org/) for phylogenetic analysis using the method described previously (127). Six isolates that represent the current circulating field strains (most recently evolved PRRSV) can be selected, and used in the assay to evaluate the depth of protection induced of the vaccine.

Quantification of Viral Load in Tissues and Viremia

To quantify PRRSV RNA and to determine the viral load, serum samples and tissue samples (lungs, tonsils, and TBLN) can be analyzed by quantitative RT-PCR and cell culture immunofluorescence assay [214, 163, 215].

Phenotypic Analysis of Immune Cells

TBLN-MNC, BAL cells, lung MNC, and PBMC can be immunostained to determine the frequency of both lymphoid and myeloid immune cells by flow cytometry [48].

Cytokines Analysis:

Serum and BAL samples can be analyzed for cytokines: innate (IFN-α); pro-inflammatory (IL6); T-helper 1 (Th1) (IFN-γ and IL-12); and immunosuppressive (IL-10 and TGF-β by ELISA [48].

NK Cell-Cytotoxicity Assay

Innate NK cell-mediated cytotoxicity can be determined using lung MNC and PBMC as a source of NK cells (effectors) against K-562 target cells as described previously [12].

Results

Results of the study can be analyzed using a non-parametric statistical test (GraphPad prism 5). Based on clinical parameters, viral load, frequency of different immune cells, cytokines profile, and NK cell function, the immune correlates of protection in vaccinated, virus challenged animals can be determined.

Varying degrees of cross-neutralizing antibody response against a panel of field PRRSV isolates in pigs vaccinated with Nano-PRRSV-VLPs can be detected. Vaccinating with two doses of Nano-PRRSV-VLPs vaccine can result in better virus clearance from the serum and lungs of pigs compared to results showed in preliminary data. Also in vaccinated virus challenged pigs, an increased PRRSV specific adaptive immune response associated with increased production of cytokines and upregulated expression of CD4 and CD8 markers on lymphocytes present at both systemic and mucosal sites can be detected. Enhancing the efficacy of PRRS-VLPs alone or as a candidate vaccine co-administered with potent adjuvants, similar to a published vaccine studies using parvovirus VLPs in pigs, can be achieved [206].

Example 5

Role of UEA in PLGA-NanoPRRS Vaccine

NP-KAg can be targeted to M cells present in the pig upper respiratory tract. Earlier reports have showed that UEA entrapped (inside) PLGA nanoparticle vaccine, inoculated intranasally to mice significantly enhances the production of specific SIgA. Hypothetically, surface anchored UEA in nanoparticle vaccine should be better than entrapped UEA in delivery of its cargo to M cells. In humans, nanoparticle-mediated targeted delivery of drugs and biomarkers are achieved by surface anchoring the nanoparticles with a targeting molecule (152, 153), which also significantly reduces the required dose. Therefore, to enhance the efficacy of NP-KAg vaccine and to make it cost-effective both strategies will be tested in the pig system.

Based on previous results (123) and results by others (154-158); undoubtedly, the NP-KAg vaccine has the potential to provide cross-protective immunity against PRRS. Results of in vitro studies can help understand the role of UEA in targeted delivery of NP-KAg to M cells. This study can help reduce the vaccine dose and further enhance the cross-protective efficacy to PRRSV. In addition, studies with NP-KAg indicate a potent adjuvant can be used to elicit better immune responses and viral clearance both from the lungs and circulation. The adjuvant M. tb WCL can be replaced with another candidate potent adjuvant. These studies analyze the adjuvant effects of four selected nonpathogenic mycobacterial species derived WCL, coadministered intranasally with NP-KAg-UEA.

Experimental Methods

Animal Groups and Inoculations

PRRSV antibody free 4-6 weeks old SPF pigs (n=60, 6 pigs per group) will be randomly assigned into one of the 10 groups. As per the statistical power analysis (ebook.stat.ucla.edu/cgi-bin/engine.cgi) six pigs/group can provide a Power of at least 0.8 ($\alpha=0.05$). Pigs can be unvaccinated (mock—group 1) or vaccinated with sham nanoparticles (group 2), killed PRRSV (group 3&4), or with indicated NP-KAg preparations (group 5-10) (Table 5). Pigs can be vaccinated with $5\times10^5$ TCID$_{50}$ (~100 µg) (groups 3, 5, 7, & 9) or $2.5\times10^6$ TCID$_{50}$ (~500 µg) (groups 4, 6, 8 & 10) per pig dose of indicated NP-KAg vaccine formulations, coadministered with M. tb WCL (1 mg/pig), twice, intranasally at two weeks interval. Note that, 100 and 500 µg of vaccine dose refers to protein equivalent of NP-KAg. Just before vaccination freeze-dried vaccine and adjuvant can be reconstituted in PBS, and the required amount for each vaccine dose can be mixed and the quantity adjusted to 4 ml in PBS. Pig groups 2 to 10 can be challenged using the virulent heterologous PRRSV stain MN184 (38) ($5\times10^5$ TCID$_{50}$ in 4 ml) at two weeks post-booster [28 dpv (day post-vaccination], intranasally; while the mock group can receive equal amount of the MARC-145 cell culture supernatant.

TABLE 5

| Pig Groups | (6 pigs/Gp) Pig groups (n = 60) |
|---|---|
| 1 | Mock |
| 2 | Sham nanoparticles |
| 3&4 | Killed PRRSV |
| 5&6 | NP-KAg |
| 7&8 | NP-KAg -surface UEA |
| 9&10 | NP-KAg - entrapped UEA |

Clinical Monitoring, Blood, and Tissue Sampling

Pigs can be monitored daily after PRRSV challenge for disease symptoms such as respiratory distress, cough, and food intake. Body temperature can be recorded every day during first 7 days, and the body weight measured every week until dpv 56. Blood samples can be collected on 0, 3, 7, 14, 21, 28, 28, 35, 42, 49, and 56 dpv in EDTA, and the plasma can be aliquoted and stored at −70° C. Pigs can be euthanized at four weeks post-challenge (56 dpv), and the lungs and lung draining tracheobronchial lymph nodes (TBLN) can be scored for macroscopic lesions (159). Lung samples can be collected in neutral buffered formalin, sectioned (5 µm) and examined after subjecting to H&E and immunohistochemistry staining for microscopic lesions (121). The slides can be scored by a board certified veterinary pathologist, without providing the sample history. Samples of the lungs, tonsils, and TBLN can be frozen to determine the PRRSV titer later. Blood samples collected in anticoagulant solution and lung tissue samples collected in DMEM can be processed on the same day to isolate respective mononuclear cells (160, 161, 162). Lung lysates prepared from the lung samples and BAL fluid can be aliquoted and stored at −70° C. (12, 48).

Quantification of Viral Load

PRRSV load and titer in plasma and tissue samples (lungs, tonsils, and TBLN) can be quantified by estimating the viral RNA by RT-PCR (163), and also by indirect immunofluorescence assay to determine the replicating viral titer (48) (FIG. 35)

Evaluation of Innate, Humoral, and Cell-Mediated Immune Responses

To analyze cross-protective immune response six genetically variant PRRSV isolates can be selected based on the GP5 sequence data that represent the current circulating PRRSV in the field from the database (prrsvdb.org). Semi-purified crude PRRSV Ags prepared from six field PRRSV isolates can be used to stimulate PBMCs and lung MNCs to analyze IFN-$\gamma^+$ lymphocytes frequency by ELISPOT assay (128) (FIG. 36). As controls, cells stimulated with PHA (10 µg/ml) or unstimulated can be included. Plasma samples can be evaluated using the IDEXX HerdChek® PRRS 2XR ELISA for viral antibodies (48). Cross-protective VN titers in plasma samples collected at 0, 28, 42, and 56 dpv and lung lysates collected at dpv 56 can be determined against six PRRSV field isolates (164, 165) (FIG. 37). Avidity of PRRSV specific IgA and IgG in BAL fluid, lung lysates, and plasma samples will be determined (166, 167) (FIG. 38). Plasma samples collected at dpv 0, 3, 7, 14, 21, 28, 28, 35, 42, 49, and 56 and lung lysates will be analyzed for: innate (IFN-$\alpha$, IFN-$\beta$); pro-inflammatory (IL1$\beta$, IL6, and TNF$\alpha$); T-helper 1 (Th1) (IFN-$\gamma$ and IL-12); Th2 (IL-4); and immunosuppressive (IL-10 and TGF-$\beta$) cytokines by ELISA (12).

Adjuvant Effects of Nonpathogenic Mycobacterial Adjuvants to NP-KAg-UEA Vaccine

Experimental Methods

Production of WCL

Four selected non-pathogenic Mycobacterium species (Table 6) can be grown in liquid medium as recommended by ATCC, and WCL can be prepared as described previously (168). Briefly, live bacteria can be harvested and washed twice using PBS (pH 7.4) and suspended (2 g/ml) in PBS containing 8 mM EDTA, proteinase inhibitors, DNase, and RNase. Cells can be disrupted by using the Bead Beater until approximately 90% breakage is obtained (monitored by acid fast staining), centrifuge at 3,000×g to pellet unbroken cells and insoluble cell wall components, and the supernatant (WCL) can be harvested. The protein content and endotoxin levels in the WCL can be quantified using the kits, and the aliquots will be stored at −70° C. The mycobacterial WCL preparation contains water-soluble proteins, lipids, and carbohydrates.

TABLE 6

| Pig Groups | (6 pigs/Gp) Pig groups (n = 60) | Adjuvant |
|---|---|---|
| 1 | Mock | |
| 2 | Sham nanoparticles | |
| 3&4 | NP-KAg -UEA | M. smegmatis |
| 5&6 | NP-KAg -UEA | M. vaccae |
| 7&8 | NP-KAg -UEA | M. alvei |
| 9&10 | NP-KAg -UEA | M. fallax |

Animal Groups and Inoculations

PRRSV antibody free 4-6 weeks old SPF pigs (n=60, 6 pigs/group) can be randomly assigned into one of the 10 groups (Table 6). Pigs can be unvaccinated (mock—group 1), vaccinated with Sham nanoparticles, or vaccinated with $5 \times 10^5$ TCID$_{50}$ (~100 µg) per pig dose (groups 3, 5, 7, & 9), or $2.5 \times 10^6$ TCID$_{50}$ (~500 µg) per pig dose (groups 4, 6, 8 & 10) of NP-KAg-UEA vaccine, coadministered intranasally with indicated nonpathogenic *Mycobacterium* species derived WCL (groups 3 to 10), 1 mg/pig, twice, at two weeks interval. Just before vaccination, freeze-dried vaccine and indicated adjuvant preparations can be reconstituted in PBS, and the required amount for each vaccine dose can be mixed and the quantity adjusted to 4 ml in PBS. Pig groups 2 to 10 can be challenged with the virulent heterologous PRRSV strain MN184 (38) ($5 \times 10^5$ TCID$_{50}$ in 4 ml) intranasally, at two weeks post-booster [28 dpv (day post-vaccination]; while the mock group can receive the cell culture supernatant. Monitoring of clinical signs, collection of blood and tissue samples, quantification of viral load, and evaluation of humoral, innate, and cell-mediated immune responses can be performed as described above.

The Breadth of Cross-Protective Immunity in Adjuvanted Nanoparticle-PRRSV Vaccinated Pigs Against Different Antigenically Divergent Viruses This study can determine how the adjuvanted NP-KAg-UEA vaccine helps in induction of better cross-protective immunity, measured by clinical symptoms, viral clearance, and by immune correlates in growing pigs. In pregnant sows, whether the vaccine formulation could reduce the vertical transmission of the challenged virus to piglets can be investigated.

Experimental Methods:
Animal Groups and Inoculations

PRRSV antibody free 4-6 weeks old SPF pigs (n=66) and pregnant sows at 55 days of gestation (n=9) can be randomly assigned into one of the indicated groups (Table 7). Pigs can be unvaccinated (mock—group 1), vaccinated using sham nanoparticles, or with NP-KAg-UEA vaccine (Table 7a&b), coadministered intranasally with a selected non-pathogenic *Mycobacterium* species WCL (1 mg/pig), twice at two weeks interval. Just before vaccination, freeze-dried vaccine and adjuvant preparations can be reconstituted in PBS and the required amount can be mixed and adjusted to 4 ml in PBS.

TABLE 7a

| GP | (6 pigs/Gp) Pig groups (n = 66) | Challenge PRRSV |
|---|---|---|
| 1 | Mock | |
| 2 | Sham Nanoparticles | VR2332 |
| 3 | Sham Nanoparticles | 10-398 |
| 4 | Sham Nanoparticles | SD03-08 |
| 5 | NP-KAg -UEA | VR2332 |
| 6 | NP-KAg -UEA | 10-398 |
| 7 | NP-KAg -UEA | SD03-08 |
| 9 | PRRS-MLV | VR2332 |
| 10 | PRRS-MLV | 10-398 |
| 11 | PRRS-MLV | SD03-08 |

TABLE 7b

| GP | (3 sows/Gp) Sow groups (n = 9) | Challenge |
|---|---|---|
| 1 | Mock | |
| 2 | Sham Nanoparticles | 10-398 |
| 3 | NP-KAg -UEA | 10-398 |

As a control, pig groups 9 to 11 can be vaccinated using PRRS-MLV as per manufacturer recommendations. Pigs groups 2 to 11 (Table 7a) and groups 2 and 3 (Table 7b) can be challenged with an indicated PRRSV strain, two weeks after booster (28 dpv) ($5 \times 10^5$ TCID$_{50}$ in 4 ml), intranasally; while the mock group can receive equal amount of MARC-145 cell culture supernatant.

The challenge viral strain, PRRSV 10-398 (D6) (accession #10-16734) contains 1-4-4 RFLP pattern in ORFS (169), and it was isolated in 2010 from an infected sow, represents an extremely virulent current field strain in the state of Ohio and other states, which killed 10% of infected sows. The PRRSV strain SD01-08 represents an emerging Type I PRRSV in North America (170, 171). The homologous virus (VR2332 strain) (164, 172) can also be included. Monitoring of clinical signs, collection of blood and tissue samples, quantification of viral load, and evaluation of humoral, innate, and cell-mediated immune responses in growing pigs can be performed as described above.

Clinical Monitoring, Blood, and Tissue Sampling of Pregnant Sows

Pregnant sows can be monitored daily for clinical signs and blood samples will be collected at gestation day 60 (dpv 0), 88, and on the day of euthanasia. Sows and neonates can be euthanized and the samples collected as described earlier (173). Briefly, between 109 and 112 days of gestation, sows can be euthanized and the uterine horns can be immediately necropsied and number of live and stillborn fetuses can be recorded. Blood samples can be collected from each fetus and plasma can be aliquoted and stored at −70° C. Both maternal and fetal tissues (TBLN, tonsil, and lung) can be collected and stored in formalin for histological studies, and also similar tissue samples collected in RNA later (Ambion) can be analyzed for PRRSV RNA and cytokine mRNA by qRT-PCR.

Statistical Analyses

Data analyses can be carried out using SAS. Comparisons of viral load, cytokine levels, and VN titers can be performed by analysis of variance (ANOVA), with Duncan's multiple comparison tests used when the ANOVA test indicates significant difference. Comparisons of antibody response can be made using the Kruskal-Wallis non-parametric test.

REFERENCES

1. Okada, H., and H. Toguchi. 1995. Biodegradable microspheres in drug delivery. *Crit Rev Ther Drug Carrier Syst* 12:1-99.
2. Aguado, M. T., and P. H. Lambert. 1992. Controlled-release vaccines—biodegradable polylactide/polyglycolide (PL/PG) microspheres as antigen vehicles. *Immunobiology* 184:113-125.
3. T G, P. 1994. Degradation of poly(D,L-lactic acid) microspheres effect of molecular weight. *J Control Release* 30:161-173.
4. Hein, W. R., and P. J. Griebel. 2003. A road less travelled: large animal models in immunological research. *Nat Rev Immunol* 3:79-84.
5. Cozzi, E., A. W. Tucker, G. A. Langford, G. Pino-Chavez, L. Wright, M. J. O'Connell, V. J. Young, R. Lancaster, M. McLaughlin, K. Hunt, M. C. Bordin, and D. J. White. 1997. Characterization of pigs transgenic for human decay-accelerating factor. *Transplantation* 64:1383-1392.
6. Ibrahim, Z., J. Busch, M. Awwad, R. Wagner, K. Wells, and D. K. Cooper. 2006. Selected physiologic compatibilities and incompatibilities between human and porcine organ systems. *Xenotransplantation* 13:488-499.
7. Rogers, C. S., W. M. Abraham, K. A. Brogden, J. F. Engelhardt, J. T. Fisher, P. B. McCray, Jr., G. McLennan, D. K. Meyerholz, E. Namati, L. S. Ostedgaard, R. S. Prather, J. R. Sabater, D. A. Stoltz, J. Zabner, and M. J. Welsh. 2008. The porcine lung as a potential model for cystic fibrosis. *Am J Physiol Lung Cell Mol Physiol* 295:L240-263.
8. Holtkamp, D., and J. Kliebenstein. 2011. PRRS Costs Industry $664 Million Annually. Pork Checkoff Study.
9. Cavanagh, D. 1997. Nidovirales: a new order comprising Coronaviridae and Arteriviridae. *Arch Virol* 142:629-633.
10. Meulenberg, J. J. 2000. PRRSV, the virus. *Vet Res* 31:11-21.
11. Done, S. H., and D. J. Paton. 1995. Porcine reproductive and respiratory syndrome: clinical disease, pathology and immunosuppression. *Vet Rec* 136:32-35.
12. Renukaradhya, G. J., K. Alekseev, K. Jung, Y. Fang, and L. J. Saif. 2010. Porcine reproductive and respiratory syndrome virus-induced immunosuppression exacerbates the inflammatory response to porcine respiratory coronavirus in pigs. *Viral Immunol* 23:457-466.
13. Halbur, P. G., L. D. Miller, P. S. Paul, X. J. Meng, E. L. Huffman, and J. J. Andrews. 1995. Immunohistochemical identification of porcine reproductive and respiratory syndrome virus (PRRSV) antigen in the heart and lymphoid system of three-week-old colostrum-deprived pigs. *Vet Pathol* 32:200-204.
14. Mateu, E., and I. Diaz. 2008. The challenge of PRRS immunology. *Vet J* 177:345-351.
15. Murtaugh, M. P., Z. Xiao, and F. Zuckermann. 2002. Immunological responses of swine to porcine reproductive and respiratory syndrome virus infection. *Viral Immunol* 15:533-547.
16. Dwivedi, V., C. Manickam, B. Binjawadagi, D. Linhares, M. P. Murtaugh, and G. J. Renukaradhya. 2012. Evaluation of immune responses to porcine reproductive and respiratory syndrome virus in pigs during early stage of infection under farm conditions. *Virol J* 9:45.
17. Holmgren, J., C. Czerkinsky, N. Lycke, and A. M. Svennerholm. 1992. Mucosal immunity: implications for vaccine development. *Immunobiology* 184:157-179.
18. Sedgmen, B. J., E. N. Meeusen, and S. A. Lofthouse. 2004. Alternative routes of mucosal immunization in large animals. *Immunol Cell Biol* 82:10-16.
19. McGhee, J. R., J. Mestecky, M. T. Dertzbaugh, J. H. Eldridge, M. Hirasawa, and H. Kiyono. 1992. The mucosal immune system: from fundamental concepts to vaccine development. *Vaccine* 10:75-88.
20. Rudin, A., G. C. Riise, and J. Holmgren. 1999. Antibody responses in the lower respiratory tract and male urogenital tract in humans after nasal and oral vaccination with cholera toxin B subunit. *Infect Immun* 67:2884-2890.
21. Ogra, P. L., and D. T. Karzon. 1969. Distribution of poliovirus antibody in serum, nasopharynx and alimentary tract following segmental immunization of lower alimentary tract with poliovaccine. *J Immunol* 102:1423-1430.
22. Mestecky, J., S. M. Michalek, Z. Moldoveanu, and M. W. Russell. 1997. Routes of immunization and antigen delivery systems for optimal mucosal immune responses in humans. *Behring Inst Mitt:*33-43.
23. Ryan, E. J., L. M. Daly, and K. H. Mills. 2001. Immunomodulators and delivery systems for vaccination by mucosal routes. *Trends Biotechnol* 19:293-304.
24. Thomas, C., A. Rawat, L. Hope-Weeks, and F. Ahsan. 2011. Aerosolized PLA and PLGA Nanoparticles Enhance Humoral, Mucosal and Cytokine Responses to Hepatitis B Vaccine. *Mol Pharm* 8:405-415.
25. Singh, M., M. Briones, and D. T. O'Hagan. 2001. A novel bioadhesive intranasal delivery system for inactivated influenza vaccines. *J Control Release* 70:267-276.
26. Baras, B., M. A. Benoit, L. Dupre, O. Poulain-Godefroy, A. M. Schacht, A. Capron, J. Gillard, and G. Riveau. 1999. Single-dose mucosal immunization with biodegradable microparticles containing a *Schistosoma mansoni* antigen. *Infect Immun* 67:2643-2648.
27. Mengeling, W. L., K. M. Lager, A. C. Vorwald, and K. J. Koehler. 2003. Strain specificity of the immune response of pigs following vaccination with various strains of porcine reproductive and respiratory syndrome virus. *Vet Microbiol* 93:13-24.
28. Renukaradhya, G. J., V. Dwivedi, C. Manickama, B. Binjawadagia, and D. Benfield. 2012. Mucosal vaccines to prevent porcine reproductive and respiratory syndrome: a new perspective. *Animal Health Research Review* 13:1-17 doi:10.1017/S1466252312000023.
29. Leroith, T., S. Hammond, S. M. Todd, Y. Ni, T. Cecere, and K. D. Pelzer. 2011. A modified live PRRSV vaccine and the pathogenic parent strain induce regulatory T cells in pigs naturally infected with *Mycoplasma hyopneumoniae*. *Vet Immunol Immunopathol* 140:312-316.
30. Thacker, E. L., B. J. Thacker, T. F. Young, and P. G. Halbur. 2000. Effect of vaccination on the potentiation of porcine reproductive and respiratory syndrome virus (PRRSV)-induced pneumonia by *Mycoplasma Hyopneumoniae*. Vaccine 18:1244-1252.
31. Li, B., L. Fang, Z. Xu, S. Liu, J. Gao, Y. Jiang, H. Chen, and S. Xiao. 2009. Recombination in vaccine and circulating strains of porcine reproductive and respiratory syndrome viruses. *Emerg Infect Dis* 15:2032-2035.
32. Nielsen, H. S., M. B. Oleksiewicz, R. Forsberg, T. Stadejek, A. Botner, and T. Storgaard. 2001. Reversion of a live porcine reproductive and respiratory syndrome virus vaccine investigated by parallel mutations. *J Gen Virol* 82:1263-1272.
33. Storgaard, T., M. Oleksiewicz, and A. Bother. 1999. Examination of the selective pressures on a live PRRS vaccine virus. *Arch Virol* 144:2389-2401.
34. Wesley, R. D., W. L. Mengeling, K. M. Lager, A. C. Vorwald, and M. B. Roof 1999. Evidence for divergence of restriction fragment length polymorphism patterns following in vivo replication of porcine reproductive and respiratory syndrome virus. *Am J Vet Res* 60:463-467.
35. Bassaganya-Riera, J., B. J. Thacker, S. Yu, E. Strait, M. J. Wannemuehler, and E. L. Thacker. 2004. Impact of immunizations with porcine reproductive and respiratory syndrome virus on lymphoproliferative recall responses of CD8+ T cells. *Viral Immunol* 17:25-37.
36. Piras, F., S. Bollard, F. Laval, F. Joisel, G. Reynaud, C. Charreyre, C. Andreoni, and V. Juillard. 2005. Porcine reproductive and respiratory syndrome (PRRS) virus-specific interferon-gamma(+) T-cell responses after PRRS virus infection or vaccination with an inactivated PRRS vaccine. *Viral Immunol* 18:381-389.
37. Christopher-Hennings, J., L. D. Holler, D. A. Benfield, and E. A. Nelson. 2001. Detection and duration of porcine reproductive and respiratory syndrome virus in semen, serum, peripheral blood mononuclear cells, and tissues from Yorkshire, Hampshire, and Landrace boars. *J Vet Diagn Invest* 13:133-142.
38. Kim, W. I., D. S. Lee, W. Johnson, M. Roof, S. H. Cha, and K. J. Yoon. 2007. Effect of genotypic and biotypic differences among PRRS viruses on the serologic assessment of pigs for virus infection. *Vet Microbiol* 123:1-14.

39. A. Piotrowicz, M. S. S. 2005. Incorporation of microspheres into nerve guidance channels for drug delivery purposes. *Applied Chemistry and Chemical Enginnering*, University of Toronto, Toronto: p. 108.
40. Cao, X., and M. S. Schoichet. 1999. Delivering neuroactive molecules from biodegradable microspheres for application in central nervous system disorders. *Biomaterials* 20:329-339.
41. Rajapaksa, T. E., K. M. Bennett, M. Hamer, C. Lytle, V. G. Rodgers, and D. D. Lo. 2010. Intranasal M cell uptake of nanoparticles is independently influenced by targeting ligands and buffer ionic strength. *J Biol Chem* 285:23739-23746.
42. Khatri, M., V. Dwivedi, S. Krakowka, C. Manickam, A. Ali, L. Wang, Z. Qin, G. J. Renukaradhya, and C. W. Lee. 2010. Swine influenza H1N1 virus induces acute inflammatory immune responses in pig lungs: a potential animal model for human H1N1 influenza virus. *J Virol* 84:11210-11218.
43. Carrasco, C. P., R. C. Rigden, R. Schaffner, H. Gerber, V. Neuhaus, S. Inumaru, H. Takamatsu, G. Bertoni, K. C. McCullough, and A. Summerfield. 2001. Porcine dendritic cells generated in vitro: morphological, phenotypic and functional properties. *Immunology* 104:175-184.
44. Jung, K., K. P. Alekseev, X. Zhang, D. S. Cheon, A. N. Vlasova, and L. J. Saif. 2007. Altered pathogenesis of porcine respiratory coronavirus in pigs due to immunosuppressive effects of dexamethasone: implications for corticosteroid use in treatment of severe acute respiratory syndrome coronavirus. *J Virol* 81:13681-13693.
45. Grumelli, S., D. B. Corry, L. Z. Song, L. Song, L. Green, J. Huh, J. Hacken, R. Espada, R. Bag, D. E. Lewis, and F. Kheradmand. 2004. An immune basis for lung parenchymal destruction in chronic obstructive pulmonary disease and emphysema. *PLoS Med* 1:e8.
46. Barbe, F., K. Atanasova, and K. Van Reeth. 2010. Cytokines and acute phase proteins associated with acute swine influenza infection in pigs. *Vet J* 2010 Jan. 21
47. VanCott, J. L., T. A. Brim, R. A. Simkins, and L. J. Saif. 1993. Isotype-specific antibody-secreting cells to transmissible gastroenteritis virus and porcine respiratory coronavirus in gut- and bronchus-associated lymphoid tissues of suckling pigs. *J Immunol* 150:3990-4000.
48. Dwivedi, V., C. Manickam, R. Patterson, K. Dodson, M. Murtaugh, J. B. Torrelles, L. S. Schlesinger, and G. J. Renukaradhya. 2011. Cross-protective immunity to porcine reproductive and respiratory syndrome virus by intranasal delivery of a live virus vaccine with a potent adjuvant. *Vaccine* 29:4058-4066.
49. Basta, S., C. P. Carrasco, S. M. Knoetig, R. C. Rigden, H. Gerber, A. Summerfield, and K. C. McCullough. 2000. Porcine alveolar macrophages: poor accessory or effective suppressor cells for T-lymphocytes. *Vet Immunol Immunopathol* 77:177-190.
50. Dwivedi, V., A. Vasco, S. Vedi, A. Dangi, K. Arif, S. M. Bhattacharya, and M. Owais. 2009. Adjuvanticity and protective immunity of *Plasmodium yoelii* nigeriensis blood-stage soluble antigens encapsulated in fusogenic liposome. *Vaccine* 27:473-482.
51. Allaoui-Attarki, K., S. Pecquet, E. Fattal, S. Trolle, E. Chachaty, P. Couvreur, and A. Andremont. 1997. Protective immunity against *Salmonella typhimurium* elicited in mice by oral vaccination with phosphorylcholine encapsulated in poly(DL-lactide-co-glycolide) microspheres. *Infect Immun* 65:853-857.
52. Shahin, R., M. Leef, J. Eldridge, M. Hudson, and R. Gilley. 1995. Adjuvanticity and protective immunity elicited by *Bordetella pertussis* antigens encapsulated in poly(DL-lactide-co-glycolide) microspheres. *Infect Immun* 63:1195-1200.
53. Greenway, T. E., J. H. Eldridge, G. Ludwig, J. K. Staas, J. F. Smith, R. M. Gilley, and S. M. Michalek. 1998. Induction of protective immune responses against Venezuelan equine encephalitis (VEE) virus aerosol challenge with microencapsulated VEE virus vaccine. *Vaccine* 16:1314-1323.
54. Shephard, M. J., D. Todd, B. M. Adair, A. L. Po, D. P. Mackie, and E. M. Scott. 2003. Immunogenicity of bovine parainfluenza type 3 virus proteins encapsulated in nanoparticle vaccines, following intranasal administration to mice. *Res Vet Sci* 74:187-190.
55. Thomas, C., V. Gupta, and F. Ahsan. 2009. Influence of surface charge of PLGA particles of recombinant hepatitis B surface antigen in enhancing systemic and mucosal immune responses. *Int J Pharm*.
56. Wills, R. W., J. J. Zimmerman, K. J. Yoon, S. L. Swenson, M. J. McGinley, H. T. Hill, K. B. Platt, J. Christopher-Hennings, and E. A. Nelson. 1997. Porcine reproductive and respiratory syndrome virus: a persistent infection. *Vet Microbiol* 55:231-240.
57. Albina, E., C. Carrat, and B. Charley. 1998. Interferon-alpha response to swine arterivirus (PoAV), the porcine reproductive and respiratory syndrome virus. *J Interferon Cytokine Res* 18:485-490.
58. Brayden, D. J., M. A. Jepson, and A. W. Baird. 2005. Keynote review: intestinal Peyer's patch M cells and oral vaccine targeting. *Drug Discov Today* 10:1145-1157.
59. Inaba, K., M. Inaba, M. Naito, and R. M. Steinman. 1993. Dendritic cell progenitors phagocytose particulates, including *bacillus* Calmette-Guerin organisms, and sensitize mice to mycobacterial antigens in vivo. *J Exp Med* 178:479-488.
60. Gupta, R. K., A. C. Chang, and G. R. Siber. 1998. Biodegradable polymer microspheres as vaccine adjuvants and delivery systems. *Dev Biol Stand* 92:63-78.
61. Heit, A., F. Schmitz, T. Haas, D. H. Busch, and H. Wagner. 2007. Antigen co-encapsulated with adjuvants efficiently drive protective T cell immunity. *Eur J Immunol* 37:2063-2074.
62. Ganter, M., and A. Hensel. 1997. Cellular variables in bronchoalveolar lavage fluids (BALF) in selected healthy pigs. *Res Vet Sci* 63:215-217.
63. Schaumann, F., P. J. Borm, A. Herbrich, J. Knoch, M. Pitz, R. P. Schins, B. Luettig, J. M. Hohlfeld, J. Heinrich, and N. Krug. 2004. Metal-rich ambient particles (particulate matter 2.5) cause airway inflammation in healthy subjects. *Am J Respir Crit Care Med* 170:898-903.
64. Thomassen, M. J., B. P. Barna, A. G. Malur, T. L. Bonfield, C. F. Farver, A. Malur, H. Dalrymple, M. S. Kavuru, and M. Febbraio. 2007. ABCG1 is deficient in alveolar macrophages of GM-CSF knockout mice and patients with pulmonary alveolar proteinosis. *J Lipid Res* 48:2762-2768.
65. Wilkinson, K. A., J. T. Belisle, M. Mincek, R. J. Wilkinson, and Z. Toossi. 2000. Enhancement of the human T cell response to culture filtrate fractions of *Mycobacterium tuberculosis* by microspheres. *J Immunol Methods* 235:1-9.
66. Aiba, S. 1992. Studies on chitosan: 4. Lysozymic hydrolysis of partially N-acetylated chitosans. *Int J Biol Macromol* 14:225-228.

67. Guermonprez, P., J. Valladeau, L. Zitvogel, C. Thery, and S. Amigorena. 2002. Antigen presentation and T cell stimulation by dendritic cells. *Annu Rev Immunol* 20:621-667.
68. van der Lubben, I. M., J. C. Verhoef, G. Borchard, and H. E. Junginger. 2001. Chitosan and its derivatives in mucosal drug and vaccine delivery. *Eur J Pharm Sci* 14:201-207.
69. Shibata, Y., L. A. Foster, W. J. Metzger, and Q. N. Myrvik. 1997. Alveolar macrophage priming by intravenous administration of chitin particles, polymers of N-acetyl-D-glucosamine, in mice. *Infect Immun* 65:1734-1741.
70. Nagao, G., K. Ishii, K. Hirota, K. Makino, and H. Terada. 2011. Role of lipid rafts in innate immunity and phagocytosis of polystyrene latex microspheres. *Colloids Surf B Biointerfaces* 84:317-324.
71. Wong, J. P., L. L. Stadnyk, and E. G. Saravolac. 1994. Enhanced protection against respiratory influenza A infection in mice by liposome-encapsulated antibody. *Immunology* 81:280-284.
72. Miyake, A., T. Akagi, Y. Enose, M. Ueno, M. Kawamura, R. Horiuchi, K. Hiraishi, M. Adachi, T. Serizawa, O. Narayan, M. Akashi, M. Baba, and M. Hayami. 2004. Induction of HIV-specific antibody response and protection against vaginal SHIV transmission by intranasal immunization with inactivated SHIV-capturing nanospheres in macaques. *J Med Virol* 73:368-377.
73. Olin, M. R., L. Batista, Z. Xiao, S. A. Dee, M. P. Murtaugh, C. C. Pijoan, and T. W. Molitor. 2005. Gammadelta lymphocyte response to porcine reproductive and respiratory syndrome virus. *Viral Immunol* 18:490-499.
74. Welsh, R. M., M. Y. Lin, B. L. Lohman, S. M. Varga, C. C. Zarozinski, and L. K. Selin. 1997. Alpha beta and gamma delta T-cell networks and their roles in natural resistance to viral infections. *Immunol Rev* 159:79-93.
75. Didierlaurent, A., J. Goulding, and T. Hussell. 2007. The impact of successive infections on the lung microenvironment. *Immunology* 122:457-465.
76. Waters, W. R., R. E. Sacco, A. D. Dorn, R. Hontecillas, F. A. Zuckermann, and M. J. Wannemuehler. 1999. Systemic and mucosal immune responses of pigs to parenteral immunization with a pepsin-digested *Serpulina hyodysenteriae* bacterin. *Vet Immunol Immunopathol* 69:75-87.
77. Suradhat, S., R. Thanawongnuwech, and Y. Poovorawan. 2003. Upregulation of IL-10 gene expression in porcine peripheral blood mononuclear cells by porcine reproductive and respiratory syndrome virus. *J Gen Virol* 84:453-459.
78. Charerntantanakul, W., R. Platt, and J. A. Roth. 2006. Effects of porcine reproductive and respiratory syndrome virus-infected antigen-presenting cells on T cell activation and antiviral cytokine production. *Viral Immunol* 19:646-661.
79. Carpenter, Z. K., E. D. Williamson, and J. E. Eyles. 2005. Mucosal delivery of microparticle encapsulated ESAT-6 induces robust cell-mediated responses in the lung milieu. *J Control Release* 104:67-77.
80. Lamm, M. E. 1976. Cellular aspects of immunoglobulin A. *Adv Immunol* 22:223-290.
81. Mestecky, J., and J. R. McGhee. 1987. Immunoglobulin A (IgA): molecular and cellular interactions involved in IgA biosynthesis and immune response. *Adv Immunol* 40:153-245.
82. Liew, F. Y., S. M. Russell, G. Appleyard, C. M. Brand, and J. Beale. 1984. Cross-protection in mice infected with influenza A virus by the respiratory route is correlated with local IgA antibody rather than serum antibody or cytotoxic T cell reactivity. *Eur J Immunol* 14:350-356.
83. Lizeng, Q., C. Nilsson, S. Sourial, S. Andersson, O. Larsen, P. Aaby, M. Ehnlund, and E. Bjorling. 2004. Potent neutralizing serum immunoglobulin A (IgA) in human immunodeficiency virus type 2-exposed IgG-seronegative individuals. *J Virol* 78:7016-7022.
84. Renegar, K. B., and P. A. Small, Jr. 1991. Immunoglobulin A mediation of murine nasal anti-influenza virus immunity. *J Virol* 65:2146-2148.
85. Renegar, K. B., and P. A. Small, Jr. 1991. Passive transfer of local immunity to influenza virus infection by IgA antibody. *J Immunol* 146:1972-1978.
86. Diaz I, Darwich L, Pappaterra G, Pujols J, Mateu E. Immune responses of pigs after experimental infection with a European strain of Porcine reproductive and respiratory syndrome virus. *J Gen Virol* 2005 July; 86(Pt 7):1943-51.
87. Mengeling W L, Clouser D F, Vorwald A C, Lager K M. The potential role of genetic recombination in the evolution of new strains of porcine reproductive and respiratory syndrome virus (PRRSV). *J Swine Health Prod* 2002; 10:273-5.
88. Li B, Fang L, Xu Z, Liu S, Gao J, Jiang Y, et al. Recombination in vaccine and circulating strains of porcine reproductive and respiratory syndrome viruses. *Emerg Infect Dis* 2009 December; 15(12):2032-5.
89. Charerntantanakul W. Adjuvants for porcine reproductive and respiratory syndrome virus vaccines. *Vet Immunol Immunopathol* 2009 May 15; 129(1-2):1-13.
90. Duncan R. Nanomedicine gets clinical. *Materials Today* 2005; 8:16-7.
91. Eldridge J H, Gilley R M, Staas J K, Moldoveanu Z, Meulbroek J A, Tice T R. Biodegradable microspheres: vaccine delivery system for oral immunization. *Curr Top Microbiol Immunol* 1989; 146:59-66.
92. McNeil S E. Nanotechnology for the biologist. *J Leukoc Biol* 2005 September; 78(3):585-94.
93. Cao X, Schoichet M S. Delivering neuroactive molecules from biodegradable microspheres for application in central nervous system disorders. *Biomaterials* 1999 February; 20(4):329-39.
94. VanCott J L, Brim T A, Simkins R A, Saif L J. Isotype-specific antibody-secreting cells to transmissible gastroenteritis virus and porcine respiratory coronavirus in gut- and bronchus-associated lymphoid tissues of suckling pigs. *J Immunol* 1993 May 1; 150(9):3990-4000.
95. Dwivedi V, Manickam C, Patterson R, Dodson K, Weeman M, Renukaradhya G J. Intranasal delivery of whole cell lysate of *Mycobacterium tuberculosis* induces protective immune responses to a modified live porcine reproductive and respiratory syndrome virus vaccine in pigs. *Vaccine* 2011 May 23; 29(23):4067-76.
96. Madsen K G, Hansen C M, Madsen E S, Strandbygaard B, Botner A, Sorensen K J. Sequence analysis of porcine reproductive and respiratory syndrome virus of the American type collected from Danish swine herds. *Arch Virol* 1998; 143(9):1683-700.
97. Nielsen J, Botner A, Bille-Hansen V, Oleksiewicz M B, Storgaard T. Experimental inoculation of late term pregnant sows with a field isolate of porcine reproductive and respiratory syndrome vaccine-derived virus. *Vet Microbiol* 2002 Jan. 3; 84(1-2):1-13.
98. Osorio F A, Galeota J A, Nelson E, Brodersen B, Doster A, Wills R, et al. Passive transfer of virus-specific antibodies confers protection against reproductive failure 99. Labarque G G, Nauwynck H J, Van Reeth K, Pensaert M B. Effect of cellular changes and onset of humoral immunity on the replication of porcine reproductive and respiratory syndrome virus in the lungs of pigs. J Gen Virol 2000 May; 81(Pt 5):1327-34.

100. Vanhee M, Delputte P L, Delrue I, Geldhof M F, Nauwynck H J. Development of an experimental inactivated PRRSV vaccine that induces virus-neutralizing antibodies. Vet Res 2009 November-December; 40(6):63.

101. Thomas C, Gupta V, Ahsan F. Influence of surface charge of PLGA particles of recombinant hepatitis B surface antigen in enhancing systemic and mucosal immune responses. Int J Pharm 2009 Jun. 12.

102. Nayak B, Panda A K, Ray P, Ray A R. Formulation, characterization and evaluation of rotavirus encapsulated PLA and PLGA particles for oral vaccination. J Microencapsul 2009 March; 26(2):154-65.

103. Liew F Y, Russell S M, Appleyard G, Brand C M, Beale J. Cross-protection in mice infected with influenza A virus by the respiratory route is correlated with local IgA antibody rather than serum antibody or cytotoxic T cell reactivity. Eur J Immunol 1984 April; 14(4):350-6.

104. Xiao Z, Batista L, Dee S, Halbur P, Murtaugh M P. The level of virus-specific T-cell and macrophage recruitment in porcine reproductive and respiratory syndrome virus infection in pigs is independent of virus load. J Virol 2004 June; 78(11):5923-33.

105. Wang G, Song T, Yu Y, Liu Y, Shi W, Wang S, et al. Immune responses in piglets infected with highly pathogenic porcine reproductive and respiratory syndrome virus. Vet Immunol Immunopathol Aug. 15; 142(3-4): 170-8.

106. Zuckermann F A. Extrathymic CD4/CD8 double positive T cells. Vet Immunol Immunopathol 1999 Dec. 15; 72(1-2):55-66.

107. Gomez-Laguna J, Salguero F J, De Marco M F, Pallares F J, Bernabe A, Carrasco L. Changes in lymphocyte subsets and cytokines during European porcine reproductive and respiratory syndrome: increased expression of IL-12 and IL-10 and proliferation of CD4(−)CD8(high). Viral Immunol 2009 July; 22(4):261-71.

108. Kaplan M H, Sun Y L, Hoey T, Grusby M J. Impaired IL-12 responses and enhanced development of Th2 cells in Stat4-deficient mice. Nature 1996 Jul. 11; 382(6587): 174-7.

109. Waters W R, Sacco R E, Dorn A D, Hontecillas R, Zuckermann F A, Wannemuehler M J. Systemic and mucosal immune responses of pigs to parenteral immunization with a pepsin-digested *Serpulina hyodysenteriae* bacterin. Vet Immunol Immunopathol 1999 Jul. 1; 69(1): 75-87.

110. Wongyanin P, Buranapraditkun S, Chokeshai-Usaha K, Thanawonguwech R, Suradhat S. Induction of inducible CD4+CD25+Foxp3+ regulatory T lymphocytes by porcine reproductive and respiratory syndrome virus (PRRSV). Vet Immunol Immunopathol 2010 Feb. 15; 133(2-4):170-82.

111. Olin M R, Hwa Choi K, Lee J, Molitor T W. Gammadelta T-lymphocyte cytotoxic activity against *Mycobacterium bovis* analyzed by flow cytometry. J Immunol Methods 2005 February; 297(1-2):1-11.

112. Lederer, E., A. Adam, R. Ciorbaru, J. F. Petit, and J. Wietzerbin. 1975. Cell walls of Mycobacteria and related organisms; chemistry and immunostimulant properties. Mol Cell Biochem 7:87-104.

113. Adam, A., R. Ciorbaru, J. F. Petit, and E. Lederer. 1972. Isolation and properties of a macromolecular, water-soluble, immuno-adjuvant fraction from the cell wall of *Mycobacterium smegmatis*. Proc Natl Acad Sci USA 69:851-854.

114. Adam, A., R. Ciorbaru, J. F. Petit, E. Lederer, L. Chedid, A. Lamensans, F. Parant, M. Parant, J. P. Rosselet, and F. M. Berger. 1973. Preparation and biological properties of water-soluble adjuvant fractions from delipidated cells of *Mycobacterium smegmatis* and *Nocardia opaca*. Infect Immun 7:855-861.

115. Nateghi Rostami, M., H. Keshavarz, and A. Khamesipour. 2010. Immune response of BALB/c mice against an experimental vaccine of Alum precipitated autoclaved *Leishmania major* (Alum-ALM) mixed with BCG or *Mycobacterium vaccae*. Trop Biomed 27:89-102.

116. Hernandez-Pando, R., D. Aguilar, H. Orozco, Y. Cortez, L. R. Brunet, and G. A. Rook. 2008. Orally administered *Mycobacterium vaccae* modulates expression of immunoregulatory molecules in BALB/c mice with pulmonary tuberculosis. Clin Vaccine Immunol 15:1730-1736

117. Kimman T G, Cornelissen L A, Moormann R J, Rebel J M, Stockhofe-Zurwieden N. Challenges for porcine reproductive and respiratory syndrome virus (PRRSV) vaccinology. Vaccine 2009 Jun. 8; 27(28):3704-18.

118. Rossow K D, Benfield D A, Goyal S M, Nelson E A, Christopher-Hennings J, Collins J E. Chronological immunohistochemical detection and localization of porcine reproductive and respiratory syndrome virus in gnotobiotic pigs. Vet Pathol 1996 September; 33(5):551-6.

119. Lycke N. Recent progress in mucosal vaccine development: potential and limitations. Nat Rev Immunol 2012; 12(8):592-605.

120. Heegaard P M, Dedieu L, Johnson N, Le Potier M F, Mockey M, Mutinelli F, et al. Adjuvants and delivery systems in veterinary vaccinology: current state and future developments. Arch Virol 2011 February; 156(2): 183-202.

121. O'Hagan D T, Rahman D, McGee J P, Jeffery H, Davies M C, Williams P, et al. Biodegradable microparticles as controlled release antigen delivery systems. Immunology 1991 June; 73(2):239-42.

122. Chadwick S, Kriegel C, Amiji M. Nanotechnology solutions for mucosal immunization. Adv Drug Deliv Rev 2010 Mar. 18; 62(4-5):394-407.

123. Dwivedi V, Manickam C, Binjawadagi B, Joyappa D, Renukaradhya G J. Biodegradable Nanoparticle-Entrapped Vaccine Induces Cross-Protective Immune Response against a Virulent Heterologous Respiratory Viral Infection in Pigs. PLoS One 2012; 7(12):e51794.

124. Saini V, Jain V, Sudheesh M S, Jaganathan K S, Murthy P K, Kohli D V. Comparison of humoral and cell-mediated immune responses to cationic PLGA microspheres containing recombinant hepatitis B antigen. Int J Pharm 2011 Apr. 15; 408(1-2):50-7.

125. Zimmerman J J, Benfield D, Dee S, Murtaugh M, Stadejek T, Stevenson G W, et al. Porcine reproductive and respiratory syndrome virus (Porcine Arterivirus). Diseases of Swine, Tenth Edition Published by John Wiley & Sons, Inc 2012.

126. Cai H Y, Alexander H, Carman S, Lloyd D, Josephson G, Maxie M G. Restriction fragment length polymorphism of porcine reproductive and respiratory syndrome viruses recovered from Ontario farms, 1998-2000. J Vet Diagn Invest 2002 July; 14(4):343-7.

127. Fang Y, Kim D Y, Ropp S, Steen P, Christopher-Hennings J, Nelson E A, et al. Heterogeneity in Nsp2 of European-like porcine reproductive and respiratory syndrome viruses isolated in the United States. Virus Res 2004 Mar. 15; 100(2):229-35.

128. Manickam C, Dwivedi V, Patterson R, Papenfuss T, Renukaradhya G J. Porcine reproductive and respiratory syndrome virus induces pronounced immune modulatory responses at mucosal tissues in the parental vaccine strain VR2332 infected pigs. Vet Microbiol 2012.

129. Ito F, Fujimori H, Makino K. Factors affecting the loading efficiency of water-soluble drugs in PLGA microspheres. Colloids Surf B Biointerfaces 2008 Jan. 15; 61(1):25-9.

130. Rawat A, Majumder Q H, Ahsan F Inhalable large porous microspheres of low molecular weight heparin: in vitro and in vivo evaluation. J Control Release 2008 Jun. 24; 128(3):224-32.

131. Lopez O J, Osorio F A. Role of neutralizing antibodies in PRRSV protective immunity. Vet Immunol Immunopathol 2004 Dec. 8; 102(3):155-63.

132. Yoshida M, Babensee J E. Differential effects of agarose and poly(lactic-co-glycolic acid) on dendritic cell maturation. J Biomed Mater Res A 2006 November; 79(2):393-408.

133. Nixon D F, Hioe C, Chen P D, Bian Z, Kuebler P, Li M L, et al. Synthetic peptides entrapped in microparticles can elicit cytotoxic T cell activity. Vaccine 1996 November; 14(16):1523-30.

134. Mukherjee B, Santra K, Pattnaik G, Ghosh S. Preparation, characterization and in-vitro evaluation of sustained release protein-loaded nanoparticles based on biodegradable polymers. Int J Nanomedicine 2008; 3(4):487-96.

135. Moghimi S M, Szebeni J. Stealth liposomes and long circulating nanoparticles: critical issues in pharmacokinetics, opsonization and protein-binding properties. Prog Lipid Res 2003 November; 42(6):463-78.

136. Kim B, Bowersock T, Griebel P, Kidane A, Babiuk L A, Sanchez M, et al. Mucosal immune responses following oral immunization with rotavirus antigens encapsulated in alginate microspheres. J Control Release 2002 Dec. 13; 85(1-3):191-202.

137. Gupta P N, Mahor S, Rawat A, Khatri K, Goyal A, Vyas S P. Lectin anchored stabilized biodegradable nanoparticles for oral immunization 1. Development and in vitro evaluation. Int J Pharm 2006 Aug. 2; 318(1-2):163-73.

138. Manocha M, Pal P C, Chitralekha K T, Thomas B E, Tripathi V, Gupta S D, et al. Enhanced mucosal and systemic immune response with intranasal immunization of mice with HIV peptides entrapped in PLG microparticles in combination w 465 ith *Ulex Europaeus*-I lectin as M cell target. Vaccine 2005 Dec. 1; 23(48-49):5599-617.

139. Kugathasan K, Roediger E K, Small C L, McCormick S, Yang P, Xing Z. CD11c+ antigen presenting cells from the alveolar space, lung parenchyma and spleen differ in their phenotype and capabilities to activate naive and antigen-primed T cells. BMC Immunol 2008; 9:48.

140. Thompson A L, Johnson B T, Sempowski G D, Gunn M D, Hou B, DeFranco A L, et al. Maximal adjuvant activity of nasally delivered IL-1alpha requires adjuvant-responsive CD11c(+) cells and does not correlate with adjuvant-induced in vivo cytokine production. J Immunol 2012 Mar. 15; 188(6):2834-46.

141. Amorij J P, Kersten G F, Saluja V, Tonnis W F, Hinrichs W L, Slutter B, et al. Towards tailored vaccine delivery: Needs, challenges and perspectives. J Control Release 2012 Jul. 20; 161(2):363-76.

142. Spellberg B, Edwards J E, Jr. Type 1/Type 2 immunity in infectious diseases. Clin Infect Dis 2001 January; 32(1):76-102.

143. Manickam C, Dwivedi V, Patterson R, Papenfuss T, Renukaradhya G J. Porcine reproductive and respiratory syndrome virus induces pronounced immune modulatory responses at mucosal tissues in the parental vaccine strain VR2332 infected pigs. Vet Microbiol, doi:pii:S0378-1135 (12)00486-5 101016/jvetmic201208021 2012 Sep. 1.

144. Schliehe C, Redaelli C, Engelhardt S, Fehlings M, Mueller M, van Rooijen N, et al. CD8-dendritic cells and macrophages cross-present poly(D,L-lactate-co-glycolate) acid microsphere encapsulated antigen in vivo. J Immunol 2011 Sep. 1; 187(5):2112-21.

145. Arifuzzaman M, Rashu R, Leung D T, Hosen M I, Bhuiyan T R, Bhuiyan M S, et al. Antigen-specific memory T cell responses after vaccination with an oral killed cholera vaccine in Bangladeshi children and comparison to responses in patients with naturally acquired cholera. Clin Vaccine Immunol 2012 August; 19(8):1304-11.

146. Chong C S, Cao M, Wong W W, Fischer K P, Addison W R, Kwon G S, et al. Enhancement of T helper type 1 immune responses against hepatitis B virus core antigen by PLGA nanoparticle vaccine delivery. J Control Release 2005 Jan. 20; 102(1):85-99.

147. Ma W, Chen M, Kaushal S, McElroy M, Zhang Y, Ozkan C, et al. PLGA nanoparticle mediated delivery of tumor antigenic peptides elicits effective immune responses. Int J Nanomedicine 2012; 7:1475-87.

148. Zhang L, Tian X, Zhou F. Intranasal administration of CpG oligonucleotides induces mucosal and systemic Type 1 immune responses and adjuvant activity to porcine reproductive and respiratory syndrome killed virus vaccine in piglets in vivo. Int Immunopharmacol 2007 Dec. 15; 7(13):1732-40.

149. Guo Y J, Sun S H, Zhang Y, Chen Z H, Wang K Y, Huang L, et al. Protection of pigs against *Taenia solium* cysticercosis using recombinant antigen or in combination with DNA vaccine. Vaccine 2004 Sep. 28; 22(29-30):3841-7.

150. Azevedo M S, Yuan L, Pouly S, Gonzales A M, Jeong K I, Nguyen T V, et al. Cytokine responses in gnotobiotic pigs after infection with virulent or attenuated human rotavirus. J Virol 2006 January; 80(1):372-82.

151. Thompson A L, Johnson B T, Sempowski G D, Gunn M D, Hou B, DeFranco A L, et al. Maximal adjuvant activity of nasally delivered IL-1alpha requires adjuvant-responsive CD11c(+) cells and does not correlate with adjuvant-induced in vivo cytokine production. J Immunol 2012 Mar. 15; 188(6):2834-46.

152 Nobs, L., F. Buchegger, R. Gurny, and E. Allemann. 2004. Current methods for attaching targeting ligands to liposomes and nanoparticles. *J Pharm Sci* 93:1980-1992.

153. Maruyama, A., T. Ishihara, J. S. Kim, S. W. Kim, and T. Akaike. 1997. Nanoparticle DNA carrier with poly(L-lysine) grafted polysaccharide copolymer and poly(D,L-lactic acid). *Bioconjug Chem* 8:735-742

154 Ilium, L., and S. N. Chatfield. 2001. Vaccine compositions including chitosan for intranasal administration and use thereof. U.S. Pat. No. 6,391,318.

155. Janes, K. A., M. P. Fresneau, A. Marazuela, A. Fabra, and M. J. Alonso. 2001. Chitosan nanoparticles as delivery systems for doxorubicin. *J Control Release* 73:255-267.

156. Singla, A. K., and M. Chawla. 2001. Chitosan: some pharmaceutical and biological aspects—an update. *J Pharm Pharmacol* 53:1047-1067.

157. van der Lubben, I. M., J. C. Verhoef, G. Borchard, and H. E. Junginger. 2001. Chitosan for mucosal vaccination. *Adv Drug Deliv Rev* 52:139-144.

158. Vila, A., A. Sanchez, K. Janes, I. Behrens, T. Kissel, J. L. Vila Jato, and M. J. Alonso. 2004. Low molecular weight chitosan nanoparticles as new carriers for nasal vaccine delivery in mice. *Eur J Pharm Biopharm* 57:123-131

159. Jung, K., G. J. Renukaradhya, K. P. Alekseev, Y. Fang, Y. Tang, and L. J. Saif. 2009. Porcine 159. reproductive and respiratory syndrome virus modifies innate immunity and alters disease outcome in pigs subsequently infected with porcine respiratory coronavirus: implications for respiratory viral co-infections. *J Gen Virol* 90:2713-2723

160. Kuroki, H., T. Morisaki, K. Matsumoto, H. Onishi, E. Baba, M. Tanaka, and M. Katano. 2003. Streptococcal preparation OK-432: a new maturation factor of monocyte-derived dendritic cells for clinical use. *Cancer Immunol Immunother* 52:561-568

161. VanCott, J. L., T. A. Brim, R. A. Simkins, and L. J. Saif. 1993. Isotype-specific antibody-secreting cells to transmissible gastroenteritis virus and porcine respiratory coronavirus in gut- and bronchus-associated lymphoid tissues of suckling pigs. *J Immunol* 150:3990-4000.

162. Loving, C. L., S. L. Brockmeier, and R. E. Sacco. 2007. Differential type I interferon activation and susceptibility of dendritic cell populations to porcine arterivirus. *Immunology* 120:217-229

163. Wasilk, A., J. D. Callahan, J. Christopher-Hennings, T. A. Gay, Y. Fang, M. Dammen, M. E. Reos, M. Torremorell, D. Polson, M. Mellencamp, E. Nelson, and W. M. Nelson. 2004. Detection of U.S., Lelystad, and European-like porcine reproductive and respiratory syndrome viruses and relative quantitation in boar semen and serum samples by real-time PCR. *J Clin Microbiol* 42:4453-4461

164. Benfield, D. A., E. Nelson, J. E. Collins, L. Harris, S. M. Goyal, D. Robison, W. T. Christianson, R. B. Morrison, D. Gorcyca, and D. Chladek. 1992. Characterization of swine infertility and respiratory syndrome (SIRS) virus (isolate ATCC VR-2332). *J Vet Diagn Invest* 4:127-133

165. Thanawongnuwech, R., T. F. Young, B. J. Thacker, and E. L. Thacker. 2001. Differential production of proinflammatory cytokines: in vitro PRRSV and *Mycoplasma* hyopneumoniae co-infection model. *Vet Immunol Immunopathol* 79:115-127

166. Thompson, A. L., B. T. Johnson, G. D. Sempowski, M. D. Gunn, B. Hou, A. L. DeFranco, and H. F. Staats. 2012. Maximal adjuvant activity of nasally delivered IL-1alpha requires adjuvant-responsive CD11c(+) cells and does not correlate with adjuvant-induced in vivo cytokine production. *J Immunol* 188:2834-2846

167. Ferreira, M. U., and A. M. Katzin. 1995. The assessment of antibody affinity distribution by thiocyanate elution: a simple dose-response approach. *J Immunol Methods* 187:297-305

168. Takayama, K., H. K. Schnoes, E. L. Armstrong, and R. W. Boyle. 1975. Site of inhibitory action of isoniazid in the synthesis of mycolic acids in *Mycobacterium tuberculosis*. *J Lipid Res* 16:308-317

169. Cai, H. Y., H. Alexander, S. Carman, D. Lloyd, G. Josephson, and M. G. Maxie. 2002. Restriction fragment length polymorphism of porcine reproductive and respiratory syndrome viruses recovered from Ontario farms, 1998-2000. *J Vet Diagn Invest* 14:343-347

170. Fang, Y., R. R. Rowland, M. Roof, J. K. Lunney, J. Christopher-Hennings, and E. A. Nelson. 2006. A full-length cDNA infectious clone of North American type 1 porcine reproductive and respiratory syndrome virus: expression of green fluorescent protein in the Nsp2 region. *J Virol* 80:11447-11455

171. Fang, Y., J. Christopher-Hennings, E. Brown, H. Liu, Z. Chen, S. R. Lawson, R. Breen, T. Clement, X. Gao, J. Bao, D. Knudsen, R. Daly, and E. Nelson. 2008. Development of genetic markers in the non-structural protein 2 region of a US type 1 porcine reproductive and respiratory syndrome virus: implications for future recombinant marker vaccine development. *J Gen Virol* 89:3086-3096

172. Collins, J. E., D. A. Benfield, W. T. Christianson, L. Harris, J. C. Hennings, D. P. Shaw, S. M. Goyal, S. McCullough, R. B. Morrison, H. S. Joo, and et al. 1992. Isolation of swine infertility and respiratory syndrome virus (isolate ATCC VR-2332) in North America and experimental reproduction of the disease in gnotobiotic pigs. *J Vet Diagn Invest* 4:117-126.

173. Rowland, R. R. 2010. The interaction between PRRSV and the late gestation pig fetus. *Virus Res* 154:114-122.

174. Albina E. Epidemiology of porcine reproductive and respiratory syndrome (PRRS): an overview. Vet Microbiol 1997 April; 55(1-4):309-16.

175. Rossow K D, Bautista E M, Goyal S M, Molitor T W, Murtaugh M P, Morrison R B, et al. Experimental porcine reproductive and respiratory syndrome virus infection in one-, four-, and 10-week-old pigs. J Vet Diagn Invest 1994 January; 6(1):3-12.

176. Zimmerman J. PRRS Virus—What Happens After a Pig Becomes Infected with PRRS Virus? 2003 PRRS Compendium Producer Edition 2003; Chapter V (National Pork Board, Des Moines, Iowa):36-43.

177. Wagstrom E A, Chang C C, Yoon K J, Zimmerman J J. Shedding of porcine reproductive and respiratory syndrome virus in mammary gland secretions of sows. Am J Vet Res 2001 December; 62(12):1876-80.

178. Voicu I L, Silim A, Morin M, Elazhary M A. Interaction of porcine reproductive and respiratory syndrome virus with swine monocytes. Vet Rec 1994 Apr. 16; 134(16):422-3.

179. Christopher-Hennings J, Nelson E A, Nelson J K, Rossow K D, Shivers J L, Yaeger M J, et al. Identification of porcine reproductive and respiratory syndrome virus in semen and tissues from vasectomized and nonvasectomized boars. Vet Pathol 1998 July; 35(4):260-7.

180. Van Reeth K, Labarque G, Nauwynck H, Pensaert M. Differential production of proinflammatory cytokines in the pig lung during different respiratory virus infections: correlations with pathogenicity. Res Vet Sci 1999 August; 67(1):47-52.

181. Meier W A, Galeota J, Osorio F A, Husmann R J, Schnitzlein W M, Zuckermann F A. Gradual development of the interferon-gamma response of swine to porcine reproductive and respiratory syndrome virus infection or vaccination. Virology 2003 Apr. 25; 309(1):18-31

182. Read S, Malmstrom V, Powrie F. Cytotoxic T lymphocyte-associated antigen 4 plays an essential role in the function of CD25(+)CD4(+) regulatory cells that control intestinal inflammation. J Exp Med 2000 Jul. 17; 192(2):295-302.

183. Sakaguchi S, Wing K, Onishi Y, Prieto-Martin P, Yamaguchi T. Regulatory T cells: how do they suppress immune responses? Int Immunol 2009 October; 21(10):1105-11
184. Van Reeth K, Van Gucht S, Pensaert M. In vivo studies on cytokine involvement during acute viral respiratory disease of swine: troublesome but rewarding. Vet Immunol Immunopathol 2002 Sep. 10; 87(3-4):161-8.
185. Li Y, Xue C, Wang L, Chen X, Chen F, Cao Y. Genomic analysis of two Chinese strains of porcine reproductive and respiratory syndrome viruses with different virulence. Virus Genes 2010 June; 40(3):374-81.
186. Martelli P, Gozio S, Ferrari L, Rosina S, De Angelis E, Quintavalla C, et al. Efficacy of a modified live porcine reproductive and respiratory syndrome virus (PRRSV) vaccine in pigs naturally exposed to a heterologous European (Italian cluster) field strain: Clinical protection and cell-mediated immunity. Vaccine 2009 Jun. 8; 27(28):3788-99.
187. Botner A, Strandbygaard B, Sorensen K J, Have P, Madsen K G, Madsen E S, et al. Appearance of acute PRRS-like symptoms in sow herds after vaccination with a modified live PRRS vaccine. Vet Rec 1997 Nov. 8; 141(19):497-9.
188. Murtaugh M P, Yuan S, Nelson E A, Faaberg K S. Genetic interaction between porcine reproductive and respiratory syndrome virus (PRRSV) strains in cell culture and in animals. J Swine Health Prod 2002; 10:15-21.
189. Mann J F, Acevedo R, Campo J D, Perez 0, Ferro V A. Delivery systems: a vaccine strategy for overcoming mucosal tolerance? Expert Rev Vaccines 2009 January; 8(1):103-12
190. Kamijuku H, Nagata Y, Jiang X, Ichinohe T, Tashiro T, Mori K, et al. Mechanism of NKT cell activation by intranasal coadministration of alpha-galactosylceramide, which can induce cross-protection against influenza viruses. Mucosal Immunol 2008 May; 1(3):208-18.
191. Guillonneau C, Mintern J D, Hubert F X, Hurt A C, Besra G S, Porcelli S, et al. Combined NKT cell activation and influenza virus vaccination boosts memory CTL generation and protective immunity. Proc Natl Acad Sci USA 2009 Mar. 3; 106(9):3330-5.
192. Doan L X, Li M, Chen C, Yao Q. Virus-like particles as HIV-1 vaccines. Rev Med Virol 2005 March-April; 15(2):75-88.
193. Schirmbeck R, Bohm W, Reimann J. Virus-like particles induce MHC class I-restricted T-cell responses. Lessons learned from the hepatitis B small surface antigen. Intervirology 1996; 39(1-2):111-9.
194. Murata K, Lechmann M, Qiao M, Gunji T, Alter H J, Liang T J. Immunization with hepatitis C virus-like particles protects mice from recombinant hepatitis C virus-vaccinia infection. Proc Natl Acad Sci USA 2003 May 27; 100(11):6753-8.
195. Paliard X, Liu Y, Wagner R, Wolf H, Baenziger J, Walker C M. Priming of strong, broad, and long-lived HIV type 1 p55gag-specific CD8+ cytotoxic T cells after administration of a virus-like particle vaccine in rhesus macaques. AIDS Res Hum Retroviruses 2000 Feb. 10; 16(3):273-82
196. Fausch S C, Da Silva D M, Kast W M. Differential uptake and cross-presentation of human papillomavirus virus-like particles by dendritic cells and Langerhans cells. Cancer Res 2003 Jul. 1; 63(13):3478-82.
197. Beyer T, Herrmann M, Reiser C, Bertling W, Hess J. Bacterial carriers and virus-like-particles as antigen delivery devices: role of dendritic cells in antigen presentation. Curr Drug Targets Infect Disord 2001 November; 1(3):287-302.
198. Semete B, Booysen L, Lemmer Y, Kalombo L, Katata L, Verschoor J, et al. In vivo evaluation of the biodistribution and safety of PLGA nanoparticles as drug delivery systems. Nanomedicine 2010 October; 6(5):662-71.
199. Cox M M. Progress on baculovirus-derived influenza vaccines. Curr Opin Mol Ther 2008 February; 10(1):56-61.
200. Roy P, Noad R. Virus-like particles as a vaccine delivery system: myths and facts. Hum Vaccin 2008 January-February; 4(1):5-12.
201. Plummer E M, Manchester M. Viral nanoparticles and virus-like particles: platforms for contemporary vaccine design. Wiley Interdiscip Rev Nanomed Nanobiotechnol 2010 Sep. 24.
202. French T J, Marshall J J, Roy P. Assembly of double-shelled, viruslike particles of bluetongue virus by the simultaneous expression of four structural proteins. J Virol 1990 December; 64(12):5695-700.
203. French T J, Roy P. Synthesis of bluetongue virus (BTV) corelike particles by a recombinant baculovirus expressing the two major structural core proteins of BTV. J Virol 1990 April; 64(4):1530-6.
204. Maranga L, Rueda P, Antonis A F, Vela C, Langeveld J P, Casal J I, et al. Large scale production and downstream processing of a recombinant porcine parvovirus vaccine. Appl Microbiol Biotechnol 2002 June; 59(1):45-50.

205. Caparros-Wanderley W, Clark B, Griffin B E. Effect of dose and long-term storage on the immunogenicity of murine polyomavirus VP1 virus-like particles. Vaccine 2004 Jan. 2; 22(3-4):352-61.

206. Antonis A F, Bruschke C J, Rueda P, Maranga L, Casal J I, Vela C, et al. A novel recombinant virus-like particle vaccine for prevention of porcine parvovirus-induced reproductive failure. Vaccine 2006 Jun. 29; 24(26):5481-90.

207. Paolicelli P, Prego C, Sanchez A, Alonso M J. Surface-modified PLGA-based nanoparticles that can efficiently associate and deliver virus-like particles. Nanomedicine (Lond) 2010 August; 5(6):843-53

208. Dybing J K, Jackwood D J. Antigenic and immunogenic properties of baculovirus-expressed infectious bursal disease viral proteins. Avian Dis 1998 January-March; 42(1):80-91.

209. Dybing J K, Jackwood D J. Expression of M D infectious bursal disease viral proteins in baculovirus. Avian Dis 1997 July-September; 41(3):617-26.

210. Latham T, Galarza J M. Formation of wild-type and chimeric influenza virus-like particles following simultaneous expression of only four structural proteins. J Virol 2001 July; 75(13):6154-65.

211. Belyaev A S, Roy P. Development of baculovirus triple and quadruple expression vectors: co-expression of three or four bluetongue virus proteins and the synthesis of bluetongue virus-like particles in insect cells. Nucleic Acids Res 1993 Mar. 11; 21(5):1219-23

212. Ling J, Liao H, Clark R, Wong M S, Lo D D. Structural constraints for the binding of short peptides to claudin-4 revealed by surface plasmon resonance. J Biol Chem 2008 Nov. 7; 283(45):30585-95.

213. Reischl D, Zimmer A. Drug delivery of siRNA therapeutics: potentials and limits of nanosystems. Nanomedicine 2009 March; 5(1):8-20.

214. Cano J P, Dee S A, Murtaugh M P, Trincado C A, Pijoan C B. Effect of vaccination with a modified-live porcine reproductive and respiratory syndrome virus vaccine on dynamics of homologous viral infection in pigs. Am J Vet Res 2007 May; 68(5):565-71.

215. Klinge K L, Vaughn E M, Roof M B, Bautista E M, Murtaugh M P. Age-dependent resistance to Porcine reproductive and respiratory syndrome virus replication in swine. Virol J 2009; 6:177.

What is claimed is:

1. A composition comprising an inactivated porcine reproductive and respiratory syndrome virus (PRRSV) entrapped within a nanoparticle, wherein the composition further comprises an adjuvant, wherein the adjuvant comprises a *Mycobacterium* lysate.

2. The composition of claim 1, wherein the adjuvant is a *Mycobacterium tuberculosis* whole cell lysate.

3. The composition of claim 1, wherein the adjuvant is selected from the group consisting of a *Mycobacterium smegmatis* whole cell lysate, *Mycobacterium tuberculosis* whole cell lysate, and *Mycobacterium vaccae* whole cell lysate.

4. The composition of claim 1, wherein the nanoparticle is immunogenic.

5. The composition of claim 1, wherein the inactivated PRRSV is entrapped within the nanoparticle by a water/oil/water emulsion method.

6. The composition of claim 1, wherein the nanoparticle is poly(lactide co-glycolide) (PLGA).

7. The composition of claim 6, wherein the PLGA is 50/50 PLGA.

8. The composition of claim 1, in a ratio of about 180 mg of PLGA to about 5 mg of inactivated PRRSV.

9. The composition of claim 1, wherein the inactivated PRRSV is the MN184 strain of PRRSV.

10. The composition of claim 1, wherein the inactivated PRRSV is inactivated by UV light or binary ethylenimine.

11. A vaccine comprising a composition of claim 1 in a carrier.

12. A method of eliciting an immune response against PRRSV in a pig comprising administering to said pig the vaccine of claim 11.

13. The method of claim 12, wherein the immune response is protective against PRRSV infection.

14. A method of reducing reproductive or respiratory failure in a pig comprising
administering to the pig the vaccine of claim 11 to.

15. A method of stimulating an immune response in a pig comprising:
administering to said pig the vaccine of claim 11.

16. The method of claim 12, wherein the vaccine is administered at a dose of between 100 ug/pig and 500 ug/pig.

17. The method of claim 12, wherein the vaccine is administered in a single dose.

18. The method of claim 12, wherein the vaccine is administered in two doses.

19. The method of claim 18, wherein the two doses are administered at about two week intervals.

20. The method of claim 12, wherein the vaccine is administered intranasally.

* * * * *